(12) United States Patent
Deichmann et al.

(10) Patent No.: US 8,032,337 B2
(45) Date of Patent: *Oct. 4, 2011

(54) METHOD FOR MODELING CUSTOMIZED EARPIECES

(75) Inventors: Nikolaj Deichmann, Copenhagen (DK); Tais Clausen, Copenhagen (DK); Rune Fisker, Copenhagen (DK); Christophe Vasiljev Barthe, Copenhagen (DK)

(73) Assignee: 3Shape A/S, Copenhagen (DK)

( * ) Notice: Subject to any disclaimer, the term of this patent is extended or adjusted under 35 U.S.C. 154(b) by 543 days.

This patent is subject to a terminal disclaimer.

(21) Appl. No.: 10/469,591

(22) PCT Filed: Mar. 1, 2002

(86) PCT No.: PCT/DK02/00137
§ 371 (c)(1), (2), (4) Date: Sep. 2, 2003

(87) PCT Pub. No.: WO02/071794
PCT Pub. Date: Sep. 12, 2002

(65) Prior Publication Data
US 2004/0107080 A1     Jun. 3, 2004

Related U.S. Application Data

(60) Provisional application No. 60/275,112, filed on Mar. 13, 2001.

(30) Foreign Application Priority Data

Mar. 2, 2001    (DK) ................................. 2001 00346
Mar. 28, 2001   (DK) ................................. 2001 00519
Oct. 17, 2001   (DK) ................................. 2001 01521

(51) Int. Cl.
*G06F 17/50*   (2006.01)
*H04R 25/00*   (2006.01)

(52) U.S. Cl. .............. 703/1; 703/2; 703/6; 345/419; 345/420; 381/312; 381/322; 381/324; 381/328

(58) Field of Classification Search ............. 703/1, 2, 703/6; 381/23.1, 312, 322, 324, 328; 345/419, 345/420, 427, 428, 621
See application file for complete search history.

(56) References Cited

U.S. PATENT DOCUMENTS 4,089,608 A   5/1978   Hoadley ................ 356/156
(Continued)

FOREIGN PATENT DOCUMENTS
AU   762679   1/2001
(Continued)

*Primary Examiner* — Kamini S Shah
*Assistant Examiner* — Kibrom Gebresilassie
(74) *Attorney, Agent, or Firm* — Buchanan Ingersoll & Rooney PC

(57) ABSTRACT

The present invention relates to a method for computer-controlled modelling of customised earpieces. These earpieces include housings for hearing aids, wireless or connected communication devices (headsets, mobile phones, personal agents), loud speakers, tinnitus masking devices, devices recording vibrations in the skull and transforming these into audio signals, voice recognition devices, earplugs, noise blockers with selective frequencies or sound levels, Man Machine Interface (MMI) products that enable clear communication even in the noisiest environments, or products related to wireless Internet applications. All these earpieces may be worn in the user's meatus and/or auditory canal. The invention also relates to a computerised system for manufacturing such customised earpieces. In particular, the invention is directed to a computerised system that models an earpiece based on a three-dimensional replica of the user's meatus and/or auditory canal.

120 Claims, 41 Drawing Sheets
(23 of 41 Drawing Sheet(s) Filed in Color)

U.S. PATENT DOCUMENTS

| | | | | |
|---|---|---|---|---|
| 4,185,918 | A | | 1/1980 | DiMatteo et al. ............. 356/375 |
| 4,575,805 | A | | 3/1986 | Moermann et al. ........... 364/474 |
| 4,705,401 | A | | 11/1987 | Addleman et al. ............ 356/376 |
| 4,737,032 | A | | 4/1988 | Addleman et al. ............ 356/376 |
| 4,871,502 | A | * | 10/1989 | LeBisch et al. ............... 264/222 |
| 4,984,277 | A | * | 1/1991 | Bisgaard et al. .............. 381/325 |
| 5,006,055 | A | * | 4/1991 | Lebisch et al. .................... 425/2 |
| 5,008,058 | A | * | 4/1991 | Henneberger et al. ........ 264/134 |
| 5,027,281 | A | | 6/1991 | Rekow et al. ............. 364/474.24 |
| 5,056,204 | A | * | 10/1991 | Bartschi ...................... 29/896.21 |
| 5,121,333 | A | * | 6/1992 | Riley et al. .................... 700/163 |
| 5,121,334 | A | | 6/1992 | Riley et al. ............. 364/474.05 |
| 5,128,870 | A | | 7/1992 | Erdman et al. .......... 364/474.05 |
| 5,172,685 | A | | 12/1992 | Nudelman ......................... 128/6 |
| 5,184,306 | A | * | 2/1993 | Erdman et al. ................ 700/163 |
| 5,257,203 | A | | 10/1993 | Riley et al. ............. 364/474.05 |
| 5,276,407 | A | | 1/1994 | Mead et al. |
| 5,381,786 | A | | 1/1995 | Spears |
| 5,404,408 | A | * | 4/1995 | Strohmaier et al. .......... 381/330 |
| 5,432,543 | A | | 7/1995 | Hasegawa et al. |
| 5,487,012 | A | * | 1/1996 | Topholm et al. .............. 700/163 |
| 5,501,096 | A | | 3/1996 | Stettner et al. .................... 73/1 J |
| 5,506,683 | A | | 4/1996 | Yang et al. ..................... 356/376 |
| 5,547,455 | A | | 8/1996 | McKenna et al. |
| 5,549,476 | A | | 8/1996 | Stern ............................... 433/223 |
| 5,552,992 | A | | 9/1996 | Hunter ...................... 364/468.25 |
| 5,561,526 | A | | 10/1996 | Huber et al. ................... 356/376 |
| 5,661,667 | A | | 8/1997 | Rueb et al. ..................... 364/525 |
| 5,717,455 | A | | 2/1998 | Kamewada |
| 5,741,215 | A | | 4/1998 | D'Urso .......................... 600/407 |
| 5,753,931 | A | | 5/1998 | Borchers et al. .......... 250/559.22 |
| 5,784,098 | A | | 7/1998 | Shoji et al. ....................... 348/45 |
| 5,831,719 | A | | 11/1998 | Berg et al. ..................... 356/5.13 |
| 5,864,640 | A | | 1/1999 | Miramonti et al. ........... 382/312 |
| 5,870,220 | A | | 2/1999 | Migdal et al. ................. 359/620 |
| 5,889,874 | A | * | 3/1999 | Schmitt et al. ................ 381/328 |
| 5,895,927 | A | | 4/1999 | Brown ...................... 250/559.19 |
| 5,936,628 | A | | 8/1999 | Kitamura et al. .............. 345/420 |
| 5,940,170 | A | | 8/1999 | Berg et al. ....................... 356/5.1 |
| 5,978,092 | A | | 11/1999 | Brown .......................... 356/376 |
| 5,991,437 | A | | 11/1999 | Migdal et al. ................. 382/154 |
| 6,044,170 | A | | 3/2000 | Migdal et al. ................. 382/154 |
| 6,081,273 | A | | 6/2000 | Weng et al. ................... 345/425 |
| 6,157,902 | A | * | 12/2000 | Hirata et al. ....................... 703/7 |
| 6,248,074 | B1 | | 6/2001 | Ohno et al. |
| 6,263,234 | B1 | | 7/2001 | Engelhardt et al. ........... 600/476 |
| 6,271,856 | B1 | * | 8/2001 | Krishnamurthy ............. 345/581 |
| 6,293,911 | B1 | | 9/2001 | Imaizumi et al. |
| 6,320,331 | B1 | | 11/2001 | Iida et al. |
| 6,377,865 | B1 | * | 4/2002 | Edelsbrunner et al. .......... 700/98 |
| 6,401,859 | B1 | * | 6/2002 | Widmer et al. ................ 181/135 |
| 6,518,966 | B1 | * | 2/2003 | Nakagawa .................... 345/422 |
| 6,533,062 | B1 | * | 3/2003 | Widmer et al. ................ 181/129 |
| 6,545,676 | B1 | * | 4/2003 | Ryan et al. .................... 345/423 |
| 6,629,065 | B1 | * | 9/2003 | Gadh et al. ......................... 703/1 |
| 6,725,184 | B1 | * | 4/2004 | Gadh et al. ......................... 703/2 |
| 6,748,093 | B2 | * | 6/2004 | Tøpholm ....................... 381/322 |
| 6,863,210 | B2 | * | 3/2005 | Becker et al. ................. 228/212 |
| 6,920,414 | B2 | * | 7/2005 | Tøpholm ........................... 703/1 |
| 6,928,396 | B2 | * | 8/2005 | Thackston ......................... 703/1 |
| 7,050,876 | B1 | * | 5/2006 | Fu et al. ......................... 700/118 |
| 7,162,323 | B2 | * | 1/2007 | Brumback et al. ............ 700/118 |
| 7,467,022 | B2 | * | 12/2008 | Bhagwat et al. ................ 700/98 |
| 7,571,018 | B2 | * | 8/2009 | Roth et al. ....................... 700/98 |
| 7,609,259 | B2 | * | 10/2009 | McBagonluri et al. ........ 345/419 |
| 7,672,823 | B2 | * | 3/2010 | Nikles et al. ....................... 703/7 |
| 2001/0031912 | A1 | | 10/2001 | Adler |
| 2002/0136420 | A1 | * | 9/2002 | Topholm ....................... 381/312 |
| 2002/0136421 | A1 | * | 9/2002 | Topholm ....................... 381/314 |
| 2002/0138237 | A1 | * | 9/2002 | Topholm ........................... 703/1 |
| 2002/0196954 | A1 | * | 12/2002 | Marxen et al. ................ 381/312 |
| 2003/0001835 | A1 | * | 1/2003 | Dimsdale et al. ............. 345/419 |
| 2003/0067461 | A1 | * | 4/2003 | Fletcher et al. ............... 345/420 |
| 2003/0072011 | A1 | * | 4/2003 | Shirley .......................... 356/601 |
| 2003/0074174 | A1 | * | 4/2003 | Fu et al. ........................... 703/13 |
| 2003/0152242 | A1 | * | 8/2003 | Marxen et al. ................ 381/312 |
| 2004/0165741 | A1 | * | 8/2004 | Fang et al. ..................... 381/322 |
| 2004/0264724 | A1 | * | 12/2004 | Fang et al. ..................... 381/322 |
| 2005/0088435 | A1 | * | 4/2005 | Geng ............................. 345/419 |
| 2007/0234571 | A1 | * | 10/2007 | Bhagwat et al. ........... 29/896.21 |
| 2009/0099677 | A1 | * | 4/2009 | McBagonluri et al. ........ 700/103 |
| 2009/0196447 | A1 | * | 8/2009 | McBagonluri et al. ........ 381/324 |
| 2010/0226502 | A1 | * | 9/2010 | De Finis et al. ................. 381/60 |
| 2011/0103630 | A1 | * | 5/2011 | Azernikov .................... 381/328 |

FOREIGN PATENT DOCUMENTS

| | | | |
|---|---|---|---|
| DE | 41 02 614 | | 8/1992 |
| DE | 198 03 679 | | 8/1999 |
| EP | 0 352 952 | | 1/1990 |
| EP | 0 233 920 | | 1/1991 |
| EP | 0 490 848 | | 6/1992 |
| GB | 2 104 652 | | 3/1983 |
| JP | 09-103000 | * | 4/1995 |
| JP | 9103000 | | 4/1997 |
| JP | 11337845 | | 12/1999 |
| WO | 91/13586 | | 9/1991 |
| WO | 92/11737 | | 7/1992 |
| WO | 96/10205 | | 4/1996 |
| WO | 97/32182 | | 9/1997 |
| WO | 98/59300 | | 12/1998 |
| WO | 99/28704 | | 6/1999 |
| WO | 00/04506 | | 1/2000 |
| WO | 00/04508 | | 1/2000 |
| WO | 00/07501 | | 2/2000 |
| WO | 00/34739 | | 6/2000 |
| WO | 01/05207 | | 1/2001 |
| WO | 01/22030 | | 3/2001 |

* cited by examiner 701 702

Model A 4001

4003

A - B 4004

Model B 4002

METHOD FOR MODELING CUSTOMIZED EARPIECES

This is a nationalization of PCT/DK02/00137 filed Mar. 1, 2002 and published in English.

This application is a non-provisional of U.S. provisional application Ser. No. 60/275,112 flied 13 Mar. 2001, which is hereby incorporated by reference in its entirety. It claims priority from Danish patent applications no PA 2001 00346 filed on 2 Mar. 2001, PA 2001 00519 filed on 28. March 2001 and PA 2001 01521 filed on 17 Oct. 2001, which are hereby incorporated by reference in their entirety.

All patent and non-patent references cited in the application, or in the present application, are also hereby incorporated by reference in their entirety.

TECHNICAL FIELD OF THE INVENTION

The present invention relates to a method for computer-controlled modelling of customised earpieces. These earpieces include housings for hearing aids, wireless or connected communication devices (headsets, mobile phones, personal agents), loud speakers, tinnitus masking devices, devices recording vibrations in the skull and transforming these into audio signals, voice recognition devices, earplugs, noise blockers with selective frequencies or sound levels, Man Machine Interface (MMI) products that enable clear communication even in the noisiest environments, or products related to wireless Internet applications. All these earpieces may be worn in the user's meatus and/or auditory canal. The invention also relates to a computerised system for manufacturing such customised earpieces. In particular, the invention is directed to a computerised system that models an earpiece based on a three-dimensional replica of the user's meatus and/or auditory canal. The system also provides for a number of operations and modifications to be performed on the reproduction.

BACKGROUND OF THE INVENTION

Many existing applications, such as in-the-ear (ITE), in-the-channel (ITC), or completely-in-the-channel (CIC) housings for hearing aids and personal communication devices (mobile phones or headsets) require the reproduction of one-of-a-kind parts of complex geometry. In these applications, the parts are unique and require a highly precise fit of the replacement part Sub-millimetre precision is for example required for ITE, ITC or CIC hearing aid housings; the housing Will otherwise cause inconvenience feedback, as well as irritation and possibly infection to the epidermis of the ear canal.

Existing methods to model and manufacture customised housings for hearing aids are very long and tedious processes. They introduce a great deal of uncertainty about the quality of the finished product. The process typically implies the creation of an impression of the user's ear canal. This impression must be adjusted manually and a mould replicating the user's meatus is created from the impression, either in plaster, gel, or silicone resin. A polymerisable liquid synthetic resin is produced, poured into the mould and polymerised at least partially. If the desired product is a shell for an individually fitted hearing aid housing, most of the liquid synthetic resin must be poured out of the mould again, before it completely polymerises. The resulting shell is ground to the desired size and appearance. The components must then be fitted manually into the shell; this operation is often problem-prone, since the shell has been designed without taking proper account of the components' shape and size.

PRIOR ART

U.S. Pat. No. 5,121,333, U.S. Pat. No. 5,121,334, U.S. Pat. No. 5,128,870. U.S. Pat. No. 5,184,306, U.S. Pat. No. 5,027,281, and U.S. Pat. No. 5,257,203 (REGENTS OF THE UNIVERSITY OF MINNESOTA) describe a method and apparatus for the automated reproduction of three-dimensional objects of complex and unique geometry. A computer acquires data describing an object and its surroundings, constructs a computer-based three dimensional model of the object from the data, superimposes an ideal geometry on the computer-based model, alters the ideal geometry to fit the form and function required of the reproduction, and then guides a milling machine in the fabrication of the reproduction.

WO 00/34739 (FAGAN ET AL.) concerns a method for manufacturing hearing aid shells involving the use of a specially adapted ultrasonic probe head to safely measure the contours of the ear canal without contact with the surface being measured. The recording of data in the ear canal is made possible by filling the canal with a liquid and inserting the ultrasonic probe The scan data is processed by a computer and the data is used with a rapid prototyping set-up such as stereo lithography, selective laser sintering, laminate object modelling, inkjet modelling, fused depositing modelling, 3D or any other system that produces real models from computer mathematical models to manufacture the hearing aid shell.

EP 0 516 808 (TØPHOLM & WESTERMANN APS) concerns a method for computer-assisted manufacture of otoplastics individually fitted to the contours of the ear canal. According to the described method a digital representation of the internal contours of the ear canal is used for the production of a hearing aid shell, and the digital representation Is used to obtain a computer model, which can be used for manual location of the components of the hearing aid and for defining the thickness of the shell's walls.

U.S. Pat. No. 5,056,204 (ASCOM AUDIOSYS AG) concerns a method for the milling of hearing aids whereby the internal contours of the ear canal are recorded by a laser apparatus located outside the ear of the user.

JP09103000A2 (RION CO LTD) describes a method for the production of shell for ear-inserted hearing aids whereby a three-dimensional shape measuring instrument is used to measure the shape information of the external auditory meatus directly or using a an ear model sampled by using a sealing member. Next, the shape information and information on the shape of the components to be integrated into a shell for hearing aid are inputted to a computer, and an external shape or an internal shape of the hearing aid shell is decided. Afterwards, the three-dimensional shape data of the external or internal shape decided by the computer system are inputted to an optical moulding device and the hearing aid shell is directly produced by an optical moulding method.

WO 01/05207 (PHONAK AG) discloses a method for production of otoplastics, whereby an impression of the shape of the individual auditory canal is taken in order to produce shells for hearing aids implanted in the ear that very precisely adapt to the individual shape of the auditory canal and a hearing aid shell is produced by means of an additive fabrication process such as laser sintering, stereolithography or a thermojet process that is controlled by means of data pertaining to the shape. The disclosure provides no information on how to model the otoplastics including the placement of components.

Just placing components (as mentioned in EP 0 516 808, TØPHOLM & WESTERMANN APS) or just cutting away parts of the original 3D model only give weak indications of the full earpiece and the result is likely to be of low quality. Furthermore, these prior art methods do not disclose how to model complex earpieces with more features.

While concepts for the computer-assisted modelling and subsequent direct manufacturing of custom-fitted earpieces, especially hearing aid housings, are mentioned in the prior art, none of the above-cited references directly discloses steps or operations, which may be involved in the modelling process of such customised earpieces. Thus, there is a need for a method and/or providing one or more such steps or operations that can be used in order to optimise the modelling and production of customised earpieces. Such a method and/or system is provided according to the present invention.

SUMMARY OF THE INVENTION

FIG. 5 shows an overview of how the tedious manual process can be computer-assisted or computer-controlled leading to faster production, lower cost and higher acoustic and physical quality. The process consists of three main steps: 3D scanning of the impression/ear, virtual 3D modelling of the earpiece and finally manufacturing. The invention primarily relates to 3D modelling of the original 3D model acquired by the scanner as illustrated in FIG. 10.

The invention enables the virtual creation of a complete earpiece by arranging relevant components in relation to the 3D model using collision control, cutting away the unwanted parts of the 3D model and forming a surface, which connects components and the 3D model. The creation of the full earpiece facilitates a true evaluation of the properties of the final earpiece, e.g. visual and acoustic properties and room for components taking into account the constraint by all surfaces. Additionally the virtual creation of the full earpieces enables the physical manufacturing of the full earpieces eliminating a large number of costly manual post processing operations.

According to a first aspect of the present invention there is provided a method for computer-assisted modelling of customised earpieces comprising at least one part being individually matched to an auditory canal and/or a meatus, said method comprising the steps of:
a) obtaining a three-dimensional computer model, 3D-model, of at least part of the auditory canal, said 3D-model having an outer surface,
b) initially arranging at least one component in relation to the 3D-model,
c) initially arranging a cutting curve or cutting surface in relation to the outer surface of the 3D-model, said cutting curve or surface dividing the 3D-model in an outer portion and an inner portion,
d) initially forming a connecting surface connecting the at least one component and the inner portion of the 3D-model, said connecting surface thereby being part of the 3D-model,
e) performing an evaluation of the arrangement of the at least one component, said evaluation comprising a collision detection of the at least one component in relation to one or more parts of the 3D-model and/or other components, and
f) adjusting the arrangement of the at least one component, the arrangement of the cutting curve or surface, and/or the formation of the connecting surface based on the result of said evaluation.

An initial cut to divide the 3D model in an inner and outer portion is not mentioned anywhere in the prior art relating to computer-assisted 3D modelling of customised earpieces. Such an initial cut is used in the manual modelling of earpieces based on impressions. In contrast to the manual method one primary advantage of the method according to the invention is that the initial cut performed on the 3D-model is optimisable, since it can be changed during the adjustment step based on the evaluation step. This is not possible when modelling earpieces manually and the possibility of optimising the initial cut in computer-assisted modelling of customised earpieces is mentioned nowhere in the prior art The fact that the initial cut can be optimised makes the method more flexible than the methods of the prior art.

According to the methods of the prior art, there is no guarantee that the components actually fit into the earpiece. In contrast to this the present invention physically places the components in the earpiece (in a modelling operation) to make sure that there is space for the components. According to the present invention, if there is too little room for the components, further rounds of optimisation can be performed, the optimisation process can be repeated, material can be removed from the shell or the initial cutting curve/surface can be moved to create more space.

The initial cut, dividing the 3D-model in an inner and outer portion also makes it possible to make a visualisation of the modelled earpiece in a virtual ear. Such visualisation and optimisation for appearance is not described in the prior art. The visual appearance of an earpiece is very important for the wearer.

Furthermore according to the present invention, there is provided a method for modelling the complete 3D earpiece with all its surfaces. The methods disclosed in the prior art fail to provide a disclosure of how to arrange a connecting surface connecting the 3D model with the at least component and thereby fail to teach a method for modelling the complete earpiece. The fact that the complete modelling of a 3D-earpiece is rendered possible by the instant invention, also makes it possible to make an optimisation of the acoustic properties of the earpiece in the computer prior to prototyping and assembling it. The fact that the complete earpiece can be modelled also makes it possible to prototype the whole piece in one operation thus obviating the need for assembling the piece from several pieces, such as an earpiece and a faceplate. However, it is still possible to incorporate a faceplate into the modelling according to the invention if so desired.

All 3D models irrespective of whether they are obtained by scanning an impression or by direct scanning of the auditory canal and/or meatus need to have at least the outer boundary of the piece modelled in order to obtain a complete earpiece.

Furthermore, the possibility of optimising the placement of the at least one component and the connecting surface gives the possibility of optimising the visual appearance of the piece in the arm.

In addition, an important advantage of the present invention is that the earpiece is only manufactured (through rapid prototyping) once it has been established that all the components of the earpiece are located in the optimum location.

The order of the steps of the method according to the invention can be any. Examples of preferred orders include, but are not limited to a) b) c) d) e) f); a) c) b) d) e) f); a) c) b) e) d) f); a) b) e) c) d) f); a) b) c) e) d) f). A preferred order is a) b) c) d) e) f), because it has turned out that by arranging the at least one component first, and arranging the cutting curve/surface with the aid of the at least one component makes it possible to model an optimal connecting surface in fewer steps and often to reach the optimal or at least an acceptable placement of the connecting surface in just one round.

The adjustment process may include either the arrangement of the at least one component, the arrangement of the cutting curve or surface, or the formation of the connecting surface or it may include any combinations of the arrangement of the at least one component, the arrangement of the cutting curve or surface, and/or the formation of the connecting surface. It is preferred that when the arrangement of the at least one component and/or the arrangement of the cutting curve or surface has/have been adjusted, the formation of the connecting surface is adjusted.

According to an embodiment of the invention, the arrangement of the at least one component in relation to the 3D-model may comprise arranging the at least one component in relation to a component surface, and arranging said component surface in relation to the 3D-model. Here, the connecting surface may be connecting said component surface and said inner portion of the 3D-model, It is preferred that the collision detection includes a collision detection of the component surface in relation to one or more parts of the 3D-model.

The collision detection may further include a collision detection of the mutual arrangement of the components themselves.

When arranging the components, it is preferred that the initial arrangement of the at least one component in relation to the 3D-model comprises arranging at least part of the components substantially at the interior of the 3D-model.

It should be understood that it is also within the present invention to have the evaluation process including an evaluation of the arrangement of the cutting curve or surface and/or the connecting surface.

It is preferred that the formation of the connecting surface is computer controlled or computer assisted. It is also preferred that the formation of the connecting surface comprises a lofting process, where the lofting process may comprise fitting a parametric surface to the boundary of the inner portion of the 3D-model and to the boundary of a surface defining an outer boundary of the arrangement of said at least one component in relation to the 3D-model. Here, the outer boundary of the arrangement of said at least one component in relation to the 3D-model may be defined by the outer boundary of the component surface.

It is also within an embodiment of the invention that the formation of the connecting surface comprises a filleting process of the edge or boundary of the inner portion of the 3D-model. Here, the outer shell surface of the 3D-model may be given in a vertex representation with the vertices being connected by triangles, and the filleting process may comprise removing at least part of the triangles in a neighbourhood around at least part of said edge and fitting a parametric surface to the neighbourhood of the hole created by the removed triangles.

According to an embodiment of the invention, at least part of the inner portion of the 3D-model is shelled. Here, the shelling process may be part of a modelling process according to the present invention, and the shelled inner portion may have an inner and an outer shell surface.

According to a preferred embodiment of the invention, the inner portion of the 3D-model at least partly comprises a representation of a model of an earpiece.

In another embodiment of the invention the outer portion of the 3D-model at least partly comprises a model of a virtual ear.

It should be understood that it is preferred that said one or more parts of the 3D model in relation to which the collision detection may be performed comprise at least part of the inner portion and/or at least part of the outer portion of the 3D-model. Here, said one or more parts of the 3D-model in relation to which the collision detection may be performed may comprise at least part of the inner shell surface and/or at least part of an inner surface of the virtual ear.

According to a preferred embodiment of the invention the collision detection and the adjustment, process may be repeated until the collision detection fulfils a required minimum criterion.

It should be understood that the initial arrangement of the at least one component and/or the cutting curve or surface may be performed in several ways in accordance with the present invention. Thus, the initial arrangement may be performed manually or be computer-controlled or computer-assisted. The initial arrangement may be performed using a feature-based approach, in which features extracted from the obtained 3D-model are used for the arrangement, or performed using a similarity-based approach, in which the obtained 3D-model is compared to a number of stored 3D-models of previously generated optimised models.

When using a similarity-based approach a stored optimised 3D-model may be selected as the most similar 3D-model and the initial arrangement of the at least one component and/or the cutting curve or surface may be selected substantially equal to the optimised arrangement of the at least one component and/or cutting curve or surface of said most similar 3D-model. Here, the comparison of 3D-models and selection of the most similar 3D-model may be computer-controlled or computer-assisted.

It should also be understood that according to the present invention, the adjustment of the arrangement of the at least one component and/or the cutting curve or surface may be performed manually or be computer-controlled or computer-assisted. A computer-controlled or computer-assisted adjustment process may also or alternatively include the adjustment of the formation of the connecting surface. The adjustment process of the arrangement of the at least one component, and/or the arrangement of the cutting curve or surface, and/or the formation of the connecting surface may be adjusted until no collision is detected.

According to the present invention, the collision detection may be performed in several ways. Thus, the collision detection may be performed by manual inspection of the three-dimensional computer model or the collision detection may be computer-controlled or computer-assisted.

In a preferred embodiment of the present invention a rule-based approach may be used for the arrangement of the at least one component and/or the arrangement of the cutting curve or surface. Here, an object function, $f(v)$, may be used. The object function may be defined for expressing the quality of the arrangement of the at least one component, and/or the arrangement of the cutting curve or surface, and/or the formation of the connecting surface. The object function may be an increasing function of the number of detected collisions and may be calculated for each new arrangement of the at least one component and/or the cutting curve or surface. It is preferred that the arrangement of the at least one component, and/or the arrangement of the cutting curve or surface, and/or the formation of the connecting surface may be adjusted until the object function fulfils a given minimum criterion. Here, the minimum criterion may be that the object function obtains a minimum value, or that the difference in the values of two successively determined object functions is below a defined value. When using an object function, different weights may be assigned to different detected collisions.

It is preferred that the arrangement of the component surface and/or the arrangement of the connecting surface can be adjusted without changing the arrangement of the at least one component. It is also preferred that the arrangement of the at least one component can be adjusted without changing the arrangement of the component surface and/or the arrangement of the connecting surface.

It should be understood that the component surface can take any convenient form; thus the surface may be a planar surface or a non-planar surface.

Although components may be arranged in relation to the 3D-model so as not to extend or so as to only extend partly into the interior portion of the 3D-model, it is also within embodiments of the present invention that components may be arranged at the interior or inner surface of the inner portion of the 3D-model.

For 3D-models being shelled according to the present invention, the shell of the 3D-model is preferred to have a predetermined minimum thickness. Within the present invention the shell is also generated by a shelling process being computer-controlled or computer-assisted. Here, the at least partly shelled 3D-model may be obtained from a three-dimensional computer model, 30-model, of at least part of the auditory canal, said 3D-model having an outer shell surface being parameterised by a number of vertices, which vertices are connected by triangles, said shelling process comprising:
offsetting inwardly a copy of each vertex in the outer shell surface,
removing the number of copied vertices being closer to the outer shell surface than a given minimum shell thickness, and
creating an inner shell by triangulation of the remaining copied vertices.

Within the present invention the inner shell surface or geometry of the 3D-model is also modified in order to improve the strength of the finished shell, said modification comprising adding extra material to the inner surface of the shell, while at the same time avoiding collision between the modified inner shell surface and the arranged at least one component. Here, the addition of extra material to the inner shell surface of the 3D-model may be performed using a Boolean operation, such as a Boolean addition, using a transfer function or using an outward offset of the vertices representing the surface A number of different components may be arranged in relation to the 3D-model. Such components may for example be selected from a list of components comprising electronic components, battery devices, outlets to interior components, tubes, transducers and logos.

In order to obtain a final 3D-model, further steps may be included in the modelling process. Such steps may comprise: arrangement of a ventilation channel at the interior or inner surface of the inner portion of the 3D-model, an optimisation of the visual appearance, and/or placement of a unique identifier at the inner portion of the 3D-model.

According to a further aspect the invention relates to a computer program product including a computer readable medium, said computer readable medium having a computer program stored thereon, said program for causing computer-assisted modelling of customised earpieces comprising at least one part being individually matched to an auditory canal, said program comprising:
program code for causing a computer to obtain a three-dimensional computer model, 3D-model, of at least part of the auditory canal, said 3D-model having an outer surface,
program code for causing a computer to initially arrange at least one component in relation to the 3D-model,
program code for causing a computer to initially arrange a cutting curve or cutting surface in relation to the outer surface of the 3D-model, said cutting curve or surface dividing the 3D-model in an outer portion and an inner portion,
program code for causing a computer to initially form a connecting surface connecting the at least one component and the inner portion of the 3D-model, said connecting surface thereby being part of the 3D-model,
program code for causing a computer to perform an evaluation of the arrangement of the at least one component, said evaluation comprising a collision detection of the at least one component in relation to one or more parts of the 3D-model, and
program code for causing a computer to adjust the arrangement of the at least one component, the arrangement of the cutting curve or surface, and/or the formation of the connecting surface based on the result of said evaluation.

The computer program product is especially adapted for causing a computer to perform the operations of the method according to the first aspect of the invention and may further comprise program code for causing a computer to perform any of the steps of any of the features of the method according to the invention.

The computer program product may be in the physical form of a hard disc, a floppy disc, a magnetic data carrier, a ZIP, a smart card, a CD ROM, or a DVD.

According to a further aspect the invention relates to a computer data signal embodied in a signal wave, said computer data signal including a computer program, said program for causing computer-assisted modelling of customised earpieces comprising at least one part being individually matched to an auditory canal, said program comprising:
program code for causing a computer to obtain a three-dimensional computer model, 3D-model, of at least part of the auditory canal, said 3D-model having an outer surface,
program code for causing a computer to initially arrange at least one component in relation to the 3D-model,
program code for causing a computer to initially arrange a cutting curve or cutting surface in relation to the outer surface of the 3D-model; said cutting curve or surface dividing the 3D-model in an outer portion and an inner portion,
program code for causing a computer to initially form a connecting surface connecting the at least one component and the inner portion of the 3D-model, said connecting surface thereby being part of the 3D-model,
program code for causing a computer to perform an evaluation of the arrangement of the at least one component, said evaluation comprising a collision detection of the at least one component in relation to one or more parts of the 3D-model, and
program code for causing a computer to adjust the arrangement of the at least one component, the arrangement of the cutting curve or surface, and/or the formation of the connecting surface based on the result of said evaluation.

The computer data signal is especially adapted for causing a computer to perform the operations of the method according to the first aspect of the invention and may further comprise program code for causing a computer to perform any of the steps of any of the features of the method according to the invention.

According to a further aspect the invention relates to a system for computer-assisted modelling of customised earpieces, said system including computer readable memory having one or more computer instructions stored thereon, said instructions comprising instructions operative to cause the computer to obtain a three-dimensional computer model, 3D-model, of at least part of the auditory canal, said 3D-model having an outer surface, instructions operative to cause the computer to initially arrange at least one component in relation to the 3D-model, instructions operative to cause the computer to initially arrange a cutting curve or cutting surface in relation to the outer surface of the 3D-model said cutting curve or surface dividing the 3D-model in an outer portion and an inner portion, instructions operative to cause the computer to initially form a connecting surface connecting the at least one component and the inner portion of the 3D-model said connecting surface thereby being part of the 3D-model, instructions operative to cause the computer to perform an evaluation of the arrangement of the at least one component, said evaluation comprising a collision detection of the at least one component in relation to one or more parts of the 3D-model, and instructions operative to cause the computer to adjust the arrangement of the at least one component, the arrangement of the cutting curve or surface, and/or the formation of the connecting surface based on the result of said evaluation.

The system is especially adapted for performing the operations of the method according to the first aspect of the invention and may further comprise instructions operative for causing the computer to perform any of the steps of any of the features of the method according to the invention.

Preferably the system according comprises a 3D scanner, a computer and a computer controllable rapid prototyping machine. Thereby is provided a complete system for scanning, modelling and prototyping customised earpieces.

The rapid prototyping machine may be any rapid prototyping machine capable of being controlled by a computer. Examples include but are not limited to machines capable of performing 3D milling and/or stereo lithography/SLA and/or solid ground curing and/or selective laser sintering and/or direct shell production casting and/or 3D-printing and/or topographic shell fabrication and/or fused deposition modelling and/or inkjet modelling and/or laminated object manufacturing and/or nano-printing.

The system may be arranged in different ways. Accordingly, the scanner and/or the prototyping machine may be connected to the computer via a local area network or the scanner and/or the prototyping machine may be connected to the computer via the internet.

Consequently the 3D scanner, the computer and the rapid prototyping machine may be placed in the same locality. Alternatively, the computer for modelling may be is placed at a "modelling site", where trained staff can perform the optional manual steps of the modelling. According to this embodiment, scan data can be sent via the internet or via other data transmission systems to the "modelling site".

Similarly, the rapid prototyping machine may be placed at a "rapid prototyping site", where the very costly machinery can be operated efficiently and on a 24 hour basis to keep production costs low.

The 3D scanner is conveniently placed by an audiologist or an otologist, especially when the scanner is a 3D structured light scanner for scanning the internal contours of the ear canal and/or meatus.

Preferably the system further comprises a database, wherein scan data are stored. According to an especially preferred embodiment of the invention, the system comprises a further database, wherein 3D data for customised earpieces are stored. These databases can be accessed during modelling of the earpieces and are especially useful when the method is performed on a similarity based approach.

The data are preferably stored together with information identifying the users of the customised earpieces.

An optional further database, comprises 3D data for components from different manufacturers. These can also be used for the modelling process.

Further optional hardware includes, but is not limited to Spaceball™ tracking device to assist in manual or computer assisted modelling and stereo glasses to assist in manual inspection of 3D computer screen models.

According to a further aspect of the present invention there is provided a method for computer-assisted modelling of customised earpieces comprising at least one part being individually matched to an auditory canal and/or a meatus, said method comprising the steps of:

a) obtaining a three-dimensional computer model, 3D-model, of at least part of the auditory canal, said 3D-model having an outer surface, b) initially arranging a at least one component in relation to the 3D-model, c) initially arranging a cutting curve or cutting surface in relation to the outer surface of the 3D-model, said cutting curve or surface dividing the 3D-model in an outer portion and an inner portion, d) initially forming a closing surface closing the hole partly or completely created in the 3D model by the cutting curve/cutting surface, e) performing an evaluation of the arrangement of the at least one component, said evaluation comprising a collision detection of the components in relation to one or more parts of the 3D-model and/or other components, and f) adjusting the arrangement of the at least one component, the arrangement of the cutting curve or surface, and/or the formation of the connecting surface based on the result of said evaluation.

According to the present aspect of the invention is provided a different method for modelling earpieces. If the closing surface is not completely closed and if the at least one component is places in the hole, the closing surface fulfils the same function as the connecting surface according to the first aspect of the invention. Another possibility according to this aspect of the invention is to model an 3D earpiece with a hole into which the components of the earpiece can be inserted after prototyping. It should be understood that the method of the second aspect of the present invention may be combined with any of the methods of the first aspect of the invention, wherein the components are arranged in relation to a cutting surface.

This aspect of the invention may also be in the embodiment of a computer program product or a computer data signal embodied in a signal wave comprising computer program code for performing the method and in the embodiment of a system including computer readable memory having one or more instructions stored thereon, the instructions comprising instructions operative for causing the system to perform the method.

According to a further aspect of the present invention there is provided a method for computer-assisted modelling of customised earpieces comprising at least one part being individually matched to an auditory canal, said method comprising the steps of:

obtaining a three-dimensional computer model, 3D-model, of at least part of the auditory canal, said 3D-model having an outer surface, initially arranging at least one component in relation to the 3D-model, initially arranging a cutting curve or surface in relation to the outer surface of the 3D-model, said cutting curve or surface dividing the 30-model in an outer portion and an inner portion, said initial arrangement of the cutting curve or surface and the components being performed using a similarity-based approach in which the present obtained 3D-model is compared to a number of stored models of previously generated optimised 3D-models, with one of said stored 3D-models being selected as the most similar model and the initially arrangements of the cutting curve or surface and the components being set substantially equal to the optimised arrangements of the cutting curve or surface and the components of said most similar 3D-model.

Here, the comparison of the present 3D-models and selection of the most similar 3D-model may be computer controlled or computer assisted. Also, the selection of initial arrangement of the cutting curve or surface and components may be computer controlled or computer assisted.

This aspect of the invention may also be in the embodiment of a computer program product or a computer data signal embodied in a signal wave comprising computer program code for performing the method and in the embodiment of a system including computer readable memory having one or more instructions stored thereon, the instructions comprising instructions operative for causing the system to perform the method.

It is preferred that the method of this aspect of the invention further-comprises the step of initially forming a connecting surface connecting the components and the inner portion of the 3D-model, said connecting surface thereby being part of the 3D-model.

The method of the this aspect of the present invention should preferably further comprise the steps of performing a collision detection of said arranged components in relation to one or more parts of the 3D-model, and adjusting the arrangement of the at least one component and/or the arrangement of the cutting curve or surface based on the result of said collision detection. Here, the adjustment of the arrangement of the cutting curve or surface and/or the arrangement of the at least one component may be repeated until the collision detection fulfils a required minimum criterion.

According to a further aspect the invention relates to a method for computer-assisted modelling of customised earpieces comprising at least one part being individually matched to an auditory canal, said method comprising the steps of:

obtaining a three-dimensional computer model, 3D-model, of at least part of the auditory canal, said 3D-model having an outer surface, initially arranging a at least one component in relation to the 3D-model, initially arranging a cutting curve or cutting surface in relation to the outer surface of the 3D-model, said cutting curve or surface dividing the 3D-model in an outer portion and an inner portion, said initial arrangement of the at least one component and/or cutting curve or surface being performed using a feature-based approach, in which features extracted from the obtained 3D-model are used for the arrangement.

This aspect of the invention may also be in the embodiment of a computer program product or a computer data signal embodied in a signal wave comprising computer program code for performing the method and in the embodiment of a system including computer readable memory having one or more instructions stored thereon, the instructions comprising instructions operative for causing the system to perform the method.

For the embodiments of the first aspects of the present invention, the 3D-model, present 3D-model or previously stored optimised 3D-models may have an outer shell surface being parameterised by a number of vertices, which vertices are connected by triangles. For the embodiments using a similarity-based approach the selection of the most similar 3D-model may comprise:

extracting a number of features from the obtained or present 3D-model, comparing said number of extracted features with corresponding stored features of a number of stored previously optimised 3D-models, and selecting a number of stored 3D-models as candidates for the most similar 3D-model, said candidates being the stored 3D-models having the compared features being nearest neighbours, in a feature space, to the feature points of the present 3D-model.

The selection process may further comprise:

registration of the present 3D-model and the selected candidate 3D-models, selection of the most similar 3D-model as the model of candidate 30-models having the smallest between the outer shell surface of said candidate 3D-model and the outer shell surface of the present 3D-model.

It should be understood that the methods of the third aspect of the present invention may be combined with any of the methods of the first and second aspects of the invention using a similarity based approach.

According to a still further aspect of the present invention there is provided a method for shelling a 3D model, said method comprising the steps of:

obtaining a three-dimensional computer model, 3D-model, of at least part of the auditory canal, said 3D-model having an outer shell surface being parameterised by a number of vertices, which vertices are connected by triangles, and performing a shelling process to obtain a shelled 3D-model of at least part of the auditory canal, said shelling process comprising:

offsetting inwardly a copy of each vertex in the outer shell surface, removing the number of copied vertices being closer to the outer shell surface than a given minimum shell thickness, and creating an inner shell by triangulation of the remaining copied vertices.

According to a further aspect the invention relates to a computer program product including a computer readable medium, said computer readable medium having a computer program stored thereon, said program for causing computer-assisted shelling of a 3D model, said program comprising:

program code for causing a computer to obtain a three-dimensional computer model, 3D model, of at least part of the auditory canal, said 3D-model having an outer shell surface being parameterised by a number of vertices which vertices are connected by triangles, and program code for causing a computer to perform a shelling process to obtain a shelled 3D-model of at least part of the auditory canal, said shelling process comprising:

program code for causing a computer to offset inwardly a copy of each vertex in the outer shell surface, program code for causing a computer to remove the number of copied vertices being closer to the outer shell surface than a given minimum shell thickness, and program code for causing a computer to create an inner shell by triangulation of the remaining copied vertices.

According to a still further aspect the invention relates to a computer data signal embodied in a signal wave, said computer data signal including a computer program, said program for causing computer-assisted shelling of a 3D model, said program comprising:
program code for causing a computer to obtain a three-dimensional computer model, 3D-model, of at least part of the auditory canal, said 3D-model having an outer shell surface being parameterised by a number of vertices, which vertices are connected by triangles, and
program code for causing a computer to perform a shelling process to obtain a shelled 3D-model of at least part of the auditory canal, said shelling process comprising:
program code for causing a computer to offset inwardly a copy of each vertex in the outer shell surface,
program code for causing a computer to remove the number of copied vertices being closer to the outer shell surface than a given minimum shell thickness, and
program code for causing a computer to create an inner shell by triangulation of the remaining copied vertices.

Furthermore, the invention relates to a system for computer assisted shelling of a 3D-model said system including computer readable memory having one or more computer instructions, stored thereon, said instructions comprising:
instructions operative to cause the computer to obtain a three-dimensional computer model, 3D-model, of at least part of the auditory canal, said 3D-model having an outer shell surface being parameterised by a number of vertices, which vertices are connected by triangles, and
instructions operative to cause the computer to perform a shelling process to obtain a shelled 3D-Model of at least part of the auditory canal, said shelling process comprising:
instructions operative to cause the computer to offset inwardly a copy of each vertex in the outer shell surface.
instructions operative to cause the computer to remove the number of copied vertices being closer to the outer shell surface than a given minimum shell thickness, and
instructions operative to cause the computer to create an inner shell by triangulation of the remaining copied vertices.

Also here it should be understood that the shelling method according to the last aspects of the present invention may be used in any of the methods of the first aspects of the present invention in order to obtain a shelled 3D-model.

The shelling algorithm according to the present invention makes it possible to perform shelling in a rapid and simple way.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention will now be explained in more detail in conjunction with the enclosed drawings on the basis of various example embodiments in which.

1. DETAILED DESCRIPTION OF THE INVENTION

1.1 General Definitions

Figure 1:
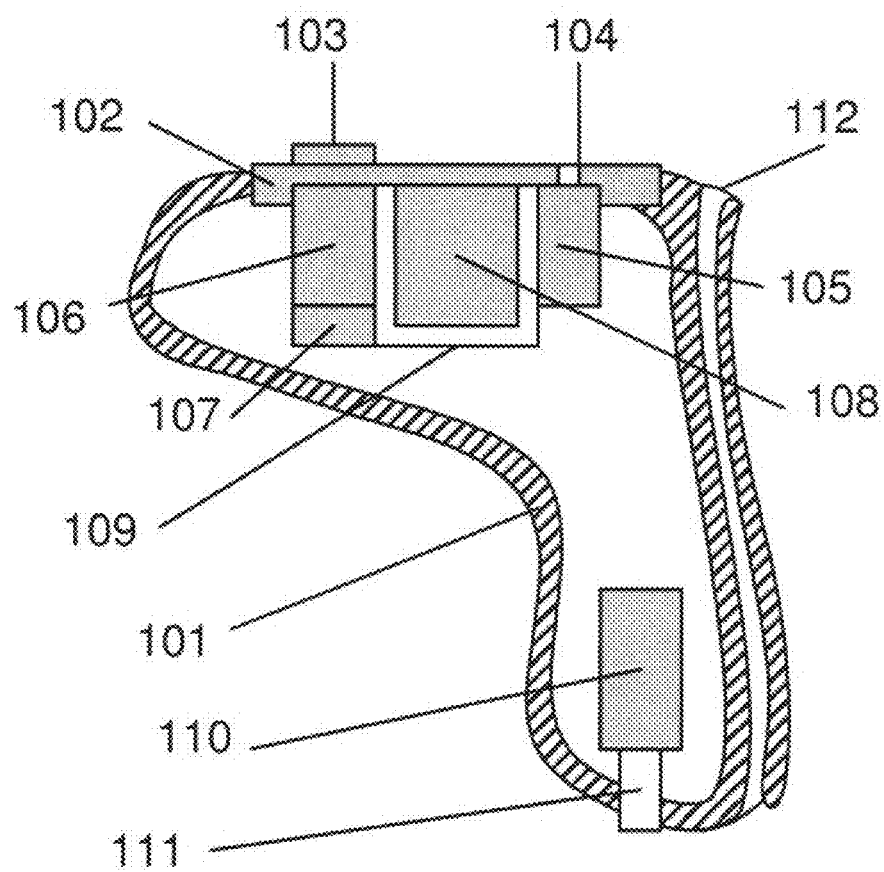
FIG. 1 shows an In-The-Ear Hearing Aid.

3D: A General Abbreviation for Three-Dimensional.

3D modelling operations: A number of different operations that alter the geometry of the original 3D model. These operations are used to change the outer and inner geometry of the earpiece. The 3D modelling operations are also used to make an optimal placement of the inner components of the apparatus.

3D model: A geometric representation of an object. This can either be an object of unique and complex geometry obtained by using a three dimensional scanning device or an object parametrically generated using a traditional CAD system or another 3D modelling software program. Different types of representations of 3D models exist. In one of the most common representation the 3D model is parameterised by a number of vertices, which are connected by triangles, see FIG. 7.

Original 3D model: The 3D scan of the meatus and/or auditory canal before any 3D modelling operations have been performed on the model. This model is often generated by scanning an impression of the auditory canal using an optical, acoustic, mechanical, or other 3D scanning apparatus. The original 3D model can also be obtained by using an intra canal 3D scanning device.

Present 3D model: A 3D model that exists as a temporary step in the total 3D modelling sequence. The present 3D model can therefore be any representation of the 3D model between the Original 3D model and the Final 3D model.

Final 3D model: A 3D model of the final earpiece. The final 3D model usually includes the geometry of the arranged components. Other useful geometric alterations of the original 3D model are also covered by this definition.

Component: A general term used for any type of component, feature or unit used with the device. Examples of components are ventilation channel, amplifier, Microphone, vibration pick-up, microchip, transducer, wireless communication/identification devices, position sensors such as GPS, loudspeaker, tubes, battery, printed circuits, faceplate, surface patches, inlets, outlets, wires, conductors, volume controls, nail grip, extraction cord, tele coil, locking means, interface modules, identification and logo.

Cutting tool: A tool such as an arbitrary curve or surface used to divide the model into two portions, where one of the portions are cut away, see e.g. FIG. 13 or FIG. 22.

Earpiece: The earpiece includes housings for hearing aids, wireless or connected communication devices (headsets, mobile phones, personal agents), loud speakers, tinnitus masking devices, devices recording vibrations in the skull and transforming these into audio signals, voice recognition devices, earplugs, noise blockers with selective frequencies or sound levels, Man Machine Interface (MMI) products that enable clear communication even in the easiest environments, or products related to wireless Internet applications.

Canal part of the surface: The canal part of the surface corresponds to the part of the model surface, which is inside the auditory canal, see FIG. 6

Inner shell surface: The surface corresponding to the internal part of the shell 2603, see FIG. 26.

Outer shell surface: The surface corresponding to the outer part of the shell 2604, see FIG. 26.

Visible part of the surface: The visible part of the surface is defined as part of the model surface, which is partly or fully visible when the earpiece is inserted in the ear.

Triangulation: The process of connecting vertices by triangles.

Vertex: A point in the 3D space. The vertices are connected by edges forming simple polygons, e.g. triangles, see FIG. 7.

Connecting surface: A connecting surface (FIG. 24, 2401) is a generated surface connecting a component with the inner portion of the 3D model. The connecting surface may also be defined as a generated surface connecting a component surface with the inner portion of the 3D model. In the finished product the connecting surface may either be printed/produced together with the inner portion of the customised earpiece or it may be formed by milling it in a faceplate part (FIG. 38, 3803) in which a component can be inserted.

Cutting curve/surface; A cutting curve/cutting surface is a curve/surface defined by the user or the computer and dividing the 3D model into a outer and inner portion. See FIG. 13; 1303 and FIG. 38, 3801 for examples of a cutting surface and FIG. 22, 2203 for an example of a cutting curve.

Figure 22:
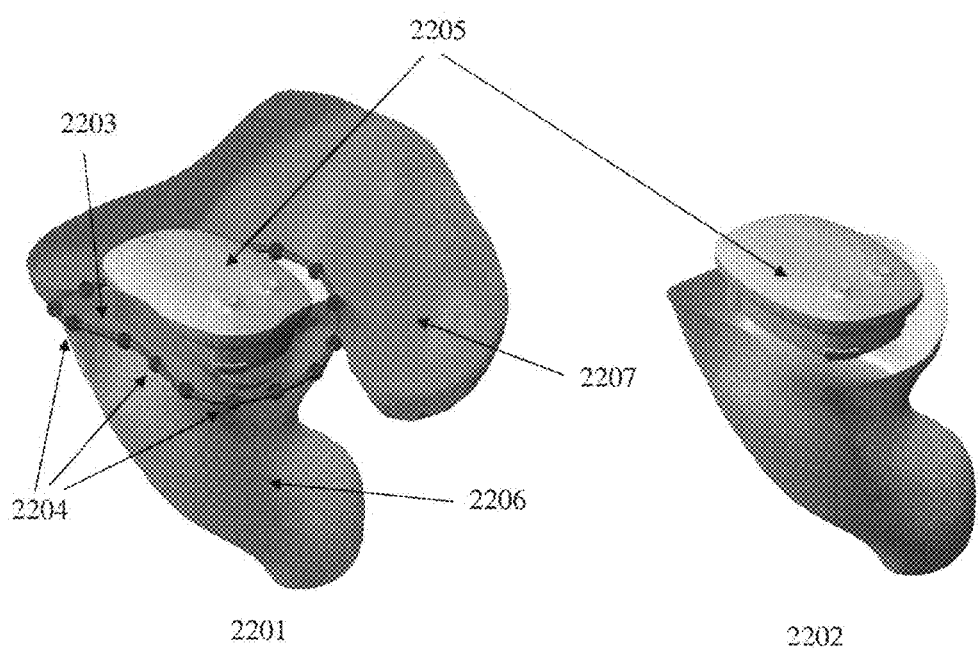
FIG. 22 shows a cutting by a closed curve on the surface. The curve is defined by the number of control points.

Outer portion/Inner portion: The terms are used to designate the two' parts of the model that arise as a result of cutting of the 3D model with a cutting curve or surface, The inner portion is the portion of the model; which is closest to the meatus of the user. FIG. 22 shows an example of a 3D model divided into an inner portion 2206 and outer portion 2207. The outer portion of the 3D model may form a virtual ear.

Figure 18:
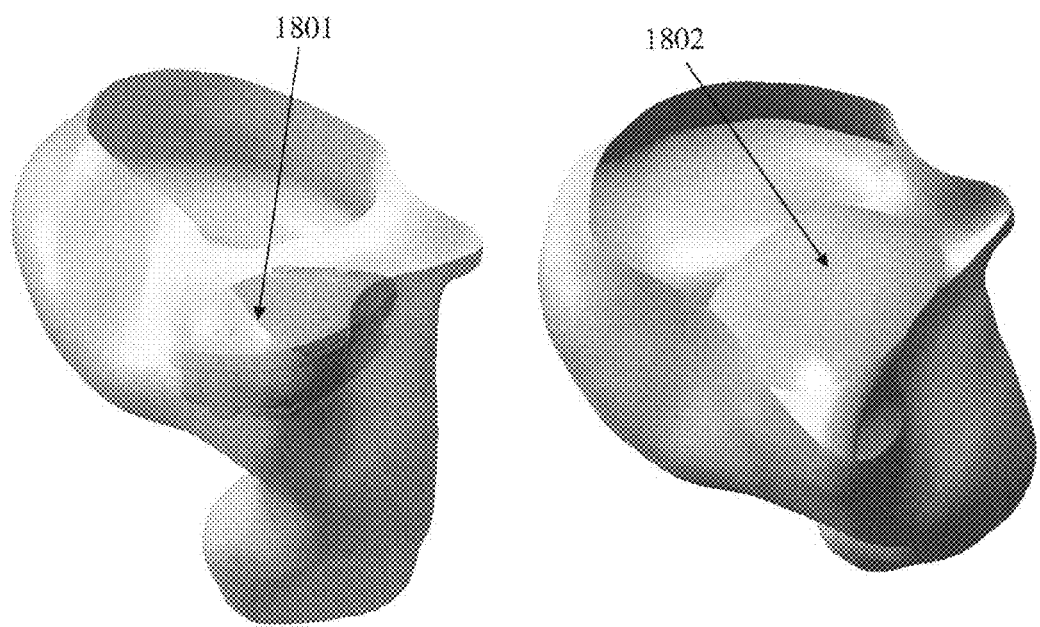
FIG. 18 illustrates a manual placement of the component surface and the components—in this case an integrated battery and electronics.

Component surface: The components are usually arranged in relation to a related component surface, which is then connected with the rest of the shell preferably by a cutting or loft operation. An alternative strategy is to create the component surface directly from the arranged components. The component surface is not necessarily an integrated part of the final 3D model. It could be a separate cover or faceplate, which is assembled with the shell later in the production process. FIG. 18 illustrates the arrangement of the component consisting of electronics and battery 1801 and the related component surface 1802.

1.2 General Specification of the System

Figure 2:
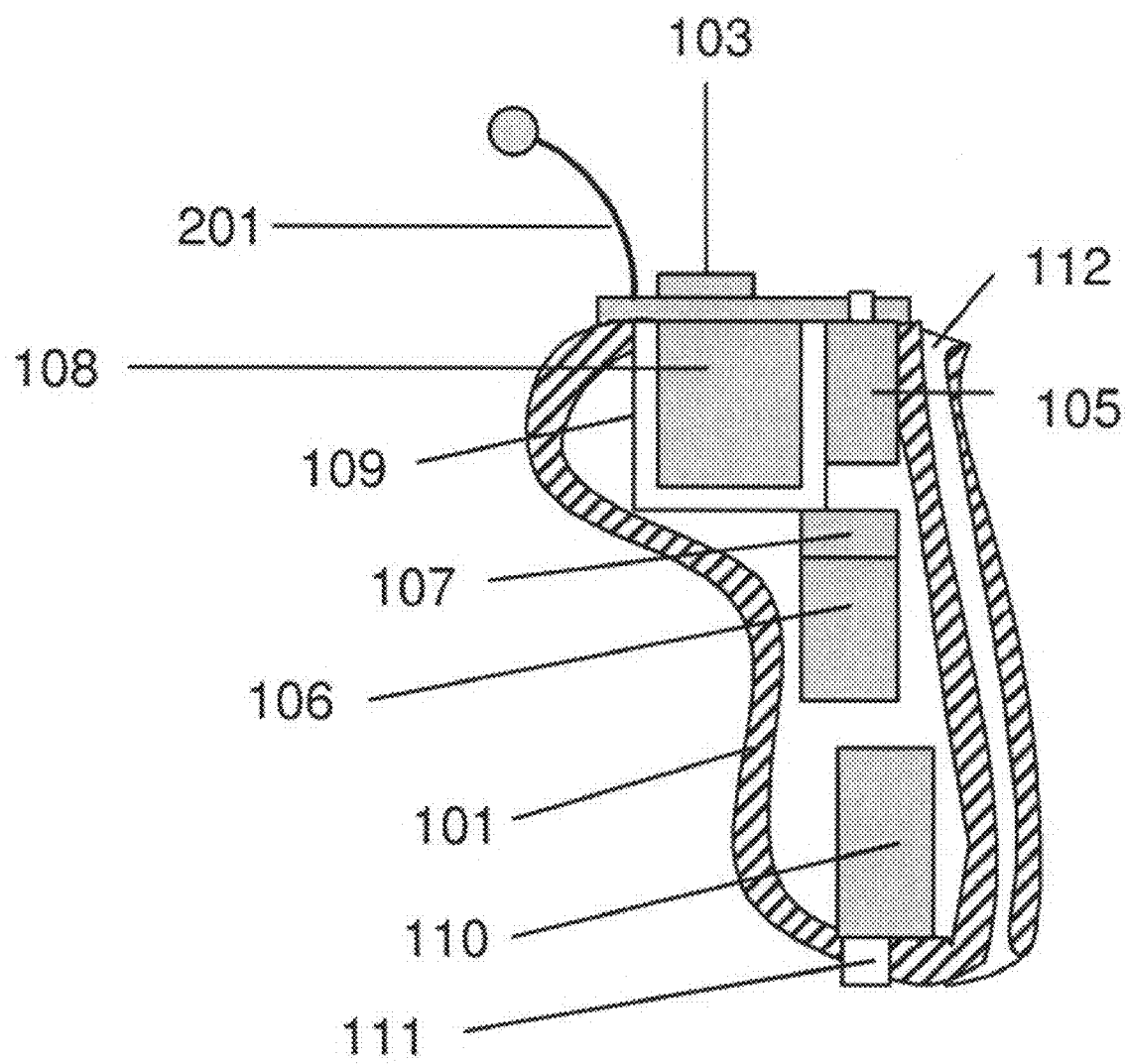
FIG. 2 shows a Completely-In-Canal Hearing Aid.
Figure 3:
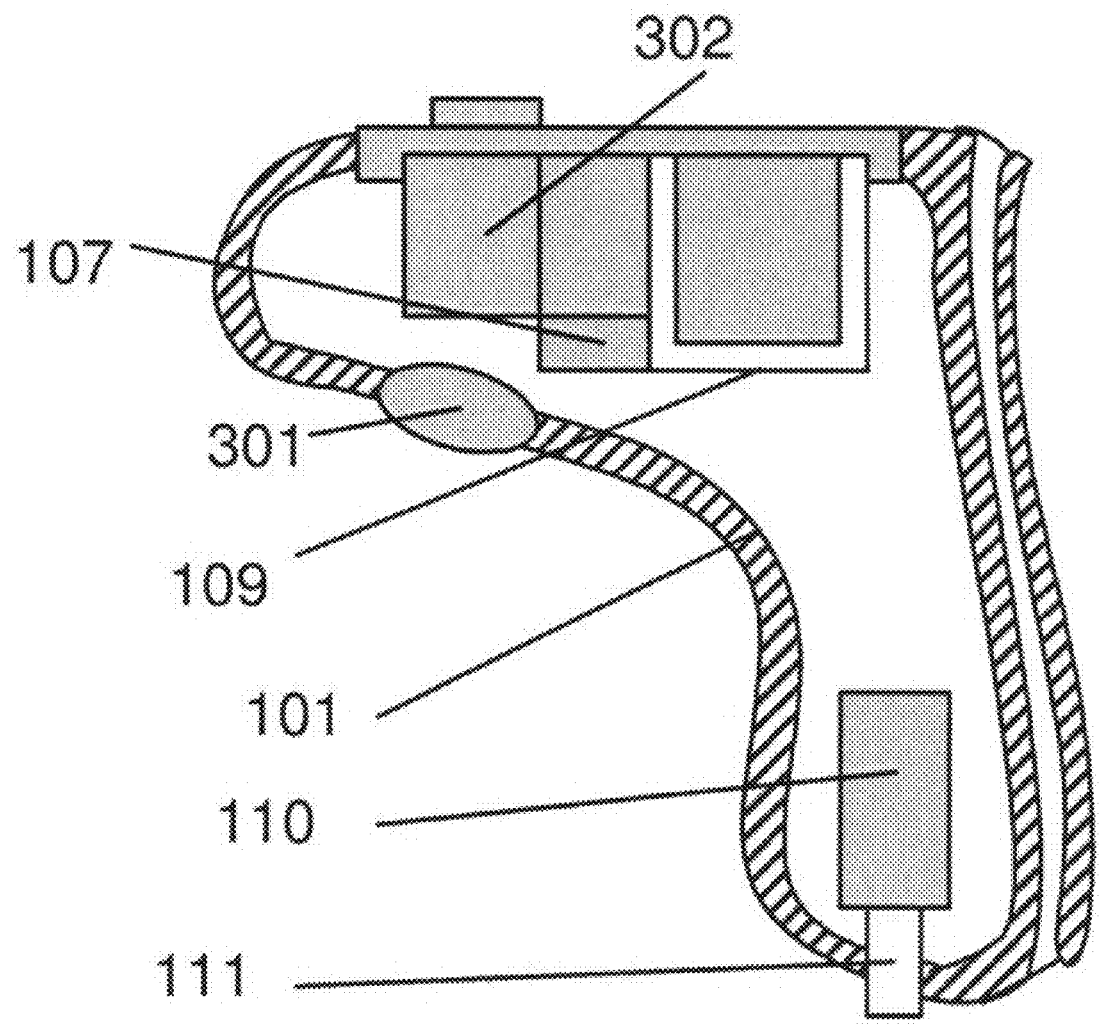
FIG. 3 shows a wireless In-The-Ear Communication device.
Figure 4:
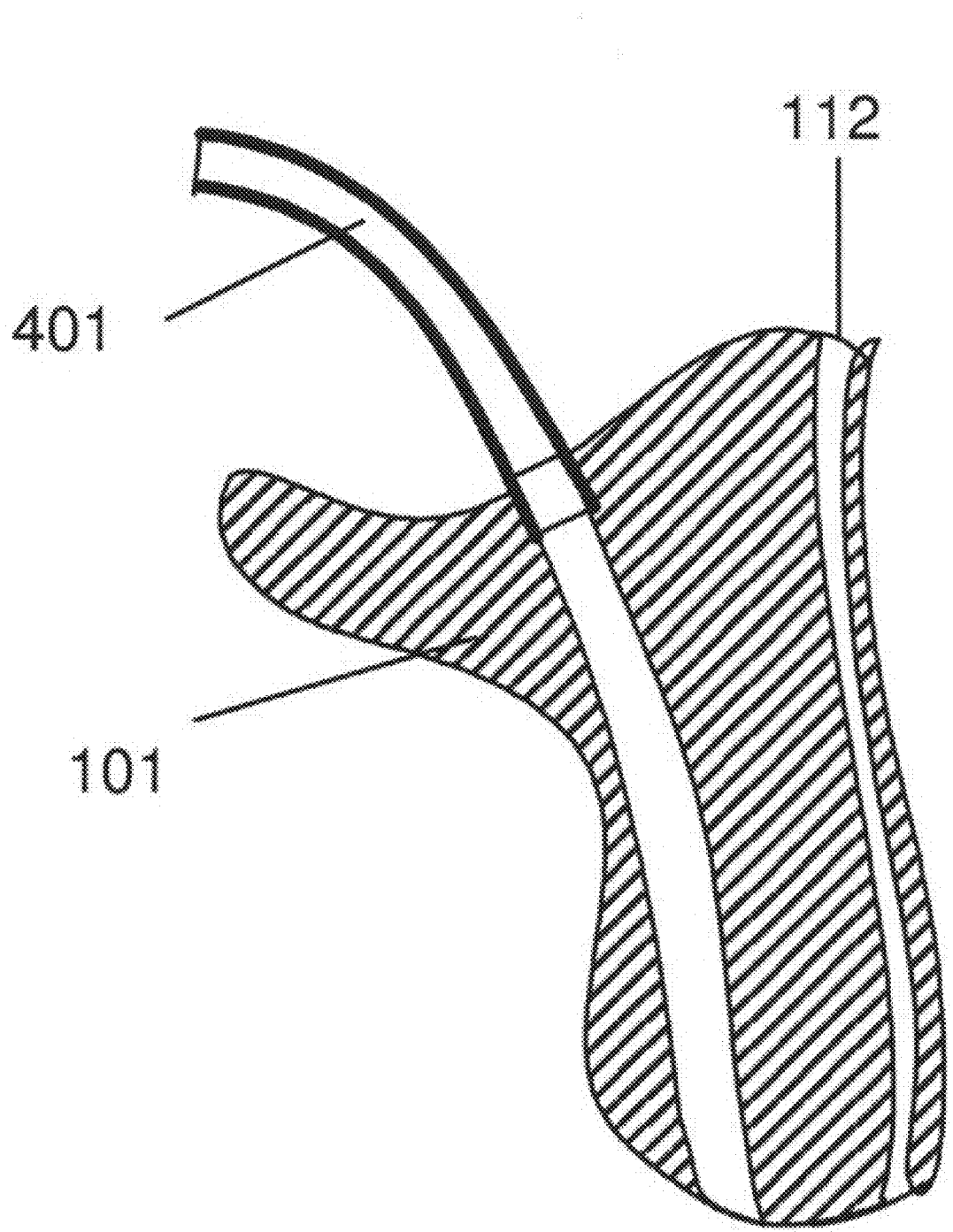
FIG. 4 shows an in-The-Ear Adaptive earpiece.

FIG. 1 schematically shows an In-The-Ear hearing aid, which typically consists of a shell or otoplasty 101 closed by a face or cover plate 102, a control switch 103, a sound inlet 104, a microphone 105, an electronic amplifier 106, a feedback control device 107, a replaceable battery 108, a battery compartment 1069, an transducer 110, a sound outlet 111 and a ventilation channel 112. FIG. 2 shows the smaller Completely-In-Canal hearing aid, which consist of the same components with an additional removal handle 201. Another example of a device worn in the ear is the wireless communication device in FIG. 3, which typically consists of a large number of similar components as the hearing aids and an additional microphone with vibration pickup 301 and a wireless transmitter 302. Finally is shown a simple adaptive earpiece in FIG. 4, which typically consists of a shell 101, a ventilation channel 112 and a sound tube 401.

Figure 5:
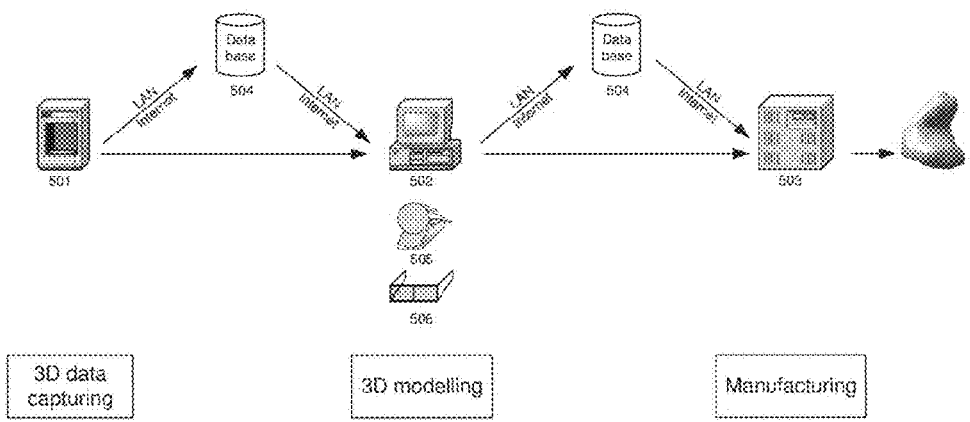
FIG. 5 gives an overview of a full process and the hardware components.

FIG. 5 shows an overview of the full process for manufacturing of customised earpieces and the involved hardware. The hardware comprises a 3D scanning device 501, a computer 502 and rapid prototype machine 503. Additional hardware devices are a database server 504, a spaceball tracking device 505 and 3D stereo glasses 506. The process consists of three main steps: 3D data capturing, 3D modelling and 3D manufacturing. As indicated in FIG. 5 3D data capturing. 3D modelling and 3D manufacturing can be performed at different physical locations to optimise cost and quality. Distribution is easily implemented, since the invention allows the original and final model to be transferred over the Internet. In general the invention is mainly focused on the modelling part. The individual operations will be described in details below.

The optimal output of the system varies from application to application and must initially be specified by human interaction or intelligent suggestions from a computer. In the case of hearing aids, ear worn communication devices and other mechanical or electrical devices worn in the ear, the goal is usually to optimise the size, the visual appearance, the acoustic properties and the placement of the components inside the earpiece. A perfect fit to the users ear is always wished for.

The system is implemented in two steps: initially the system requires input from an operator, and after a learning/training period the system may become fully or almost fully automated and may handle all steps with no or very little operator interaction. Manufacturers may get the system after the training has been performed to the specific application and may thus need virtually no human interaction to produce the desired result.

Often a quality assuring person or the user will judge the final earpiece and apparatus before it is physically produced by the system.

1.3 3D Data Capturing

Figure 6:
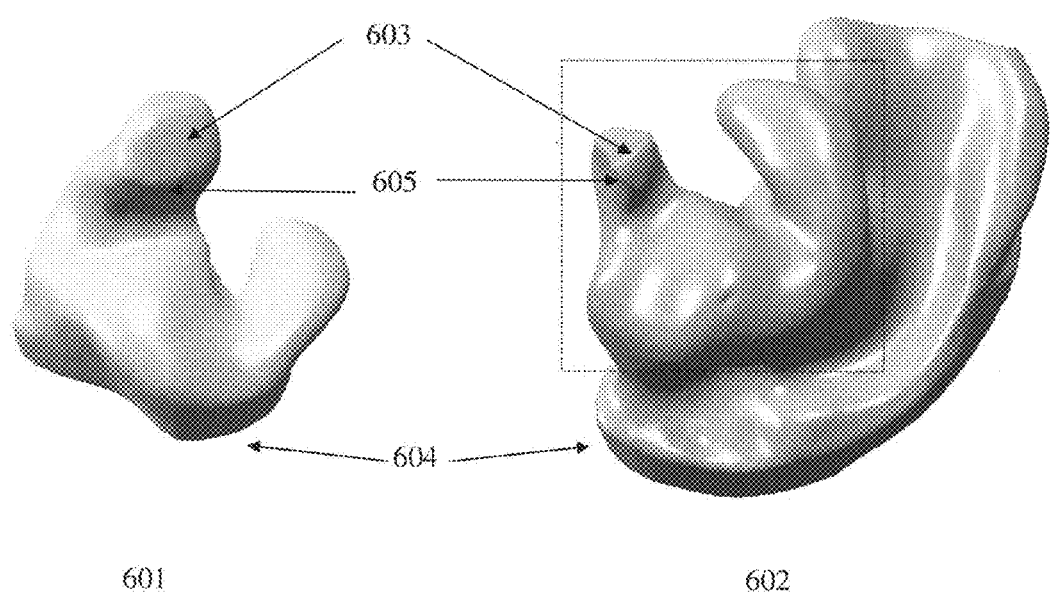
FIG. 6 shows two original 3D models of two impressions.
Figure 7:
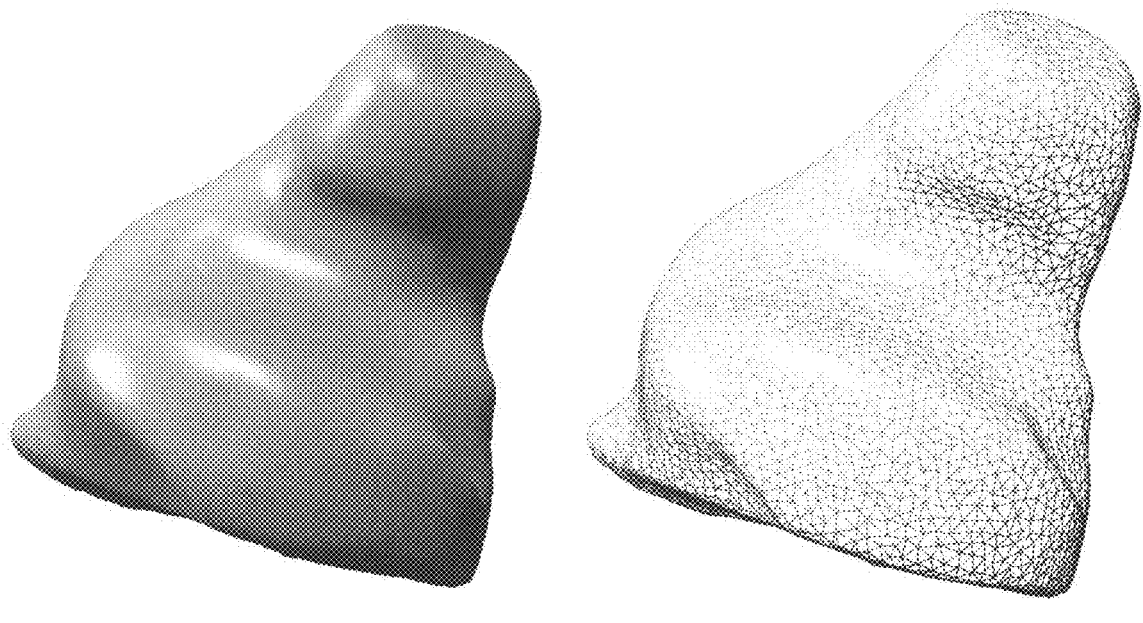
FIG. 7 gives an illustration of triangular based representation with the same 3D model visualized as shaded and as wire frame.

The first step in the production process is to capture a 3D digital model of the impression or directly of the auditory canal using a 3D scanning device. Two examples of original 3D models 601, 602 are illustrated in FIG. 6. Note that the medium size model 601 only corresponds to the part of the large model 602, which is marked by a box. Note also the definition of the canal part of the surface 603, the visible part 604 of the surface and which part that corresponds to the auditory canal 605. Different types of representations of 3D models exist. FIG. 7 illustrates the very common triangular-based representation, where the 3D model surface 701 is parameterised by a number of vertices, which are connected by triangles 702.

The preferred embodiment of a 3D scanning apparatus for the given application is a non-contact system. The 3D scanning device is typically based on the projection of one or more sheets of light or another known pattern of light onto an impression of the ear. The source of illumination is typically a low-power laser in the visibly light spectrum. Non-visible wavelengths can be used but this requires a sensor that can capture in the given spectrum. Non-contact 3D scanning of an ear impression can also be done using ultrasound, magnetic resonance or computer tomography (CT) scanners.

3D optical scanners capture series of profiles or another known pattern of light from the illuminated auditory canal-impression. Most often the light pattern on the object is one or more distinct lines. These profile-lines are digitised in real time by an optical sensor. When the ear impression or the optics are moved, other profiles become available. With continuous motion, the 3D scanner automatically digitises object profiles from multiple views. Some 3D scanners can digitise an object's profile as dense as every 0.01 mm, which results in a highly detailed digital representation of the object being scanned. The ear impressions are preferably placed on fixtures and automatically fed to the scanner. One example of a suitable scanning apparatus and method is disclosed in PCT/DK01/00564 (3Shape).

3D scanners that do not require an impression of the ear can also be used in the present invention. These are using a probe that is directly inserted into the ear. The preferred probes do not touch the ear-canal during the scanning process. The preferred probes either work by the use of ultrasound (WO 00/34739 Fagan et al.) or preferably the projection of a known light-pattern onto the auditory canal (PCT/DK01/00561, 3Shape).

The 3D scanner may also capture the texture of the impression. Capturing the texture can facilitate that text and marks can be drawn directly on the impression by the user or audiologist and read by the system or operator during modelling. This enables e.g. the user to mark areas, which causes pain or special visual requirements. Marks and text can be extracted directly from the texture images using classic image processing operations such as adaptive threshold or edge detection. The extracted information can then be projected onto the model and processed, e.g. areas marked for causing pain can be projected onto the model and material can be removed in the corresponding area.

Other examples of information that can be marked on the impression include: marking of an arrangement of a cutting curve/surface; marking of an arrangement of the vent or exits for vent(s); marking of identification tag (name or identity of the user or audiologist); marking of soft and hard areas of the auditory canal; marking of an arrangement of components; marking of the arrangement of features of the outer ear. It is to be understood that when several different features are marked, these can be marked in different colour, which can be distinguished by the texture scan. Text writing can be recognised by OCR during the modelling.

The captured 3D model may be saved in a database available in a local area network or over the Internet.

1.4 3D Modelling

Figure 8:
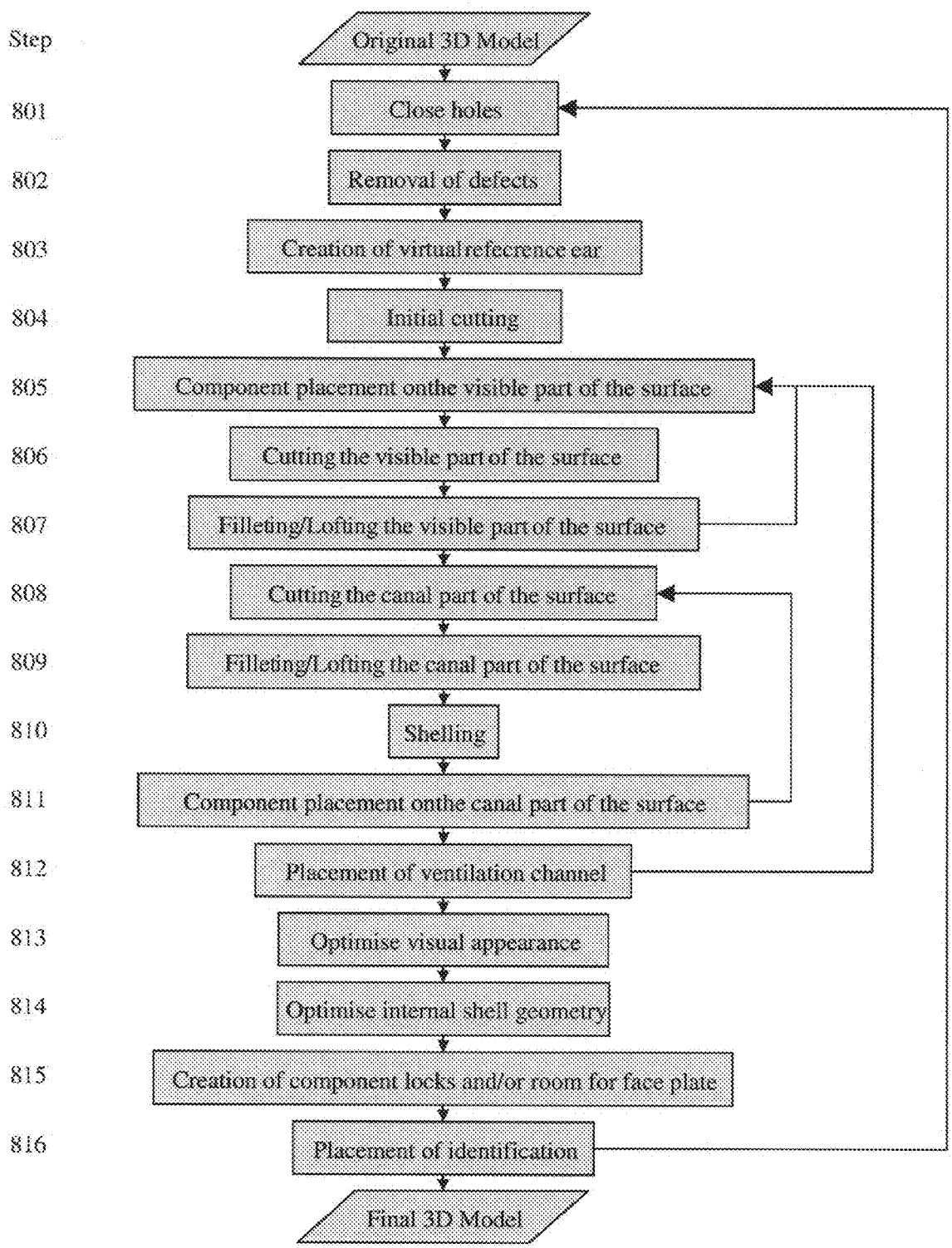
FIG. 8 shows a simplified example of a modelling process and the involved modelling operations.
Figure 9:
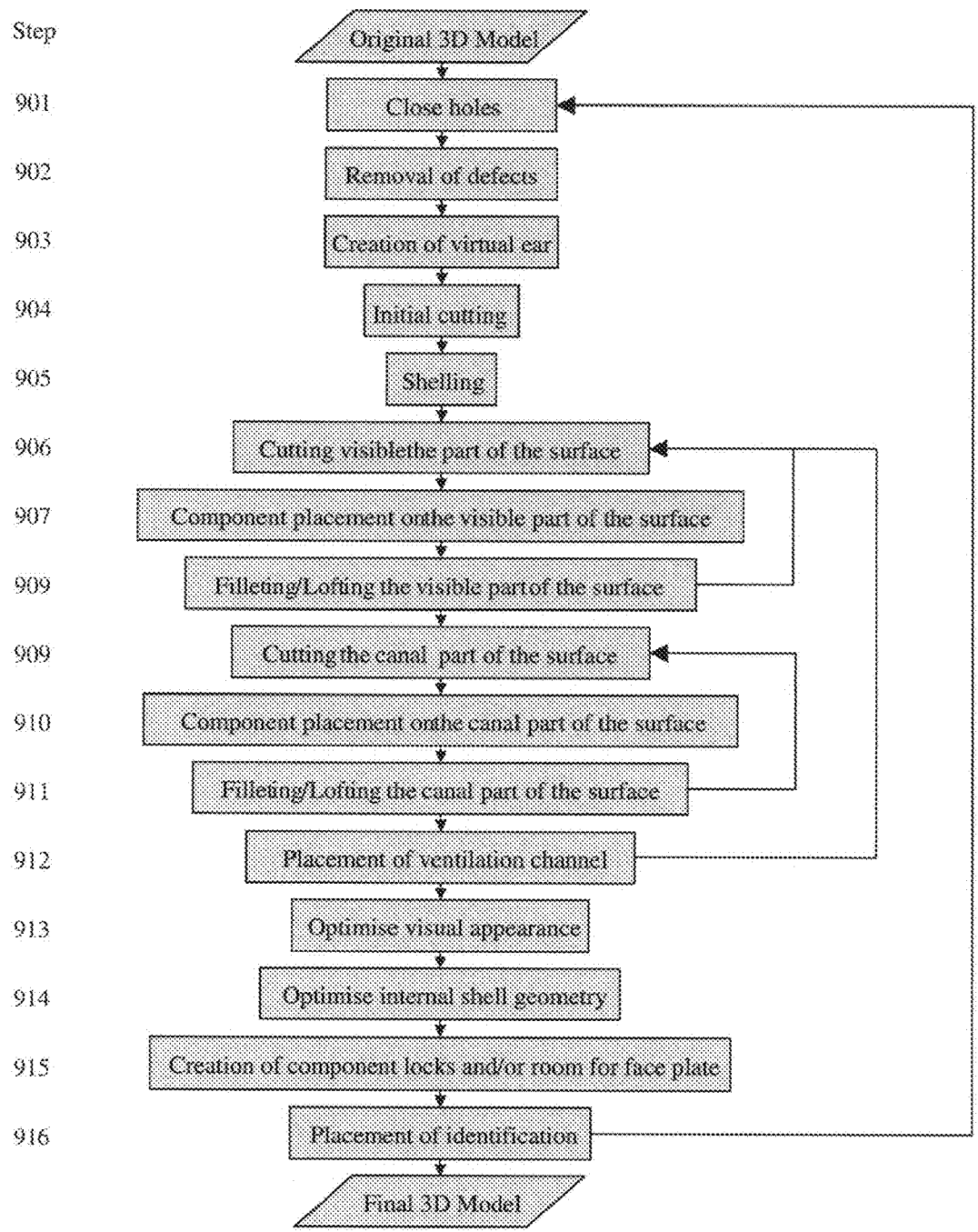
FIG. 9 shows a simplified example of a modelling process and the involved modelling operations.
Figure 10:
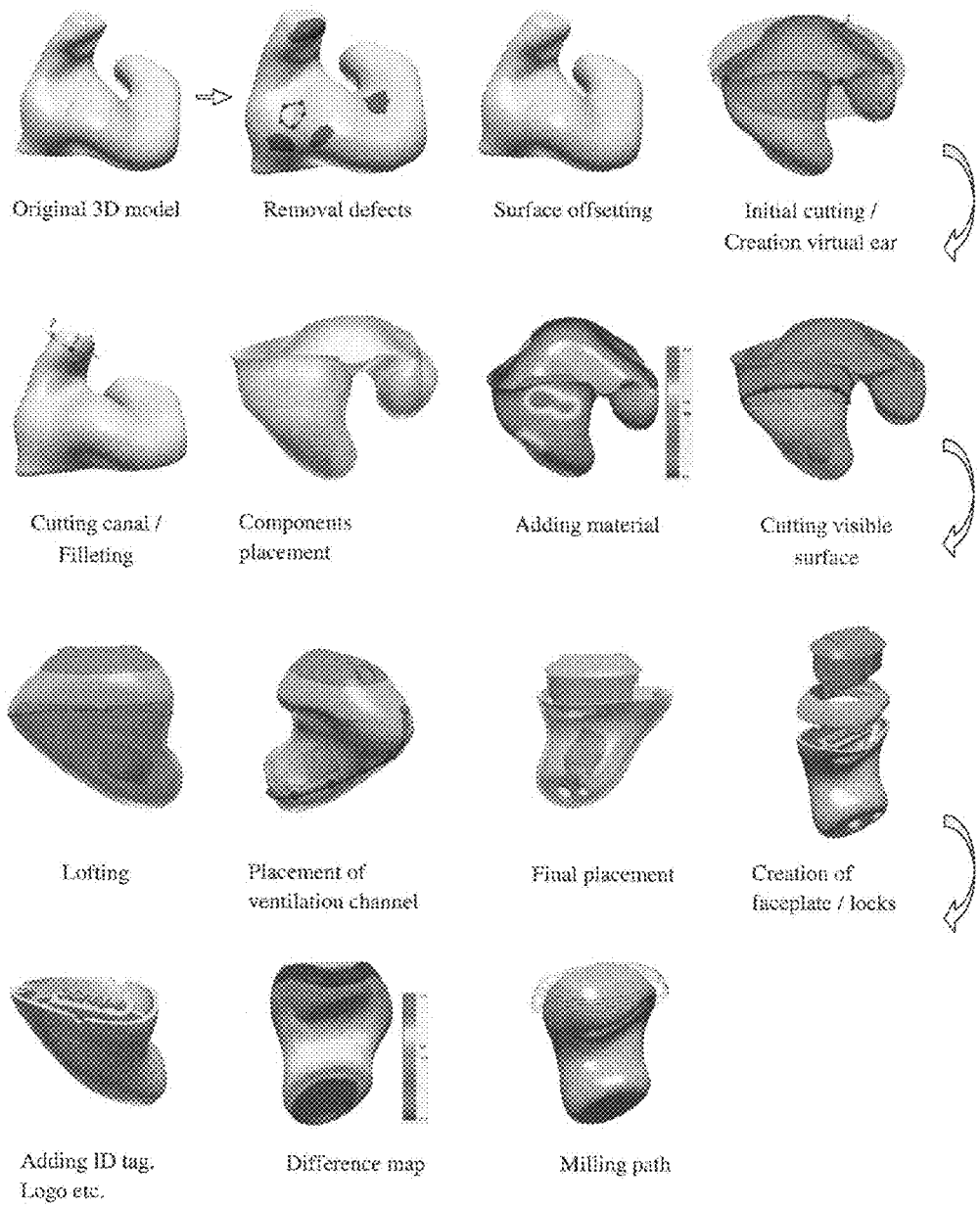
FIG. 10 shows a simplified example of the modelling process illustrated by images of the evolution of the model.

FIG. 10 shows a simplified version of the modelling process illustrated with the evolution of the present model during the modelling. FIG. 8 and FIG. 9 show two examples of the operations, which may be involved in the modelling process. The modelling operations 801-816 and 901-916 performed to create the final 3D model given the original 3D model are described in details below. Three examples are included to show that the individual steps are not necessarily performed in the order described but can be performed in a number of different sequences with an equally satisfying result Different orders have different advantages. The system can also try the steps in a randomised order to iterate towards the best solution. Note that the modelling process usually is an iterative process, where different properties e.g. the positions of components or the path of the ventilation channel are changed a number of times until a satisfying result is obtained.

The automation of the modelling software may be done using two-approaches that can either complement each other or work single-handed; During the automated steps the system can, at any time, request the input from an operator or switch to the other automation approach Similarity-Based Approach One approach used to automate the system is to extract the necessary modelling information from a database. This database contains original 3D models of the auditory meatus and canal from different persons. For each original 3D model all operations and settings used to create an optimal final 3D model are recorded. When a new model needs to be processed the most similar model is extracted from the database. Given the most similar 3D model, the computer software repeats the same sequence of operations that were performed on the extracted model in order to obtain the desired final 3D model. For successful use of the operations a registration, i.e. an alignment, of the new model to the extracted model may, be performed. Details on the extraction of the most similar model are given in section 1.4.18. Some operations and settings may need to be adjusted to compensate for different position, orientation and size between the two models.

Most ear canals of a person are to a large extent a mirrored version of the opposite canal. A variant of the similarity-based approach is to apply the operations and settings for an already modelled ear to the opposite ear, i.e. apply the used operations and settings for the left ear to the right ear of the same person. The only difference is that the first ear and the applied operations and settings need to be mirrored, before it can be applied. The mirroring of the ear can be performed by mirroring the vertices in an arbitrary plane since the actual plane only changes orientation and position of the mirrored model. Likewise the operations and settings need to be mirrored in the same plane.

Rule-Based Approach

The other approach incorporated in the system is to define a set of mathematical rules and implement these into algorithms that optimise the results of the individual steps in the modelling process. The optimal result of the individual operations takes into consideration the overall use of the final apparatus. The purpose varies with the application of the device.

1.4.1 Closing of Holes

Many scanning devices create original models with holes in the surface, i.e. the model surface is not closed. Models with uniclosed surfaces cannot exist from a physical point of view, so the holes need to be closed, due to e.g. occlusion effects. In a triangular-based representation holes are determined by counting the number of triangles at each edge. The edge corresponds to a boundary if only one triangle is present on the edge. Boundary edges always create loops defining the hole in the surface.

Triangulation of Hole

In the case of triangular-based representation the following approach is preferably applied to close each hole. If the hole is small, e.g. defined by the boundary length, a triangulation is performed by directly connecting the vertices on the boundary by non-intersecting triangles. The triangulation is performed using a standard 3D triangulation method such as proposed by Hoppe et al. in "Surface Reconstruction from unorganised points", Computer Graphics, 26(2), 1992, pp. 71-78.

Preferably the first step in closing large holes is to perform a fit of a parametric surface to the vertices on the boundary of the hole and the vertices in its neighbourhood. The parametric surface should preferably be smooth such as a $2^{nd}$, $3^{rd}$ or lower order surface, a NURBS surface or another type of spline surface. The neighbourhood may be manually marked or defined as the vertices in a certain distance from the boundary. To triangulate large holes new vertices are sampled on the fitted surface. These sampled vertices are then connected by triangles. One method for performing this operation is described in 1.4.7. The triangulated hole can be smoothed (see section 1.4.12) to improve visual appearance.

1.4.2 Removal of Defects

Figure 11:
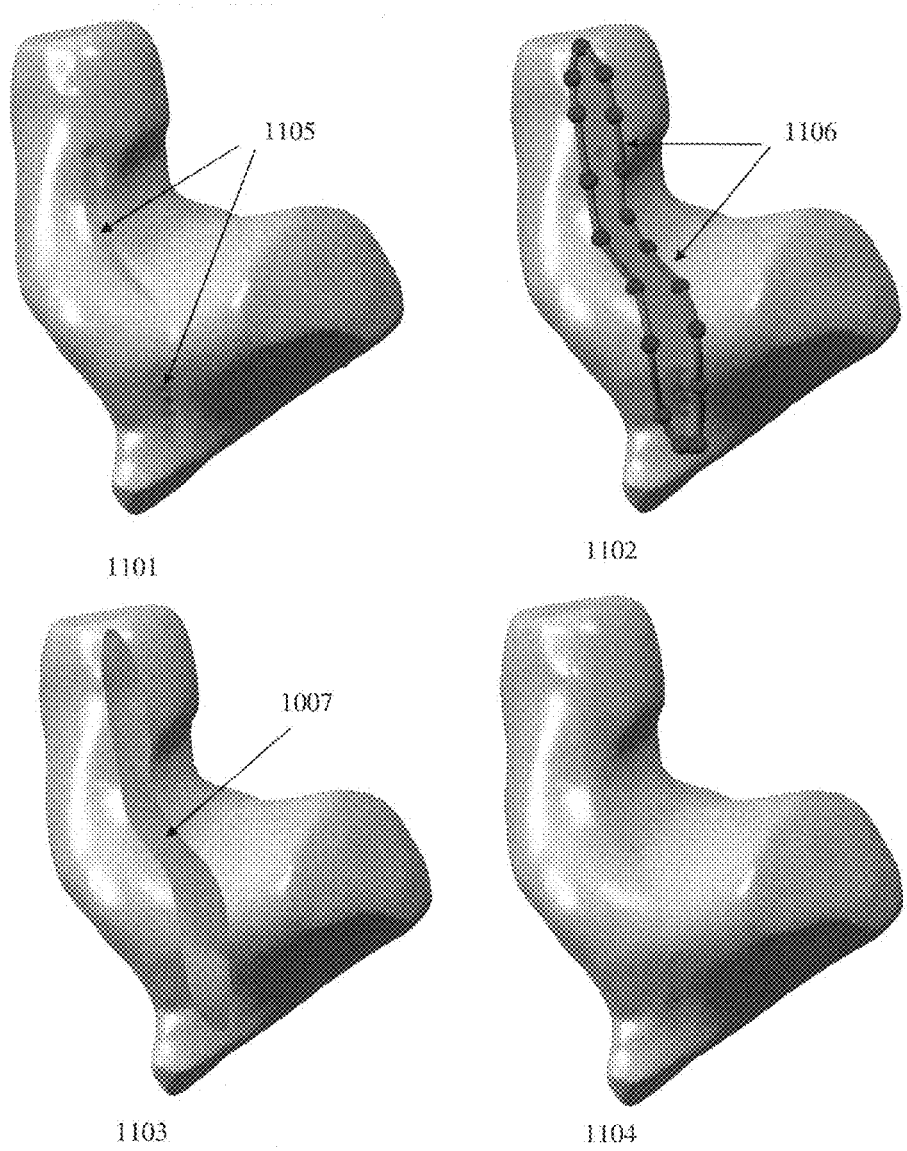
FIG. 11 illustrates a removal of a defects related to a thread, which are used to remove the impression from the ear.

A number of defects and artefacts are often present in the original impression and hence in the original 3D model These defects originate from a number of different sources such as the impression creation, scars, tissue or hair in the ear, the thread used to remove the impression from the ear or small scratches and cuts from the handling. FIG. 11 shows defects 1105 originating from the thread. Other artefacts, such as bents on the ear channel, also need to be removed to obtain an earpiece, which is pleasant to use.

Manual-Based Approach

To remove defects the area containing the defects may be marked using a proper selection tool. The choice of selection depends on the shape of the defect. A number of selection tools can be used based on point selections, rectangular selection, circle selections, brush selections, semi-coplanar selection, flood selections, edge selections, rim selections and selections along a curve defined by a number of control points.

In the case of the removal of the thread defect a curve-based selection 1106 is usually preferable and the thread is marked by placing a number of points along the defect. To remove the defect the marked triangles are removed and the hole 1007 is closed following section 1.4.1. Figure it shows the input model 1101, the selection of the defect 1102, the hole to close 1103 and the model 1104 with the defect removed.

Other defects or artefacts are removed in a similar fashion, whereby the defect or artefact is marked and removed followed by a closing of the hole (see section 1.4.1).

Rule-Based Approach

The ear surface may be characterized by a soft and smooth surface. In contrast, defects may be characterized by sudden changes in the surfaces, which can be viewed as holes, valleys, peaks or ridges in the surface. These differences can be applied to detect defects.

In practice the local curvature can be calculated in each vertex. Areas containing defects are characterized by a high local variation in curvature. The local variation of the curvature in a vertex is calculated as the variance of the curvature in the vertices in the neighbourhood, e.g. first order neighbourhood. If the local curvature variation exceeds a predefined threshold a defect is assumed to be present The rest of the defect is traced by recursively including all, neighbouring vertices with a local curvature variation above the defined threshold. When the full defect has been traced, the included vertices and their corresponding triangles are removed and the hole is closed in the same manner as described in the manual approach.

1.4.3 Creation of Virtual Reference Ear

Figure 12:
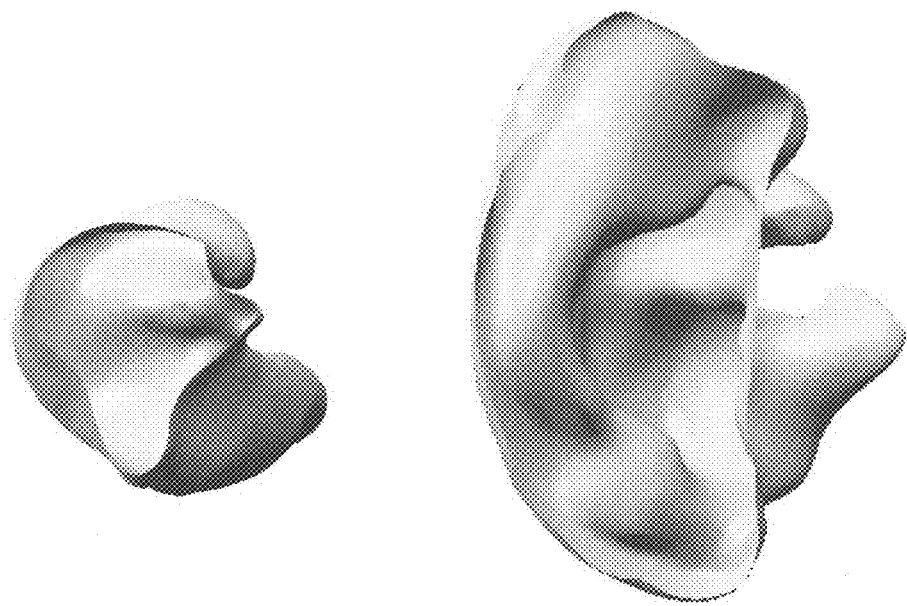
FIG. 12 illustrates two simple virtual reference ear models created from the corresponding models shown in FIG. 6.

A powerful tool for creation of visually appealing earpieces is to generate a virtual reference ear model. A simple virtual reference ear model is illustrated in FIG. 12. Given a 3D ear model the present and final appearance of the earpiece can be visualized and the operator and user obtains a improved imagination of the effect of changing different properties, e.g. shape, size, colour, texture or components. The virtual reference ear also plays an important role in the automated cutting and placement of components. As a part of the creation of the virtual ear a coordinate system may also be inserted. The XY-plane in the coordinates system may be defined along the cheek with the Y-axis parallel with the body. The Z-axis should point into the ear cannel.

Manual Approach

A simple virtual reference ear may be obtained by cutting the original model by a single surface such as a plane. Detailed descriptions of the cutting tools are found in section 1.4.4. The ear model in FIG. 12 is created by a planar cut of the model in FIG. 6. To obtain the most realistic impression of an ear the cut may be performed by a surface, which is parallel with the cheek. In the case of manual interaction the operator interactively defines the cutting surface by a number of control points on the surface of the original model. The number of control points required depends on the number of free parameters in the surface. In the case of a plane three points are required. Usually the XY-plane in the coordinate system is determined directly from the surface. However, two extra points need to be selected to determine the X-axis and the origo/Z-axis.

Similarity-Based Approach

In an automated scheme the cutting surface can be obtained as the surface applied to the most similar model, which has been extracted from the database. The coordinate system is determined in a similar way.

Rule-Based Approach

An alternative automated strategy is to extract features, primarily lower order moments. These features are then fed to a neural network or another type of parametric or non-parametric model, which outputs the most likely plane. Such type of approach requires a training set, which can be applied to train the neural network. The coordinate system is determined in a similar way, but with a separate neural network.

An ear model only created from the original 3D model is limited to the size of this model. A larger model of the full ear or ideally the full head is desirable for optimal visualization of the visual appearance of the apparatus. Until full and precise 3D models of the human head become easily accessible, an ear or head model, which is locally similar to the original model (a so-called dummy head), can be extracted from a database. The extracted model can be merged with the original model and an improved visualization can be obtained. Another option is that a device, which captures the model directly without the use of impression, may capture the full geometry and texture of the ear and/or the head simultaneously.

1.4.4 Cutting

Figure 13:
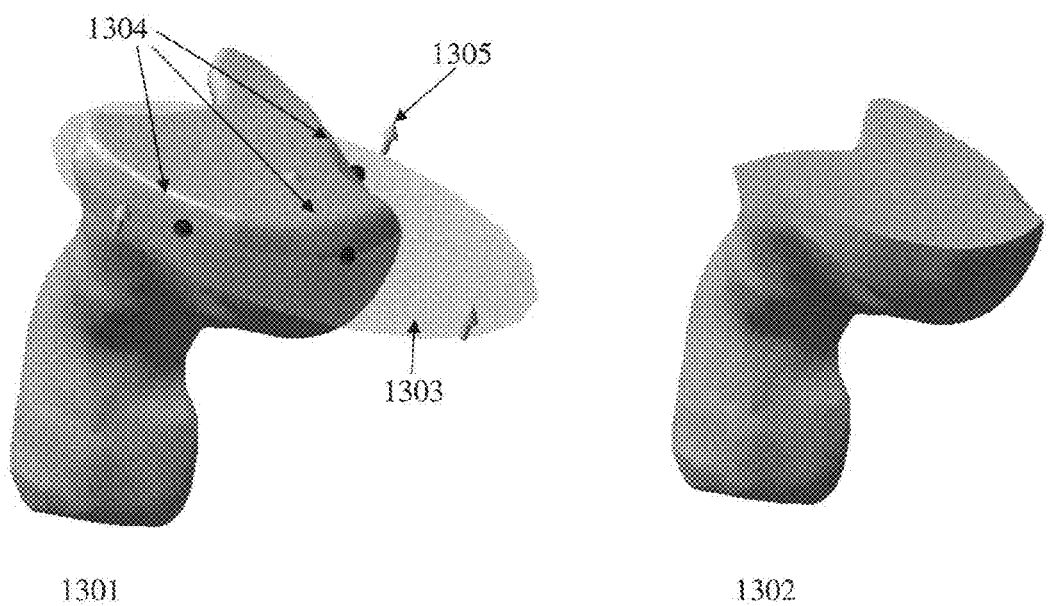
FIG. 13 shows a 3D model before and after cutting and closing by a simple planar surface defined by control points and a surface orientation.

One of the first steps in the modification of the original model is usually to perform one or more cuts. FIG. 13 shows a model before 1301 and after 1302 a cut with a single planar surface 1303 controlled by three control points 1304. The surface orientation 1305 defines what part of the model to remove. Finally the hole generated by the cut is closed by the surface.

Cutting by a Single-Surface

Given an arbitrary surface, $f(x, y, z)=0$, the cutting is performed by removing all parts of the present model, which are above/outside this surface, $f(x, y, z)>0$. To actually perform the cut, all intersections between the model and the surfaces need to be determined and a cut is performed along these intersections.

Figure 14:
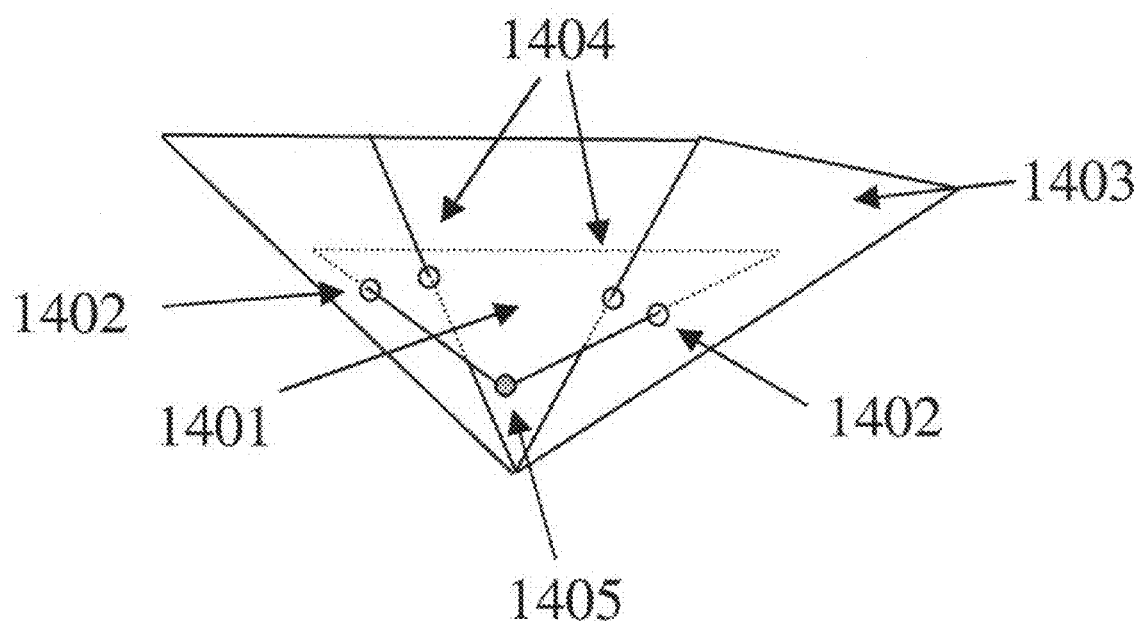
FIG. 14 illustrates intersections between one model triangle and the surface triangles in a triangular-based representation of a 3D model.

In a triangle-based representation a triangular version of the surface is assumed to be present. The first step is to remove the triangles with all vertices above the surface. The next step is to determine the intersecting triangles in the two models, see FIG. 14. For each intersecting triangle 1401 in the model the points corresponding to the intersections 1402 between the edges of this triangle and the surface triangles 1403 are determined. The possible intersection between an edge and the triangle may be determined using Badouel's algorithm (Badouel, D. "An efficient Ray-Polygon intersection", Graphic Gems, pp. 390-393, 1990). Likewise, the intersection points 1404 between this triangle and the edges of the surface triangles are determined. Together with the vertices 1405 of this triangle, which are below the surface, these intersection points form a closed loop of points. By a triangulation of this loop the proper boundary of the surface cut is created for this particular triangle. All the points/vertices in the loop lie in the plane of the triangles which limits the triangulation to two dimensions. Applying a standard 2D triangulation algorithm such as Delauney triangulation closes the hole. However, Delauney triangulation produces a triangulation of the convex hole, so the triangles outside the loop need to be removed (or never created).

Repeating this procedure for each intersecting triangle in the model creates an output model, which has been cut by a surface. Note that all triangles with all vertices below/inside the surface are left untouched. Refer to section 1.4.5 for details on how to reduce the number of triangle intersection tests by a subdivision of the space into cubes.

Cutting by a Curve on the Surface

As an alternative to cutting by surfaces the cutting can be performed by a curve. FIG. 22 shows the model before 2201 and after 2202 cutting by a spline curve 2203 defined on the surface of the model. The curve 2203 is defined by a number of control points 2204, which always lie on the surface of the model. The control points and hence the curve can be manually adjusted by the operator. The orientation of the curve determines what part of, the model to remove, i.e. the part of the model that is inside the curve is removed. The curve may also be controlled by other means, than control points.

Figure 15:
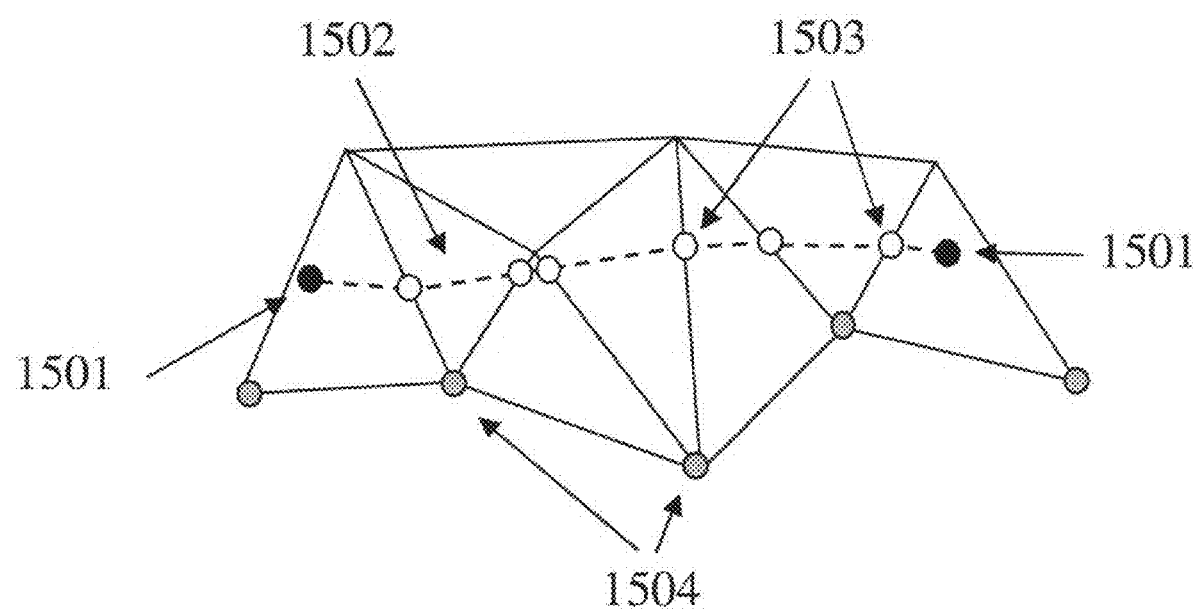
FIG. 15 shows the cutting of the triangles between two pointes sampled on a curve and projected onto the 3D model. The cutting is performed by a local cutting plane.

To actually perform the cutting an ordered number of points are sampled along the curve. The individual points are then projected onto the 3D model e.g. using the triangle normal in the previous projected point. The normal in the first point is known from the first control point. Given these projected points, $p_1, \ldots, p_n$ 1501 on the 3D model (see FIG. 15) the cutting is performed by cutting the individual triangles between $p_i$ and $p_{i+1}$, 1501 by a local plane cut 1502. The cutting is performed by traversing the intersection points 1503 between the triangle edges and the local cutting plane between $p_i$ and $p_{i+1}$. Following the previous section a triangulation is performed of each loop consisting of the intersection points in an intersected triangle and the triangle vertices 1504 below the cutting plane. The local cutting plane is defined by the point $p_i$ and the cross product of vector from $p_i$ to $p_{i+1}$, and the average triangle normals of the triangles, which $p_i$ and $P_{i+1}$, is projected onto. The result of cuffing by a curve is illustrated in FIG. 22.

Cuffing by a Single Surface and Closing the Hole

Usually models with closed surfaces are required; so the hole created by the surface cutting needs to be closed by the surface, i.e. the surface need to be cut along the intersections with the model and combined with the model The procedure is equivalent to the one applied when the model is cut by a surface. The only difference is that the interpretation of surface and model is swapped. In this case the loops to be triangulated are created for all intersecting triangles in the surface. Finally merging the pair of intersection points combines the surface and model, which has been cut, to form the output model. Note that there exists a one-to-one correspondence between all intersection points in the model and surface, which has been cut. An example of surface cutting and closing is shown in FIG. 13.

Cutting by a Surface with Thickness and Closing the Hole

Figure 16:
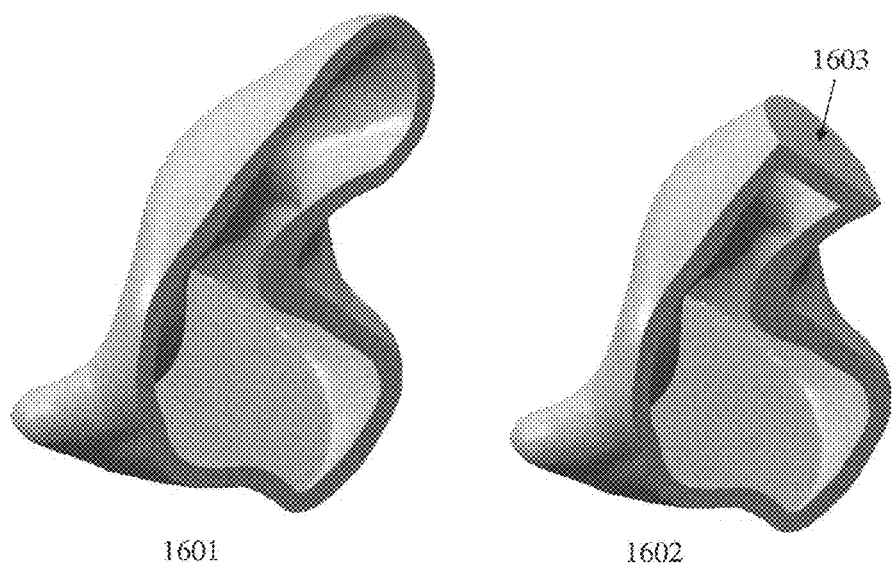
FIG. 16 illustrates cutting and closing of the top of a shelled model with a planar surface with thickness equal to the shell thickness.
Figure 26:
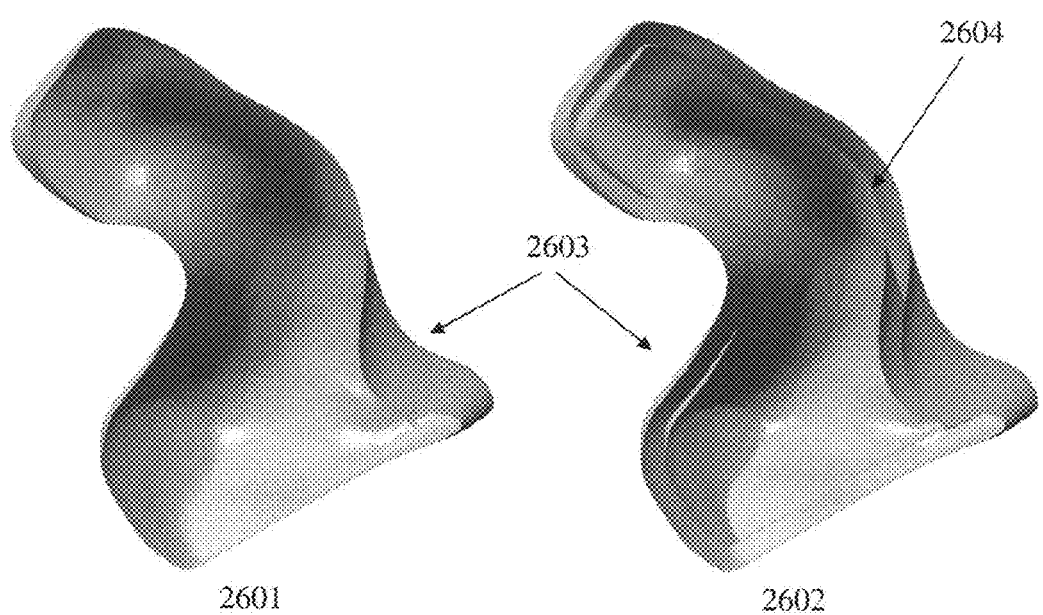
FIG. 26 illustrates the result of a shelling.

In the case of a model with a shell thickness the cutting surface needs to have a thickness if the final shell thickness should not be violated. A shelled model is shown in FIG. 26. Refer to section 1.4.9 for details on shelling. Cutting by a surface with thickness and global orientation solves the problem with final shell thickness. FIG. 16 shows a model before 1601 and after 1602 cutting by a surface 1603 with thickness. The global orientation of the surface determines what part of the model to remove.

Basically a surface with thickness comprises two non-intersecting independent single surfaces with opposite orientation and a constant or varying distance. The orientation of one of the single surfaces is equivalent to the global orientation. This single surface is defined as the outer single surface and the other as the inner single surface. Parts of the outer single surface correspond to, parts of the outer shell surface after the cutting, hence the name.

In practice the cutting of a shelled model by a surface with thickness may be performed as two independent cuts by the two single surfaces. The outer shell surface of the shelled model may be cut and closed by the outer single surface using the approach described in the previous section In a similar way the inner shell of the shelled model may be cut and closed by the inner single surface, see FIG. 16.

1.4.5 Component Placement on the Visible Part of the Surface

A very important operation for the visual appearance of the final earpiece is component placement on the visible part of the surface. The visible part of the surface is defined as the part of the surface, which is partly or fully visible, when the earpiece is inserted in the ear. The term components is not limited to traditional components such as electronics, buttons or battery devices, but can describe any type of units, functions or features of the earpiece, e.g. logo, surface patches or outlets connected to interior components. The placement Is restricted by a number of factors such as collision between components and other parts of the model (e.g. shell, ear and other components), room for other components (e.g. ventilation channel, amplifier, microphone, vibration pick-up, microchip, battery, and printed circuits), the angles of the components in the shell and the angles of the components with respect to the ear/head. The components are usually arranged in relation to a related component surface, which is then connected with the rest of the shell preferably by a cutting or loft operation. An alternative strategy is to create the component surface directly from the arranged components. The component surface is not necessarily an integrated part of the final 3D model. It could be a separate cover or faceplate, which is assembled with the shell later in the production process. FIG. 18 illustrates the arrangement of the component consisting of electronics and battery 1801 and the related component surface 1802.

Manual Approach

Figure 17:
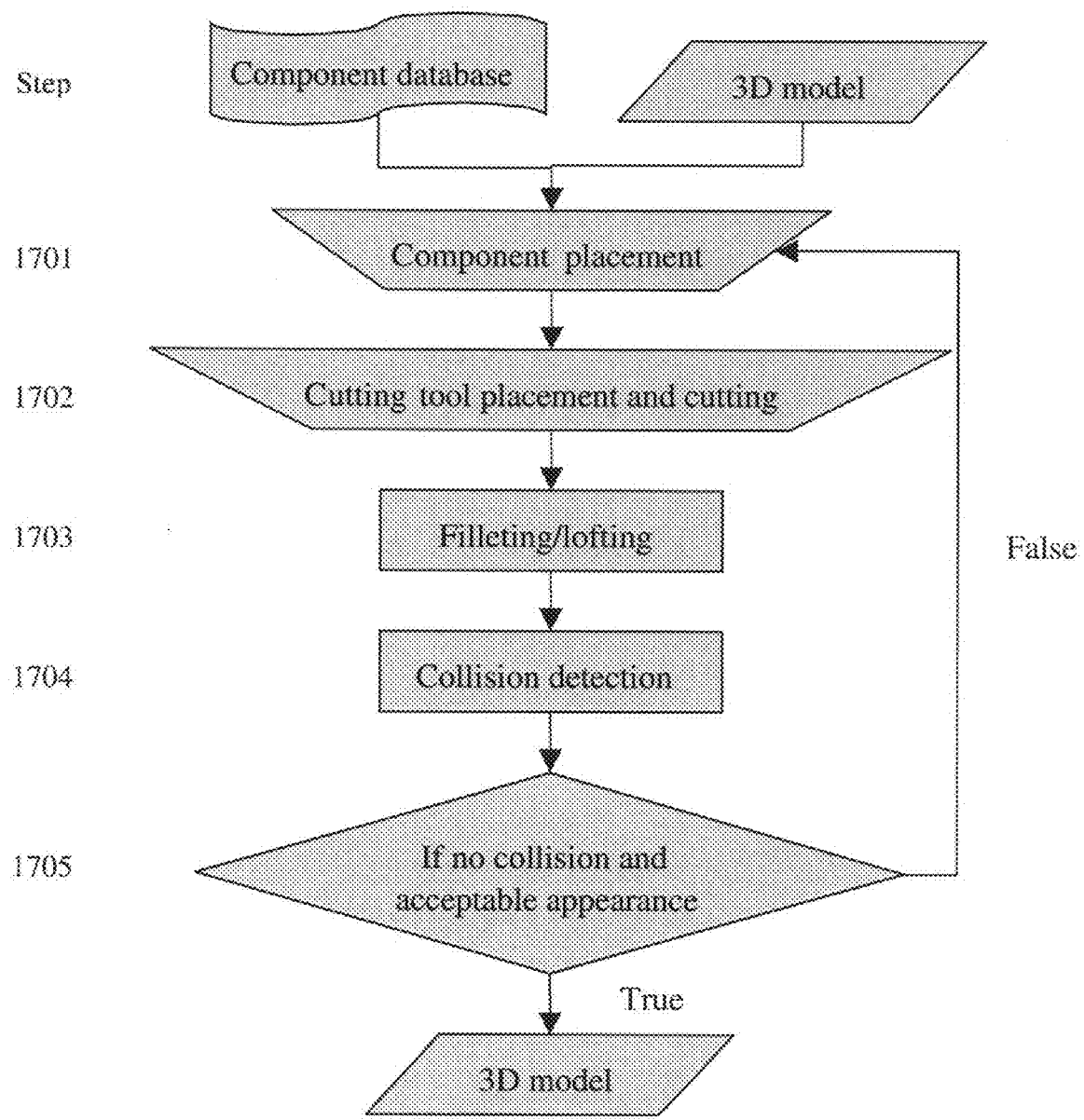
FIG. 17 show a flow chart for the loop used for a manual approach for the component placement, cutting and filleting/lofting of the visible part of the surface.

The flow chart of the manual approach for component placement and the closely related cutting and filleting/lofting operations is illustrated in FIG. 17. Note that this flow chart illustrates the order of the operations used in FIG. 8, but many different orders of the operations could be applied; see e.g. FIG. 9 or FIG. 10. It is assumed that the relevant component surface and components such as amplifier, microphone, vibration pick-up, volume control, microchip, battery and printed circuits, have been selected from the component database. Usually simplified CAD models of the components are applied to reduce the computation time. Depending on the type of component surface, the surface may also be an imported CAD model, e.g. a faceplate.

The first step in the manual component placement is usually the placement of the related component surface 1802 with respect to the 3D model. However the component surface can also be created directly from the arranged components. The selected components 1802 are then placed in relation to the 3D model and component surface by a manual arrangement of the component in the three dimensional space. The manual arrangement of the component surface and the components is usually an iterative process, where the position and orientation of the surface and components are alternately adjusted until an acceptable arrangement 1705 is obtained. The present state of the model is visualised in the virtual ear (see section 1.4.3) to improve the evaluation of the visual appearance. The visualisation of the ear and the shell can be made transparent to further facilitate the placement. Note that the parts of the components can be below, inside and above the component surface depending on the configuration.

Independent manual placement of component surface and the components is a cumbersome and error prone task. Two tools may improve the performance of this task significantly. The first tool is to place and lock the components in relation to the component surface. When the operator adjusts the component surface the components keep the relative position to the surface, but change the position with respect to the 3D model. The position of component and component surface may be temporally unlocked and the relative position of the components adjusted. In this it is often an advantage to restrict the component to stay on the surface.

Figure 19:
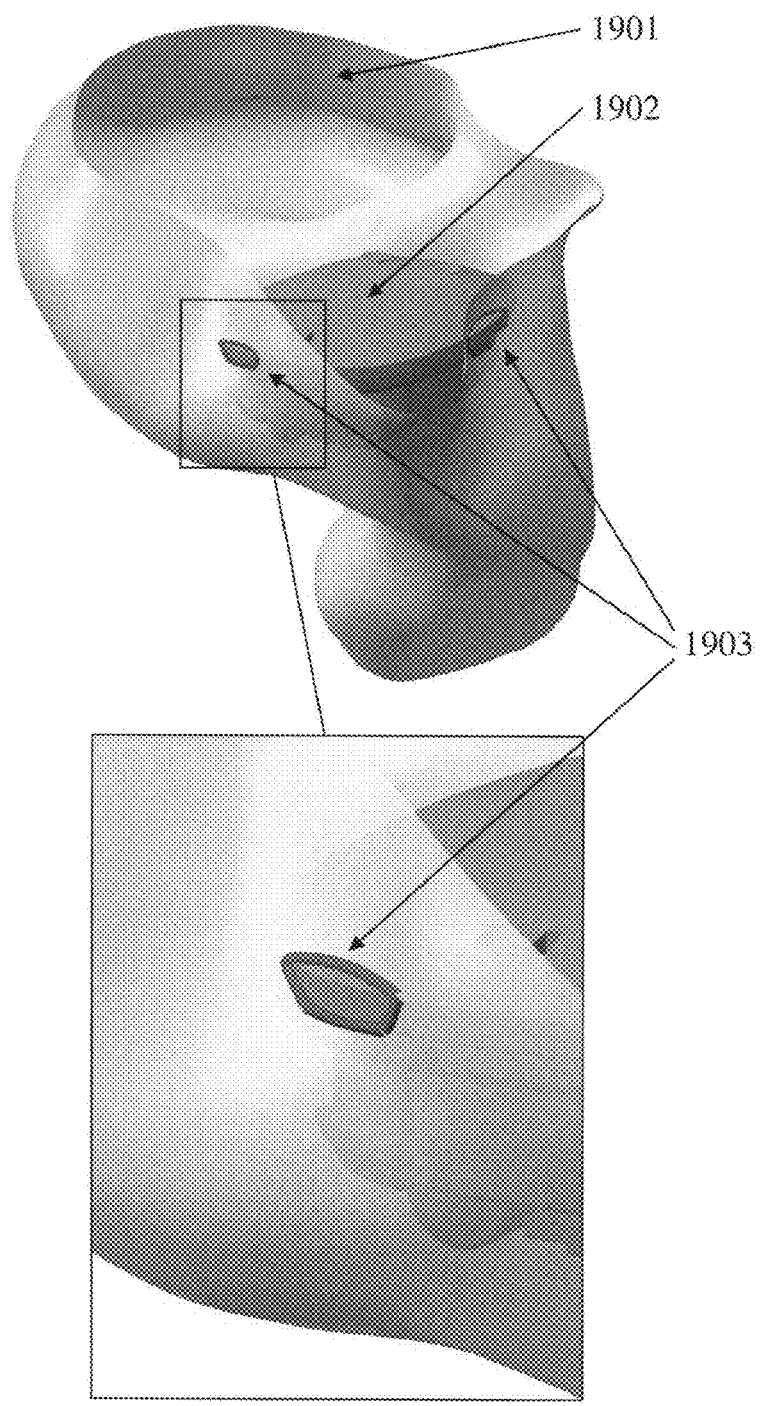
FIG. 19 shows an example of collision between component and shell surface.
Figure 20:
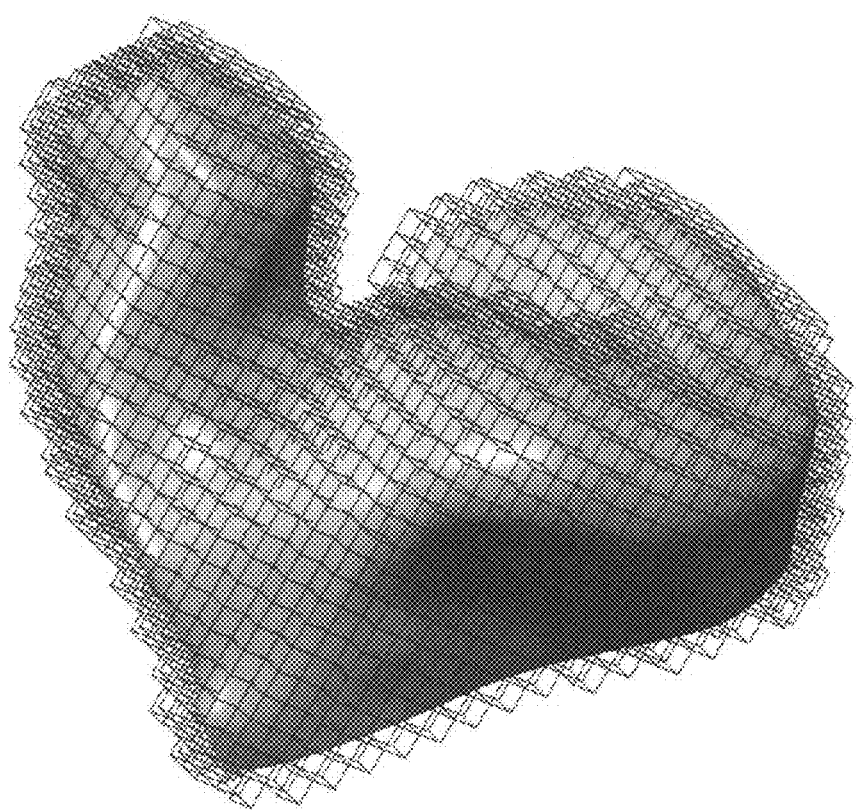
FIG. 20 illustrates a spatial division of the space into cubes.

The second tool is collision detection 1704, where a test is performed for collisions between the components and the relevant parts of the model. FIG. 19 illustrates the collisions 1903 between shell surface 1901 and the component 1902. Typically the collision detection is performed with respect to the virtual ear, other components and the part of the present shell, which has not been removed by the cutting. One approach, to collision detection is to perform a brute force test for intersections between the surface of the model and the component model. In a triangular-based representation the triangles in one model need to be tested for intersections with the triangles in the other model. An exhaustive intersection test between all triangles in the two models is very computational expensive. Note that real time collision detection is almost mandatory, if the tool should be attractive. To reduce the computation time and facilitate real time collision a spatial subdivision of the 3D space into cubes (Fujimoto et al., "Arts: Accelerated ray-tracing system", IEEE Computer Graphics and Applications, 6(4), pp. 16-14, 1986) is performed, see FIG. 20. Each cube holds a list of all the triangles, which have parts inside it.

Assume that the cube structure has been created for a model. If an intersection test needs to be performed between a new triangle and this model, only intersection tests between the new triangle and the triangles, which correspond to the cubes with parts of the new triangle inside, need to be performed. This method can be applied to perform a very fast test of all the triangles in one model with all relevant triangles in another model. Hence the full intersection test between the two models is performed. Based on the collision detection the penetration of one model into the other is determined. The 3D model used for collision detection may be an offset version of the original component to facilitate a minimum distance is not violated. The offset distance usually corresponds directly to the minimum distance.

Hierarchical collision detection may also be used to obtain low computation times, e.g. by the use of bounding volumes. Preferably the bounding volume should be spheres, axis-aligned bounding boxes, oriented bounding boxes, k-DOPs (discrete orientated polytopes), pie slices or spherical shells.

An alternative strategy to collision detection is to measure the local or global distance from the component surface to the relevant parts of the model. This type of collision detection has a large degree of freedom, since collision also is detected if the components violate a minimum distance to the relevant parts of the model. This is very relevant in the case of required collision detection with respect to the inner shell surface, before the surface is actually created.

In the case where there is not enough space for the components the shell may be modified in the collision regions to make more room. One way of doing this is to remove material from the shell using a Boolean function, such as subtracting the colliding part of the component from the shell, provided that the component does not penetrate the shell. Another option is to use an iterative offset, which Is repeated until room enough has been created for the component—again with the constraint that the component should not penetrate the shell.

Refer to section 1.4.17 for details on how to add and remove material. Modifying the shell outwardly will make the final model intersect with the ear. However this may be a minor problem for limited modifications, especially if these are performed in the soft parts of the ear.

Similarity-Based Approach

Extracting the most similar model and applying the same position and orientation of the component and the related component surface can automate the placement of the surface and the components. The collision detection presented above can be applied to ensure that no collisions are present. If collisions exist one of the other approaches can be applied.

Rule-Based Approach

Figure 21:
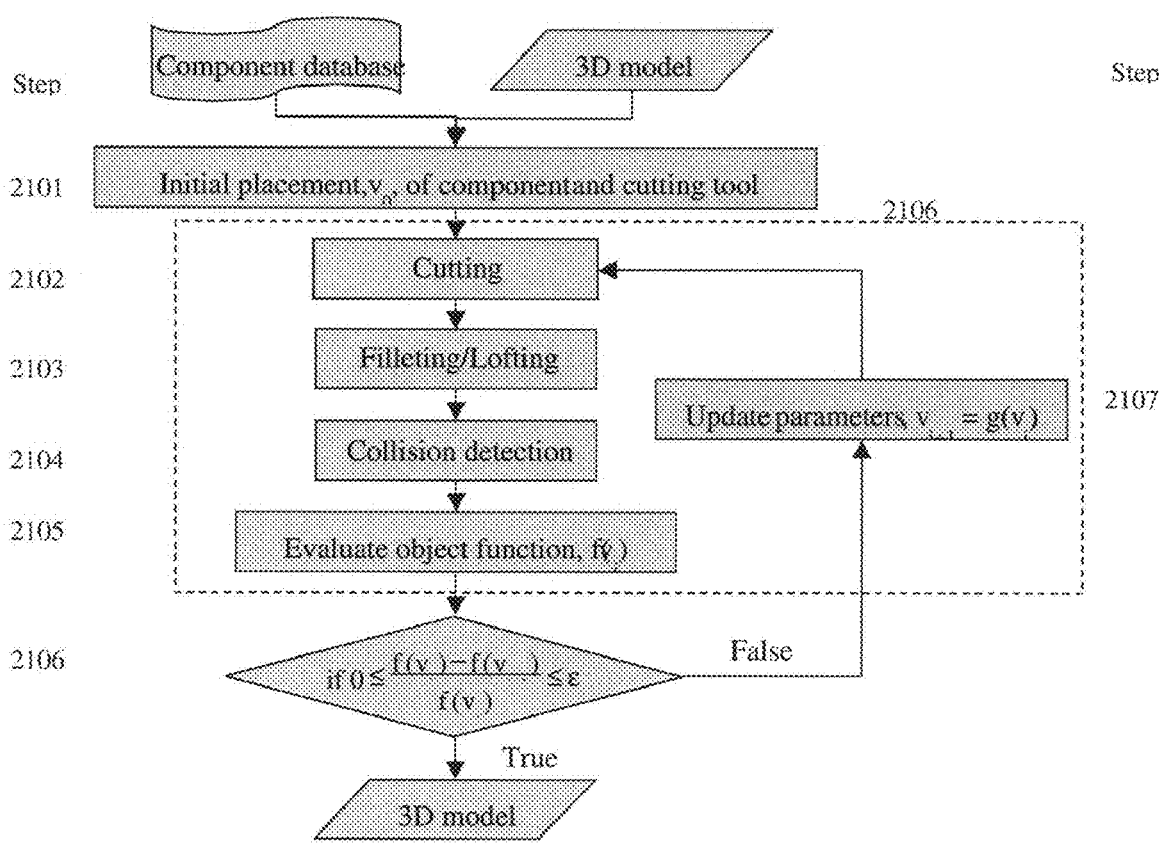
FIG. 21 contains a flow chart for the loop used by a rule-based approach for the optimal component placement, cutting and filleting/lofting of the visible part of the surface.

An alternative strategy for the automated placement of components is to apply an object function, f(v), which expresses the quality of the placement, v, of the components (and the closely related component surface, cutting and filleting/lofting 20' operations) The flow chart of this approach is shown in FIG. 21. The optimal placement, v*, of the component surface and components can then be obtained by determining the placement, which optimises the criterion, $f(v^*) \leq f(v)$ Note that the parameters, v, in FIG. 21 usually also contains the free parameters related to the cutting and filleting/lofting operations. The optimisation can be constrained by a number of factors such as collision between components and shell room for other components and features (e.g. ventilation channel, amplifier, microphone, vibration pick-up, microchip, battery, and printed circuits), the angle of the component in the shell and the angle of the component with respect to the ear/head. The constraints can either be incorporated as hard or soft constraints, where a penalty function is incorporated into the objective function. In practice soft constraints can act as hard constraints if a very high penalty is assigned for violation of the constraint, e.g. a collision.

The object function, f(v), may consist of a weighted sum of the terms related to the soft constraints and a number of other terms which express the quality of the earpiece. Preferably these terms are the volume of the shell, the outer shell surface area, the visible shell surface area, the length of intersection between the reference ear and the cutting surface, the area of the cutting surface after the cut, the maximal penetration of the reference ear by a component, the average of the penetration and the acoustic properties. As seen in FIG. 21 the object function is usually evaluated after the component placement, cutting and filleting/lofting operations have been performed. However f(v) could be evaluated at any time after the parts to evaluate f(v) are present in the model. The weights on the individual terms can be manually selected, based on empirical evidence or learned from a training set.

General-purpose optimisation methods such as steepest descent, conjugated gradient, quasi-Newton methods, Newton methods, dynamic programming, simplex methods, pattern search, generic algorithms, simulated annealing and stochastic diffusion can be applied to determine the optimal placement Most of the optimisation algorithms are iterative methods and require an initial configuration, $v_0$, which is generated manually or automatically 2101, see details below. Given a placement v, a collision detection 2104 is performed followed by an evaluation of f(v) 2105. If the relative improvement is below a specified threshold, $\epsilon$, 2106 the algorithm is finished otherwise the placement is updated 2207. The main difference between the optimisation methods is the way the placement is updated 2207, $v_{i-1}=g(v_i)$, during the optimisation.

An alternative to apply general-purpose optimisation methods is to use pseudo physics for the optimisation. Preferably a simplified physical model of the system is formulated. This pseudo physical model can be very powerful for updating of component placement when the component collides with another component or the shell. In practice the model may be applied to make the colliding component "bounce off" the shell or another component. Classic physics can be used to perform this type of modelling e.g. combined with approximate surface normals in the collision regions. Some object function has direct physical model interpretations. In this case the full optimisation can be performed in the physical framework. In most case however the physical modelling is combined with general-purpose optimisation methods, e.g. by applying physics for collisions and otherwise general-purpose, optimisation methods.

Penalties may vary over the ear e.g. penetrations in soft parts of the ear obtains a lower penalty than in hard parts of the ear or penetration of parts of the shell consisting of hard material receive lower penalties than penetration of harder regions. The different penalties are obtained by assigning different weights to the relevant parts of the ear. These weights are then multiplied on the initial penalty corresponding to the same parts of the ear as the weights. High weights lead to high penalties. In the case of penetrations of hard and soft parts of the ear, the hard and soft parts of the ear will be assigned high and low weights, respectively. The weights can be input by an operator or obtained automatically from the most similar model in the database. In the case of weights related to anatomical features of the ear, the weights can be obtained by a registration of the model to an anatomical atlas from which the weights can be derived. The anatomical atlas can either be based on a, (single standard ear or different standard ears for different groups. The weights can also be determined based on the dynamic variation of the ear and especially the ear canal under different circumstances, e.g. with open and closed mouth. The dynamics are preferably derived from a set of different models of the same ear using shape statistics. The set of different models should have been captured under different circumstances. An alternative strategy is to modify the reference ear by adding or removing material (see section 1.4.17) to change the penalties in the object function.

A selection tool may also be used to assign different materials for the earpiece to different parts of the 3D model. Thus, one problem with earpieces is that they are exposed to sweat from the surface of the auditory canal and/or the meatus. Parts of the earpiece in contact with the skin of the wearer can thus be marked and prototyped using a particularly sweat resistant material, while the other parts are made in another material, which needs not be sweat resistant The selection of such materials are known to the person skilled in the art of earpiece manufacturing. Similarly, it may be advantageous to select materials, which are non-allergenic to those parts of the model being in contact with the skin of the wearer. The selection can be performed by a rule based approach, according to which surfaces within a certain distance from the skin of the wearer are selected.

For some devices a number of different components exist with the same functionality, e.g. different transducers. To determine the optimal component each of the possible components are selected and the placement is evaluated and optionally optimised using the described procedure. The component, which obtains the lowest value of the optimiser object function, is selected by the system as the best component. A similar procedure can be used for automated selection of the components in the manual approach.

Initialisation of the component placement is crucial to the success of the later optimisation. Preferably the initialisation is performed by the similarity-based approach or a feature-based approach, where extracted features are used for positioning. One way to perform the feature-based initialisation is to slice the part of the present model into a number of slices. Preferably these slices have approximately the same orientation as the preferred component orientation e.g. with respect to the canal. Each slice may then be analysed. This analysis may be performed by examining whether the components or a derived bounding box can be placed approximately inside the slice. The analysis is usually subject to a number of constraints, e.g. the angle of the components. A slice fulfilling the criteria is then used for initialisation—typically the slice closest to the canal. Based on the previous analysis the component is placed, e.g. by aligning the centroid of the component with the centroid of the slice. More details on features can also be found in section 1.4.18.

1.4 6 Cutting the Visible Part of the Surface

In close relation with the placement of the component on the visible surface is usually performed a cutting of the visible part of the surface, which removes the unwanted part of the visible surface: The cutting is performed as described in section 1.4.4. The cutting of the visible part of the surface using a curve-based cutting tool is shown in FIG. 22.

Often the components or component surface is used to generate an initial cutting curve or surface, which can be adjusted by the operator. In some cases the cutting is performed directly by the component surface or a curve/surface derived from the components or component surface, e.g. a surface estimate of the component surface shifted in parallel toward the canal of the model or by forming a curve from points projected from the component or component surface onto the shell surface. Alternatively the cutting can be performed more or less independently of the component and component surface. If the component surfaces and shell surface are not combined during the cutting, the two surfaces may be connected using the loft operation (see section 1.4.7).

In the case of the similarity based scheme the cutting tool and position is directly derived from the most similar model. In the case of the rule-based approach the free parameters of the cutting is included in v and changed to optimise the formulated object function, f(v). The cutting parameters are usually initialised from the component surface and may also be locked to the component surface to reduce the number of free parameters to optimise.

1.4.7 Filleting/Lofting

Figure 30:
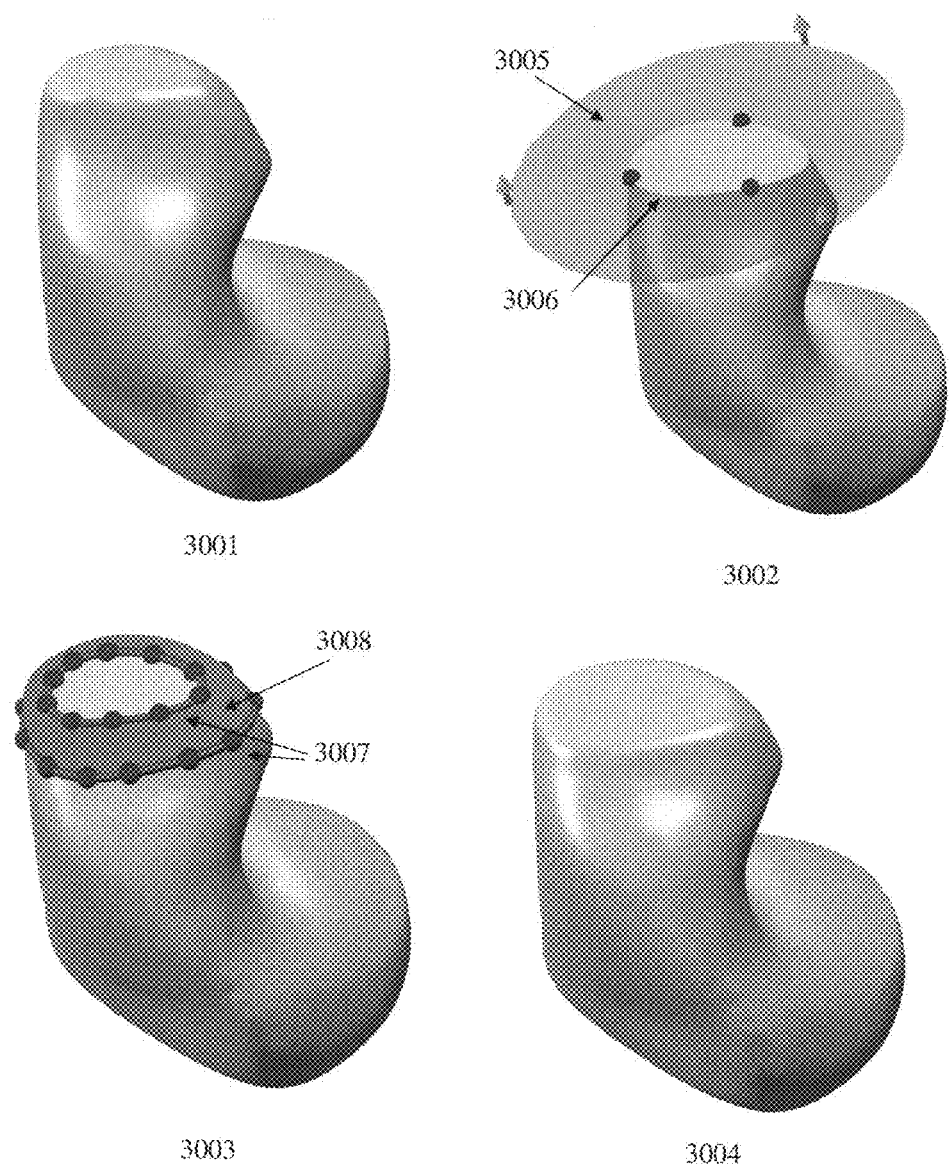
FIG. 30 shows a manual cutting with a planar surface at the canal part of the surface followed by a filleting/lofting.

Filleting is the process of rounding or smoothing an edge. Edges are undesirable features in earpieces, where smooth and round surfaces in general are preferred. Filleting is illustrated in FIG. 30. Lofting is the process of connecting two surfaces by a new surface. As shown below fillet and loft are closely related.

A very powerful approach to fillet is to remove the triangles 3008 in a neighbourhood on and around the edge 3006 and fit a parametric surface to the neighbourhood of the hole created by the removed triangles. The surface should preferably be a smooth surface such as a 2nd, 3rd or lower order surface, a NURBS surface or another type of spline surface. New vertices are then sampled on the fitted surface and connected by triangles. What triangles to remove may be determined by removing all triangles parts of triangles and/or vertices in a certain distance from the edge or by directly selecting the proper neighbourhood 3003, e.g. limited by two curves 3007, one on each side of the edge, see FIG. 30. The curves can be manually adjusted by a number of visual control points.

Figure 23:
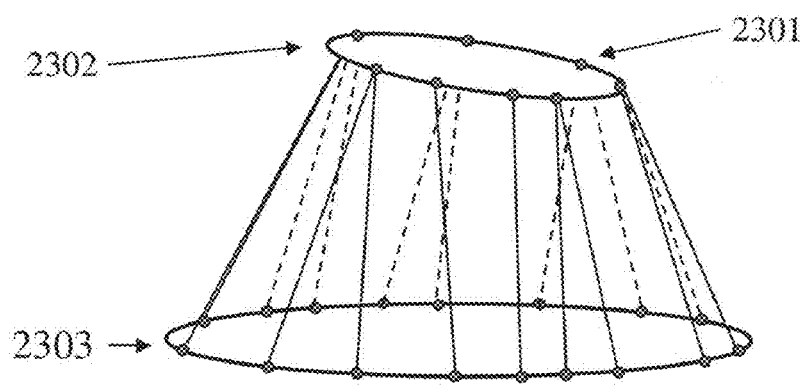
FIG. 23 shows the first step in the illustrated loft operation, which is to determine the correspondence between the vertices at the two boundaries.

When the triangles have been removed the fillet usually turns into a loft operation, where the boundary of two surfaces need to be connected. Note that the loft operation in general can be applied to connect two surfaces. The first step in the illustrated loft operation is to determine correspondence between the vertices 2301 at the two boundaries 2302, 2303, see FIG. 23. The correspondence may be determined by an exhaustive search for the correspondence that yields the lowest average distance between the corresponding vertices under the constraint that the order of the vertices is preserved.

The illustrated loft is based on a cubic B-spline surface, which requires a number of control points to be specified. For each vertex is calculated the vector, $v_c$, which is perpendicular to the vertex normal and the boundary orientation vector in the vertex. The vertex normal is calculated as the area weighted average of the triangle normals of the triangles connected to the vertex. For each vertex in the set of corresponding vertices two control points are created as the vertex $\pm v_c$. An additional control point is then created as $v_{c1}$ and $v_{c2}$ added to the midpoint between the corresponding vertices $p_1$ and $p_2$. Beside the created control points the two vertices also act as control points. When this process has been repeated for all sets of corresponding vertices, the surface is fully defined by the controls points. New vertices are then sampled on the surface, i.e. by sampling the vertices on the spline, which connect the corresponding vertices. Given these vertices and the ordering of the corresponding vertex sets, the neighbour relationships between the sampled vertices are known. Knowing these relationships makes. K straightforward to connect the neighbouring vertices by triangles. The result of a loft is shown in FIG. 24 and FIG. 30.

Figure 24:
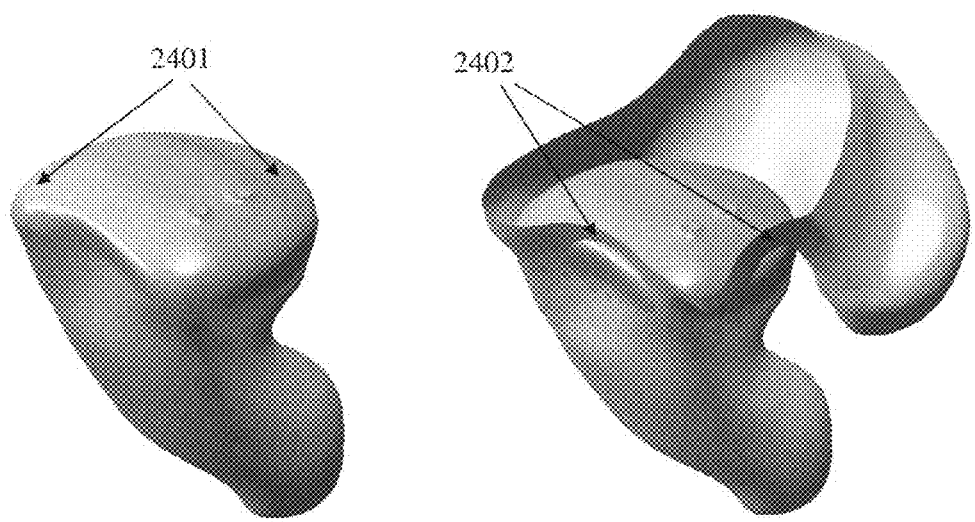
FIG. 24 illustrates the result of lofting the model and component surface in FIG. 22 visualised alone and in the reference ear.
Figure 25:
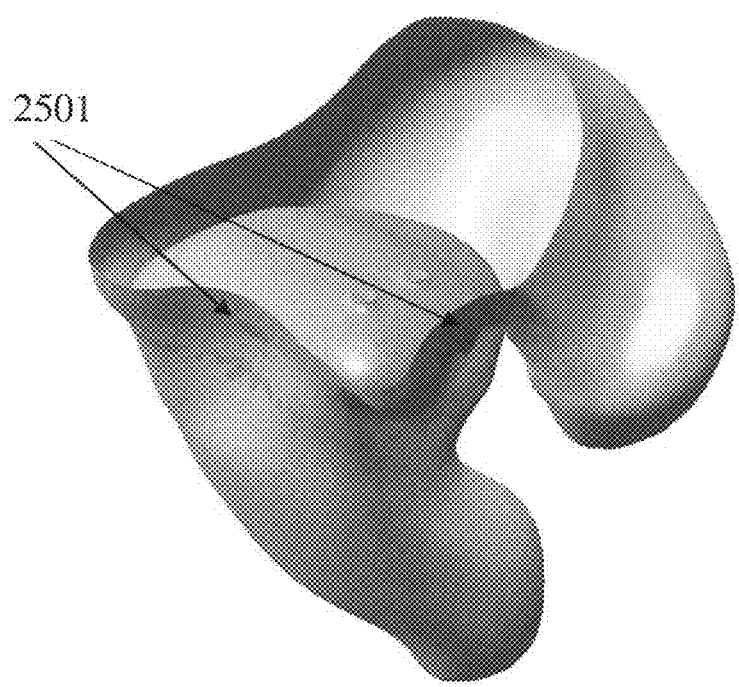
FIG. 25 illustrates the result of a lofted surface when the additional control points between the corresponding vertices have been moved backward along $v_{c1}$ and $v_{c2}$ until they are located behind the surface of the reference ear.

When the fillet/loft has been applied to the model it is not ensured that the reference ear model is not penetrated by the connecting surface 2401, see FIG. 24. This penetration 2402 can however be minimised by moving the control points behind the surface of the reference ear. FIG. 25 shows the reduced penetration 2501 obtained by moving the additional control point between the corresponding vertices backward along $v_{c1}$ and $v_{c2}$ until it is behind the surface of the reference ear.

A number of alternative approaches exist for a fillet operation. The simplest approach to fillet is to apply the smoothing on the edge and its neighbourhood. Refer to section 1.4.12 for details on smoothing.

Another approach contracts cylinders with a predefined radius as close to the edge as possible without letting them pass through the surface. The surface is then projected onto the cylinders in these areas forming a rounded edge with constant curvature. Alternatively the triangles in the neighbourhood around the edge can be removed and new vertices can be sampled from the cylinder surface. Note that the radius can vary along the edge.

1.4.8 Cutting and Filleting of the Canal Part of the Surface

Like the visible part of the surface a cutting tool is usually applied at the canal part of the surface to remove unwanted portions of the surface, see FIG. 30. The cutting can be performed by any of the cutting tools described in section 1.4.4. However the cutting is usually performed by a planar surface 3005, which is also used to close the hole after the cutting. In the manual approach the operator can select and adjust the cutting tool.

If the similarity-based approach is applied, the same cutting tool and position as applied to the most similar model is used. For the rule-based approach the position and orientation of the cutting tool is combined with the position of the components to be placed on the canal part of the surface. These free parameters, v, are then optimised with respect to an object function, f(v), similar to the one used in the placement of the component on the outer part of the surface, see also section 1.4.10.

Following the cutting a filleting operation 3004 (section 1.4.7) is performed on the cutting edge 3006. i.e. the edge where the cutting of the model has been performed. FIG. 30 illustrates the full process of cutting 3001,3002 and filleting 3003,3004 the canal part of the surface.

1.4.9 Shelling and Surface Offset

The original 3D model only consists of, outer surface, but most final 3D models require a shell, so a shelling operation may need to be performed. FIG. 26 shows a model before shelling 2601 and after shelling 2602. The outer shell surface 2603 corresponds to the input surface, so only an inner shell 2604 needs to be created. The operator defines the thickness of the shell. For many devices it is crucial that a minimum shell thickness is guaranteed.

Figure 27:
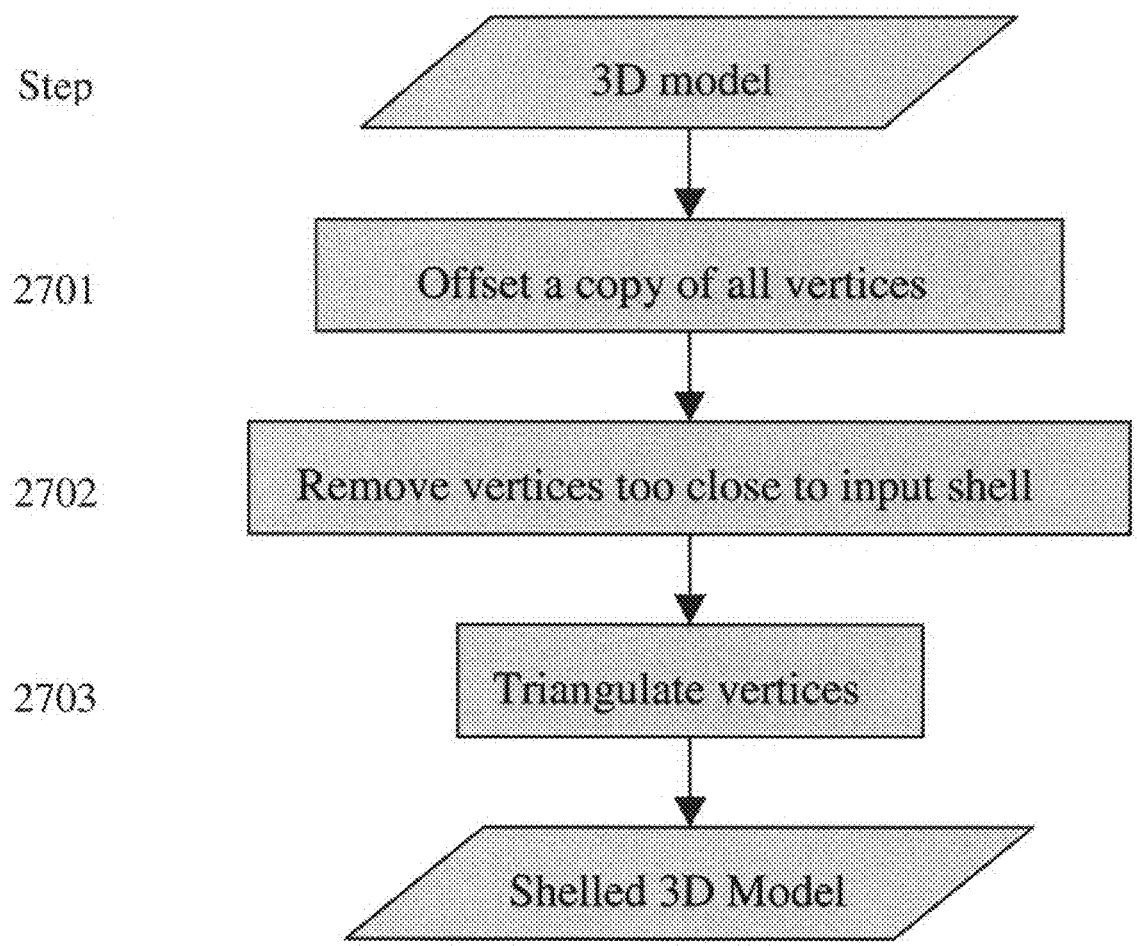
FIG. 27 is a flow chart of a shelling algorithm.
Figure 28:
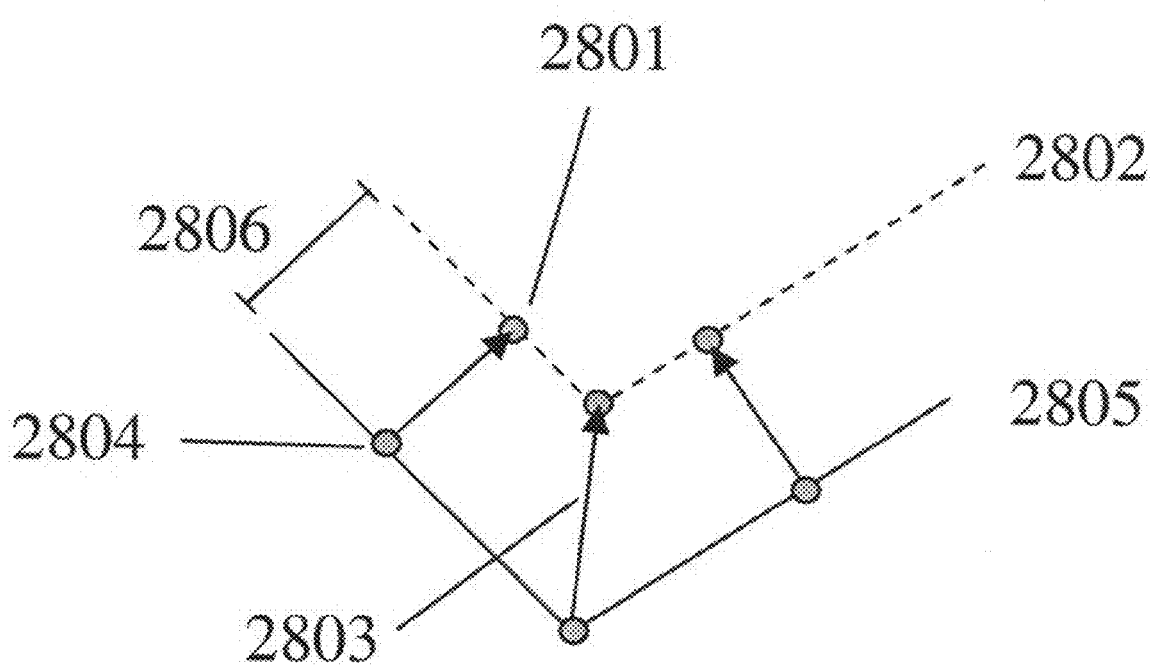
FIG. 28 illustrates the proper offset of each vertex to ensure minimum shell thickness when using a vertex representation of a 3D model.

An overview of a shelling algorithm is shown in FIG. 27. The first step 2701 in the algorithm is to create a copy of each vertex in the outer shell surface. FIG. 28 illustrates how the new vertex 2801 on the inner shell 2802 is created along the scaled normal 2803 of the corresponding vertex 2804 in the outer shell surface 2805. The vertex normal 2803 is calculated as the average of the normals of the connected triangles weighted by their area. If the minimum shell thickness 2806 has to be ensured it is not sufficient to offset the vertex with the specified shell thickness. However the offset, which locally ensures the shell thickness, can be found as the maximum scale factor, which projects the scaled version of the vertex normal onto the full length of the triangle normals scaled by the predefined thickness. Only the normals of the triangles connected to the vertex are of relevance. Unfortunately, the proposed offsetting only ensures a local shell thickness. In areas with convex surfaces and high curvature the offset vertices tend to violate the minimum shell thickness. These violating vertices are removed in the second step 2702 to ensure a proper shell thickness. Finally, the new inner shell may then be created by a triangulation 2703 of the created vertices. The triangulation may be performed using a standard 3D triangulation method such asproposed by Hoppe et al in Surface Reconstruction from unorganised points, Computer Graphics. 26(2), 1992, pp. 71-78.

Figure 29:
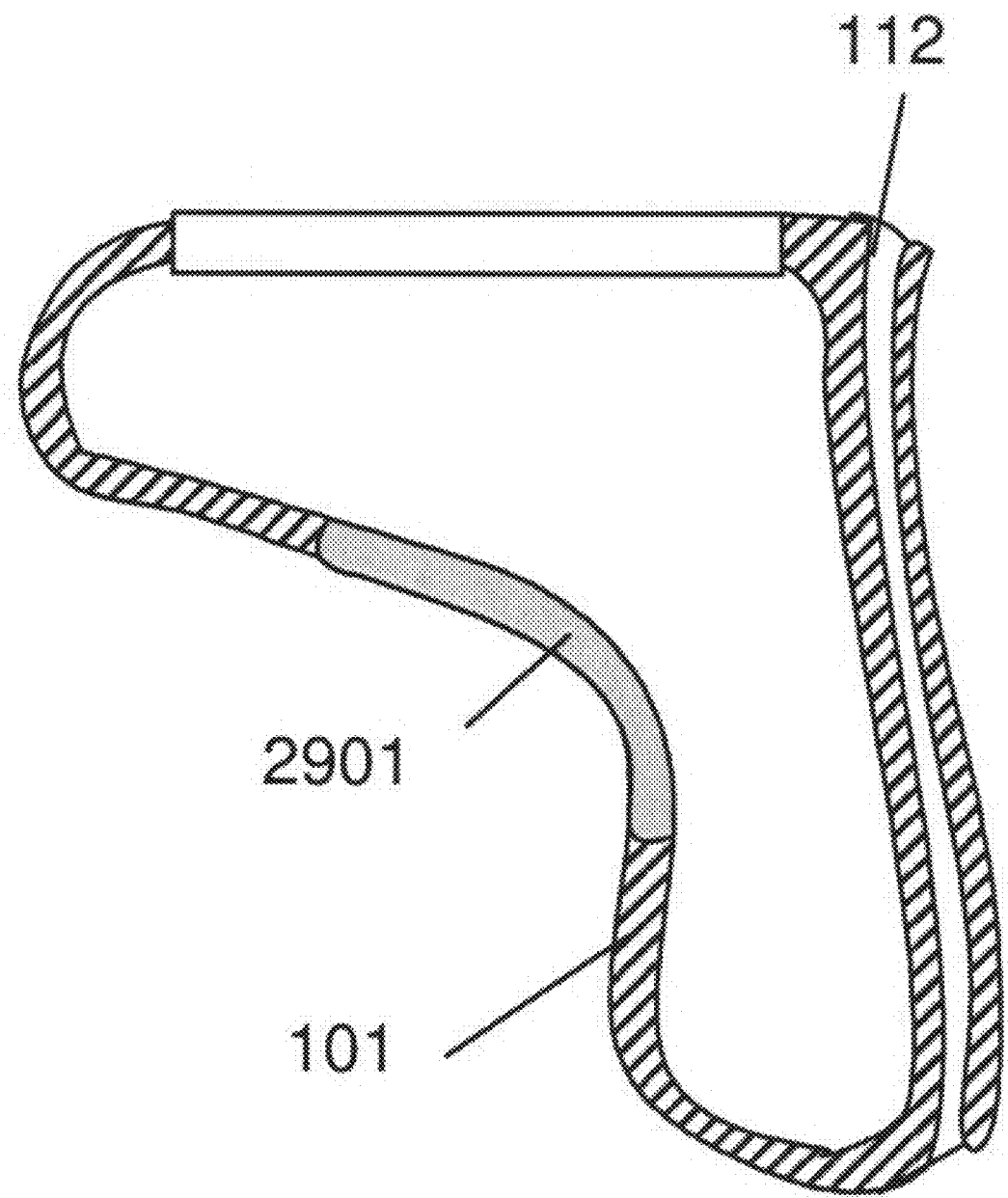
FIG. 29 illustrates an IN-THE-EAR earpiece with an area in softer material.

The proposed method may easily be extended to shells with a varying thickness by applying a local thickness in the offsetting of the individual vertices. Using a selection tool different materials can also be assigned to different parts as shown in FIG. 29, where a softer material 2901 is assigned to the part of the shell, which corresponds to the hard or changing part of the ear, e.g. part that changes when the mouth is opened and closed: For details on how to assigning different properties to different parts of the model refer to section 1.4.5.

The shelling algorithm may also be used to offset e.g. the outer surface. A small offset of the outer surface may be necessary to ensure, that the final shell has a perfect fit The only difference in applying the shelling method for offsetting is that the original model is removed after the offset-surface is created. Local offsets of parts of the shell can also be performed. e.g. to create O-rings on the canal part of the shell.

1.4.10 Component Placement on the Canal Part of the Surface

Figure 31:
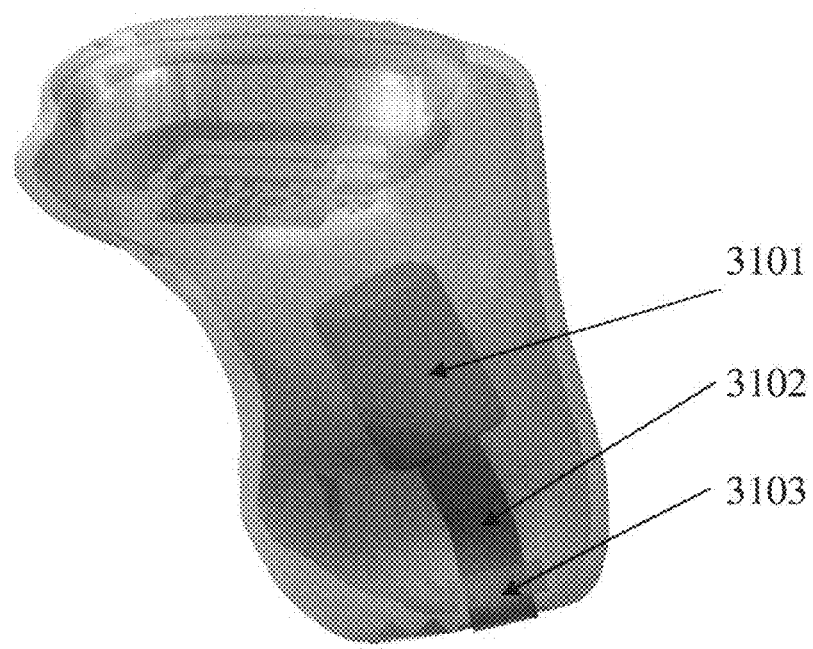
FIG. 31 illustrates a placement of components on the canal part of the surface. The components correspond to a sound outlet, the transducer and the tube, which connect the transducer and the outlet.

The component placement of the canal part of the surface is very important for a proper functionality of the apparatus and a pleasant insertion and pleasant use of the apparatus. The canal part of the surface corresponds to the part of the surface, which is inside the auditory canal. The term components should again be interpreted in a broad sense, e.g. an outlet connected with a tube to a transducer. FIG. 31 shows the result of cutting and placement of an outlet 3103 connected with a tube 3102 to a transducer 3101.

Manual Approach

Figure 32:
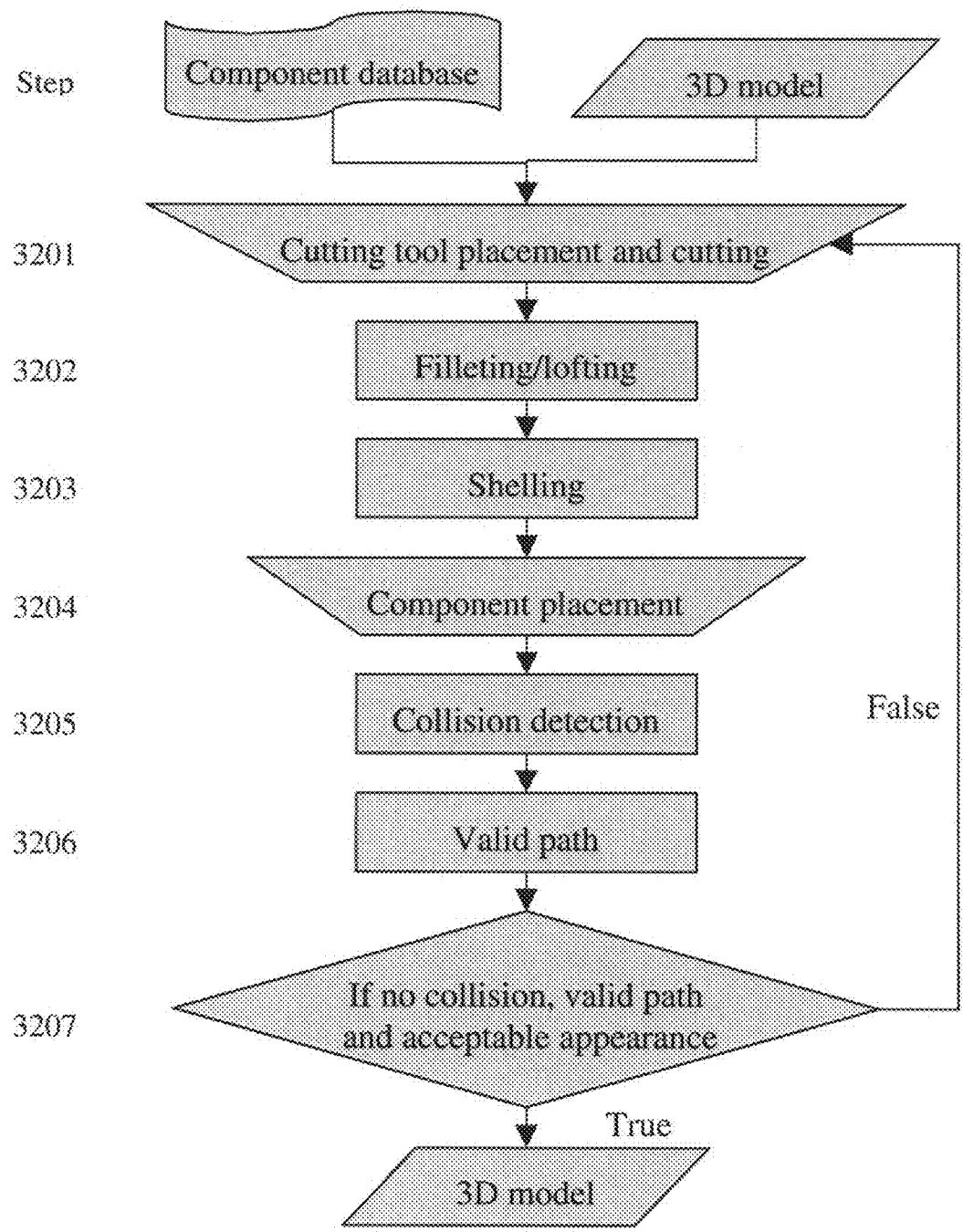
FIG. 32 is a flow chart for the loop used for the manual approach for cutting and component placement on the canal part of the surface.

A flow chart of the manual approach for component placement and the closely related cutting, lofting and shelling is shown in FIG. 32, Note that this flow chart illustrates the order of the operations used in FIG. 8, but many different orders of the operations could be applied: see e.g. FIG. 9 or 10. When placing components with multiple parts the parts can be adjusted simultaneously or individually. A component with multiple parts (outlet tube and transducer) is shown in FIG. 31. Relevant measures such as the length of the tube can be extracted directly for later use, e.g. in a manual assembling.

However, it is usually not sufficient that there is room inside the shell for the components. The components should also be able to enter this room. This may not be the case if the auditory canal is too narrow in some parts. To facilitate the placement of components a valid path tool 3206 may be devised for determining the existence of a valid path along which the component is able to move. A minimal path algorithm combined with collision detection may be applied to determine this path. Depending on the material properties of the components and the shell some intersection may be allowed. The legal degree of intersection can be specified, e.g. by the allowed amount of penetration or by the allowed amount of deformation of shell and component, which is required to make the component pass. The deformations may need to be modelled. e.g. by finite element models.

If no valid path exists removal of shell material in collision regions is possible following section 1.4.17. Collision regions are defined as the regions, where the component gets stuck. To facilitate the manual removal of material, the critical region is visualized and the neighbourhood is marked. However the valid path tool suggests the required local changes by removing material until the component is able to pass. These changes can either be accepted by the operator or accepted automatically under the constraint that the defined absolute minimum shell thickness is not violated.

The placement of the components may also be subject to other constraints e.g. the angle of the outlet with respect to the ear canal.

Similarity-Based Approach

The most similar model is extracted from the database and the same positions for components are applied. When the components have been placed the valid path tool is applied including the automatic modifications of the local shell thickness—if it is enabled.

Rule-Based Approach

The rule-based approach applies the similar methods as the rule-based approach for component placement on the visible surface. The main difference is that a valid path tool may be applied during the optimisation and invalid configurations are rejected/heavily penalized. A similar type of objet function is also used. However the weights of the individual terms in the object function may be changed to fulfil the specific requirement of the inner surface. Additional terms can also be added. e.g. the angle of the outlet with respect to the ear canal and the length of the tube connecting the outlet and transducer.

Preferably the optimisation of the placement is performed by a general-purpose optimisation algorithm by pseudo physics or a combination of both. The initialisation may be performed by the similarity-based approach or a feature-based approach, where extracted features are used for placement. One way to perform the feature-based initialisation is to slice the canal part of the present model into a number of slices approximately orthogonal to the local canal orientation. The first slice of the canal, which is reasonably close to orthogonal to the canal surface and approximately able to contain the components optionally including filleting and ventilation channel is applied for initialization. If a planar cutting is performed on the canal part, then the initial cutting plane may be identical to the slicing plane. The components may be placed with respect to the centroid and orientation of the slice.

1.4.11 Placement of Pressure Ventilation Channel or Sound Bore

Figure 33:
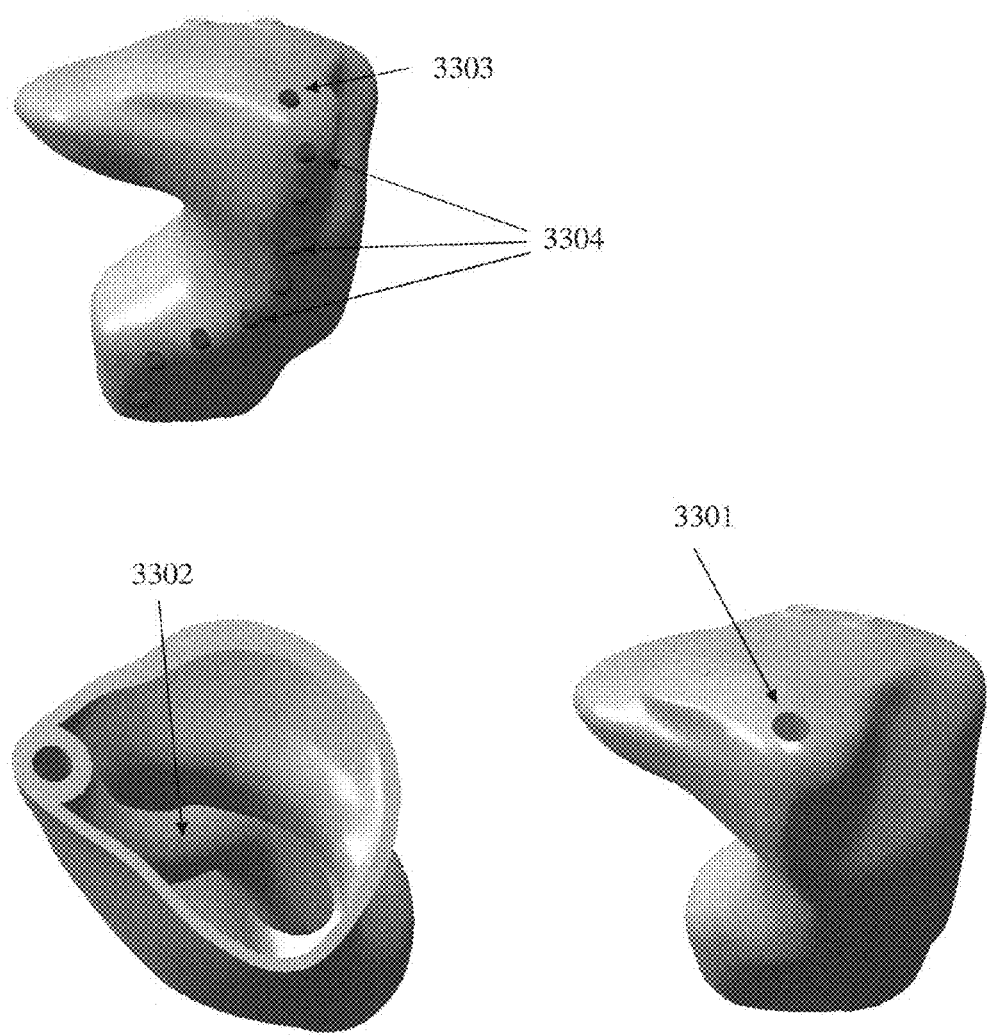
FIG. 33 illustrates a manual creation of a ventilation channel.

For some devices placed in the ear a pressure compensation/ventilation channel or a sound bore connecting the inside and the outside of the ear is required to obtain proper performance and pleasant use. FIG. 33 illustrates a model 3301 with a ventilation channel 3302. Traditionally this channel runs inside the shell, on the inner shell, on the outside or a combination of all.

Preferably the first step in creating the ventilation channel or sound bore is to determine the exit points on the canal and the visible part 3301, 3303 of the surface of the shell and the path 3304 connecting these points. The skin of the user must not cover the exit points and the bending of the channel may be constrained to ensure proper functionality. Further the path of the ventilation channel may be constrained by a minimum shell thickness, intersection with placed components and a requirement of leaving the outer shell surface unchanged.

Given the exit points and a legal path, the channel may be created by first adding a solid object, defined along the path, to the inner surface of the present model. The addition and later subtraction may be performed using a Boolean function, see section 1.4.16. The shape of the object may be defined by offsetting the specified shape of the ventilation channel or sound bore by the minimum shell thickness. In the case of a tube shaped ventilation channel or sound bore the solid object may correspond to a solid tube with a diameter equal to the sum of the ventilation channel diameter and the minimum shell thickness. A second solid object with the specified shape of the ventilation channel or sound bore defined along the path may be created and subtracted from the model, creating the final ventilation channel. In the case of a tube the second solid object corresponds to a tube with the specified diameter. Note that this method can generate ventilation channels with an arbitrary geometry, e.g. ventilation channels with cross sections of the following types; elliptical/circular, square/rectangular, T-shape, semi-circular with an edge, triangular with an edge, circular/elliptic with an edge. Ventilation channels with e.g. elliptic shape can make the channel stay in the shell and increase the space for components etc. Likewise the method facilitates the creation of almost any type of bores such as large bores, small bores, open bores and fish mouth bores.

Figure 34:
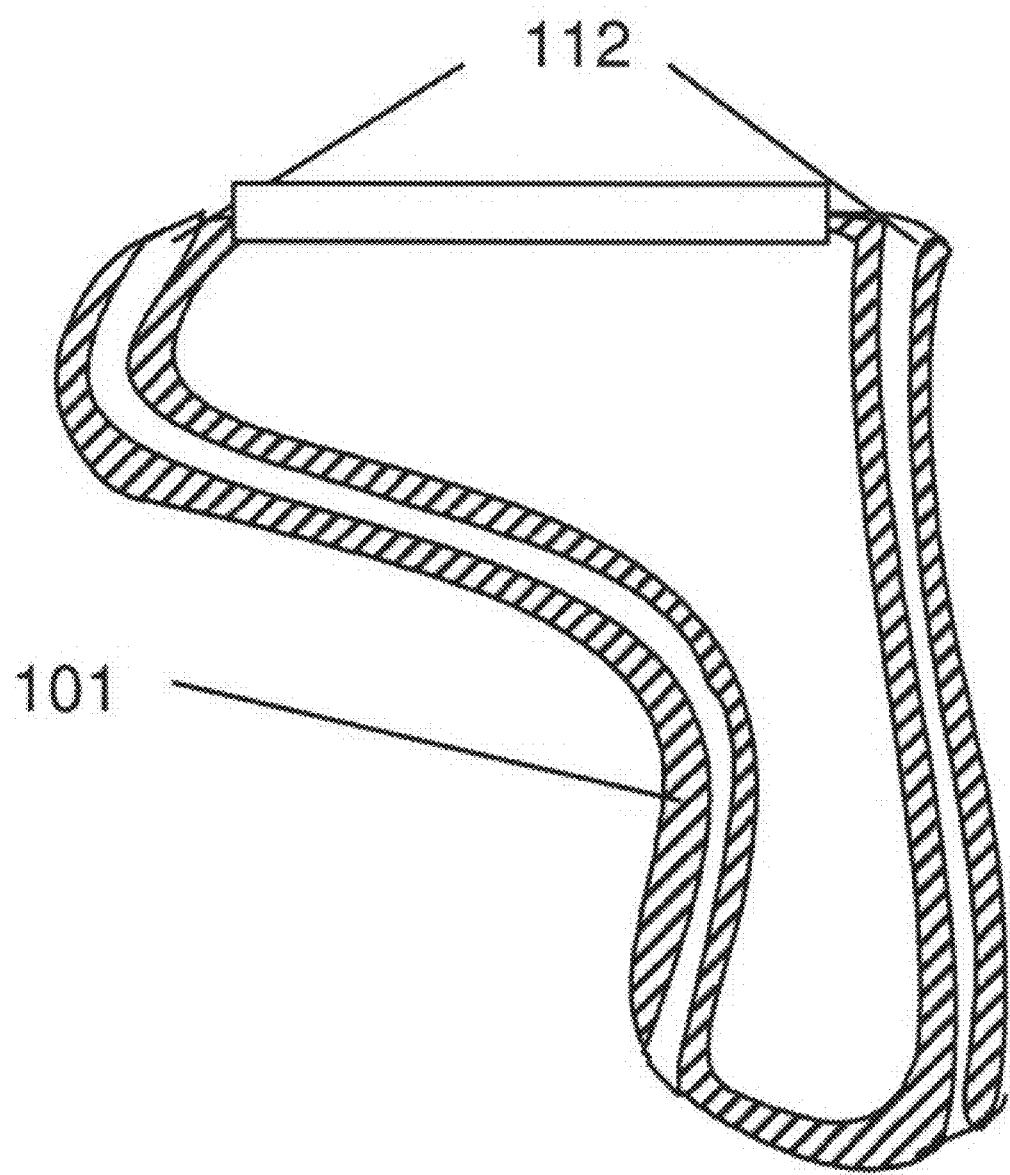
FIG. 34 shows an IN-THE-EAR earpiece with a double ventilation channel.
Figure 35:
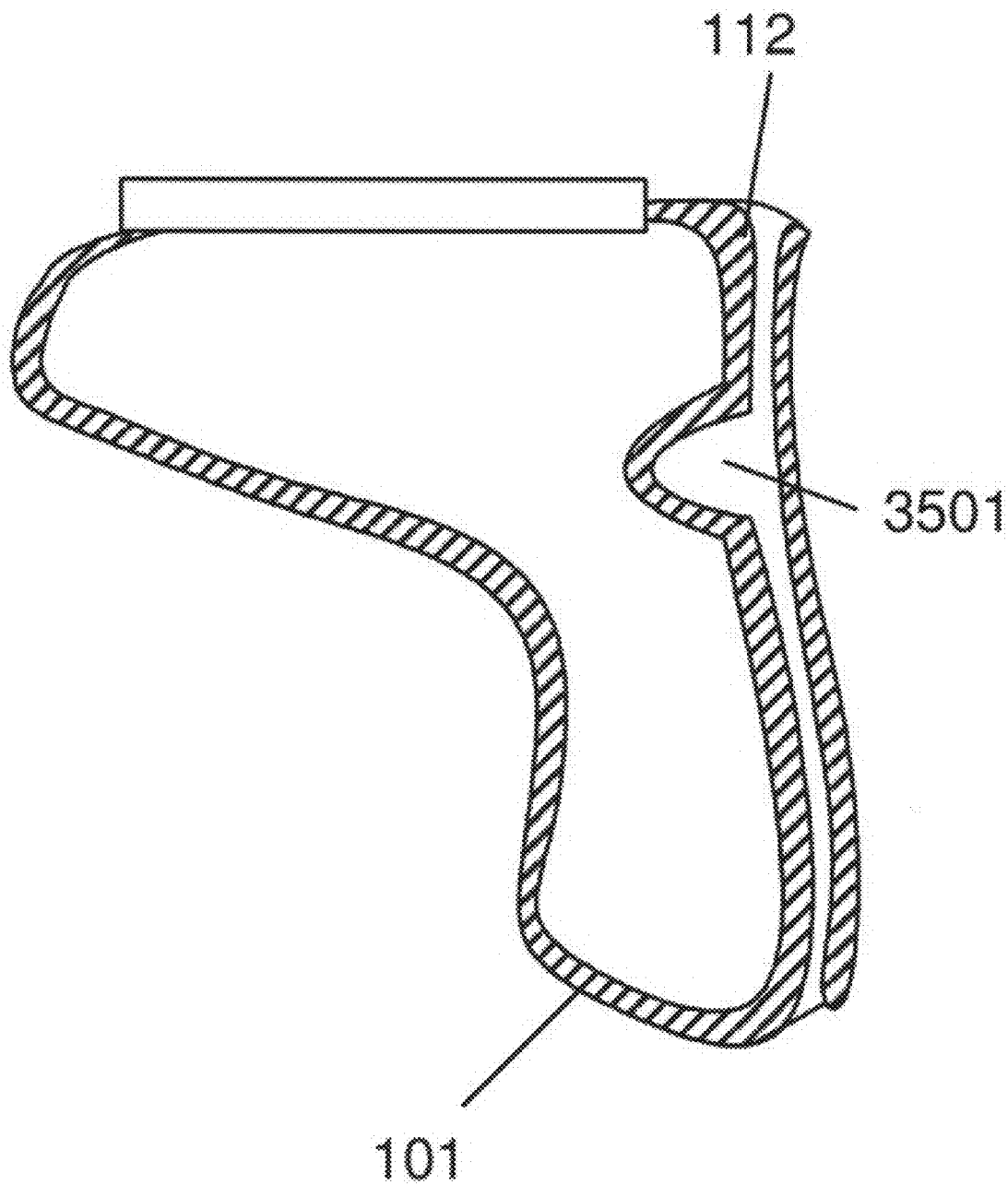
FIG. 35 shows an IN-THE-EAR earpiece with a feedback reduction chamber.

Note that the method describes the generation of a single ventilation channel or sound bore connecting the inner and outer surface. However the approach can easily be generalized to multiple channels (see FIG. 34) and short channels not necessarily leading the whole way from the inner to the outer surface. The method can also be used to generate ventilation channels or on the surface by not offsetting the points. Likewise, the approach can change shape and add extra features like a chamber along the channel by changing the shape of or adding the feature to the solid object, which is used to create the channel. FIG. 35 schematically shows a chamber 3501 in the channel. The chamber is used to improve acoustic properties and reduce pressure.

The possibility to design ventilation channels or sound bores with arbitrary shapes and paths, e.g. around the surface, can be applied to improve the acoustic properties and increase the protection towards earwax. Acoustic conductors integrated into the shell can also be created in the same way as the ventilation channels. Finally the acoustic properties of the ventilation channel or sound bore can be simulated and evaluated.

Manual-Based Approach

In the manual approach the operator may mark the exit points 3301 and a number of ventilation channel control points 3304 on the surface to define a sparse sampling of the path. Given these points, a continuous representation of the path may be created by fitting a curve, e.g. a spline. Before the curve is fitted, the points may be offset from the surface to ensure a proper shell thickness. Refer to section 1.4.9 for details on offsetting of points. The legality of the path with respect to intersections with components etc. may be determined using collision control and may visually be indicated to support the manual placement of the channel. If the path is illegal, the operator can move the individual control points to change the path until a legal configurations is obtained. When the points are adjusted the channel may be simultaneous visualized and illegal parts visually indicated. New points can also be added to define a more precise path Similarity-Based Approach The most similar model previously extracted from the database may contain information defining the exit points as well as the points specifying the path. In some cases the viewpoint of the operator (position and orientation) used during the selection of each point is stored with the model. By applying these viewpoints to the present model, the corresponding points on the present model can be obtained. Given the points on the present model the ventilation channel can be generated.

An alternative strategy is to project the points from the similar model onto the present model to obtain the exit points and the path. The projection is performed along the surface normal. By applying the projected exit points and the path, the ventilation channel is created.

Rule-Based Approach

In the automated scheme the exits of the ventilation channel may be placed given a preferred position. To make the position applicable to different models, the position is typically given relative to relevant landmarks such as surfaces or components. These positions can either be obtained by analysis of a training set or directly inputted by an operator. Preferably the path is generated using a shortest path algorithm, a "water flow" algorithm that determines the most southern path following the local canal bending or by sub sampling the line connecting the exit points and projecting these points onto the shell (following section 1.4.4). All path generation is subject to the previously mentioned constraints. Given the exit points and the path the final ventilation channel is created.

In the case no legal path can be generated for the first exit points, a number of other exit points may be tested. These points can e.g. be generated from a training set, by an operator or by permutations of existing points.

1.4.12 Optimise Visual Appearance

The visual appearance is one of the most important properties of the earpieces for the users. Hence it is crucial to optimise the visual appearance. Beside the optimisation performed during the previous operations a number of additional operations may be applied:

Smoothing or Fairing

The smoothing or fairing may be performed by a low pass filtering of the model surface followed by ant-shrinkage step. The anti-shrinkage can be required, because a low pass filtering shrinks convex parts of the surface. The low pass filtering may be performed by assigning a new position equal to the weighted sum of the vertex and its neighbours to each vertex. One way to perform the anti-shrinkage is to preserve the volume by scaling the full model. The defined number of iterations corresponds to the degree of smoothing. The smoothing can either be performed on the full model or on selected parts.

Colouring and Texturing

One of the last actions is to assign colours or texturing to the shell. The colours and the textures can be measured as a part of the scanning process or separately if impressions are scanned. Additional colours and textures can be sampled from a standard colour palette and a texture database respectively.

1.4.13 Optimise Shell Geometry

Figure 36:
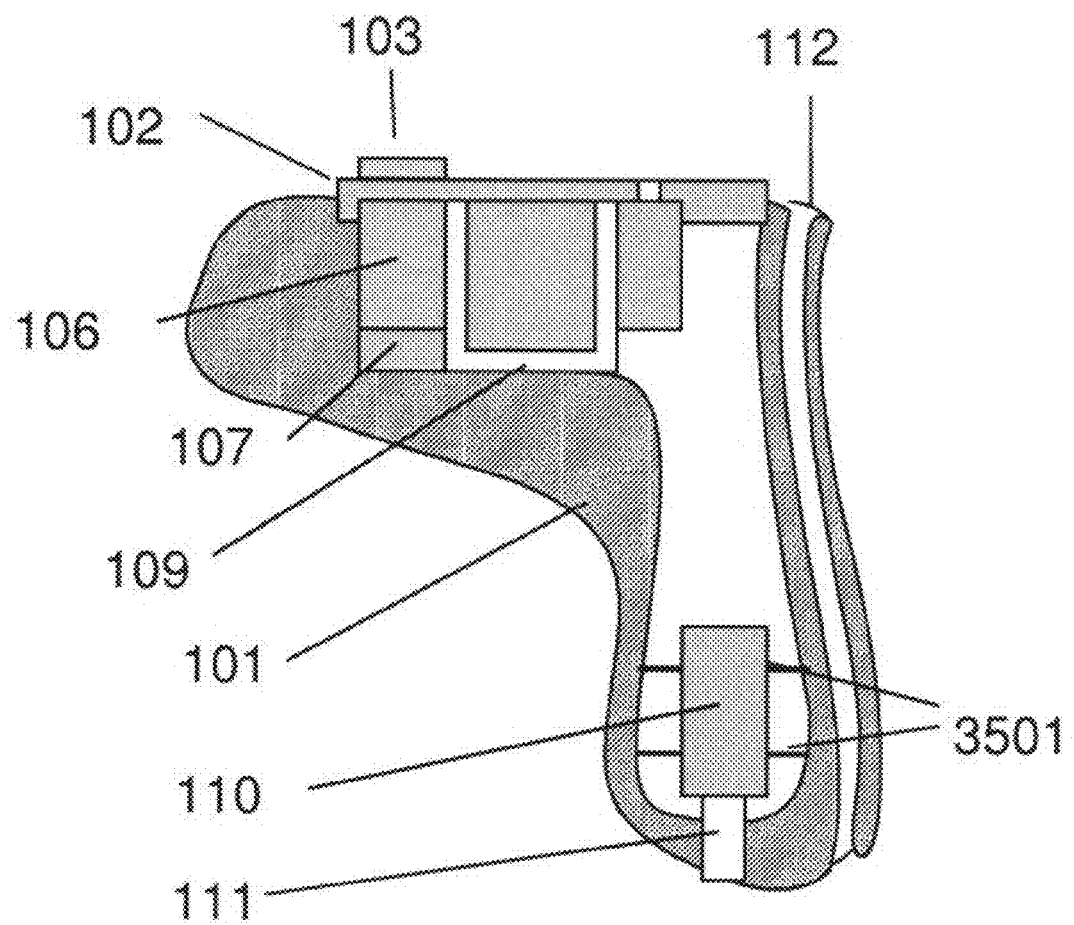
FIG. 36 shows an IN-THE-EAR Hearing Aid with variable shell thickness and holding spikes.

When all components have been placed and all surface modifications have been performed, the shell geometry can be, optimised. One objective of the optimisation is to improve the positioning of the components and increase the strength of the shell, see FIG. 36.

The positioning of the components may be improved by adding holders 3501 or extra material, which fits the exact geometry of the components. Holders such as spikes or rings, may be directly added by Boolean operations, see section 1.4.16 The holders may have vibration-reducing properties. Parts of bounding boxes or component negatives can also be used to add extra material, which fits the component. The addition may again be performed using a Boolean addition.

Adding extra material (see section 1.4.17) also increases the shell strength and compensate for limitations in the physical production process. The strength of the shell can also be improved by increasing the local shell thickness in non-critical regions as described in section 1.4.9. Grids, ribs, or other features can also be created on the inner shell, e.g. by a projection of the features on the inner shell followed by a Boolean addition. Again the objective is to strengthen and stabilise the shell. All modifications are constrained by collision detection and no valid paths are violated.

For some applications e.g. hearing aids it may be relevant to add extra material on parts of the outer shell surface to make the earpiece fit better and improve acoustics, e.g. by removing feedback. Preferably these areas are identified by the operator, anatomical knowledge or based on physical simulations. The addition of extra material is described in section 1.4.17.

1.4.14 Creation of Component Locks, Room for Faceplate and/or Multipart Shell

As one of the last steps the locks for components and/or room for the faceplate need to be created depending on the particular assembling process.

Component Locks

Figure 37:
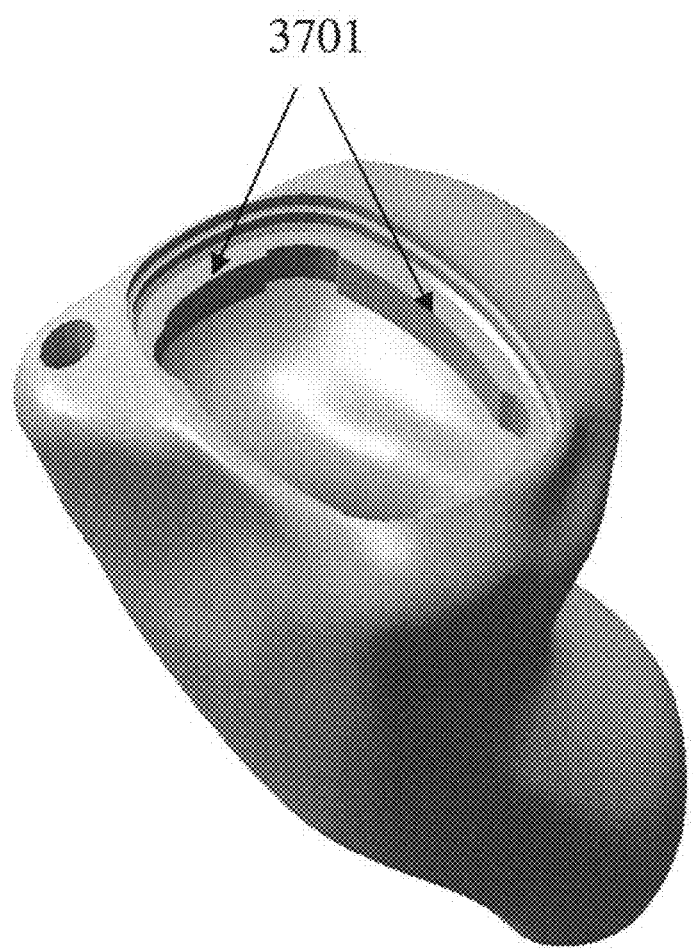
FIG. 37 illustrates the creation of a lock for the electronics and battery component.

In many applications locks are needed to make it possible to attach and lock the components on the final earpiece—especially if no faceplate is applied. Examples of locks are operable locks, one-click locks or bayonet click locks. These locks may be created by performing a Boolean subtraction (see section 1.4.16) of the negative of the component lock or the component from the present shell. FIG. 37 illustrates the creation of a lock 3701 for the electronics.

Room for Faceplate

Figure 38:
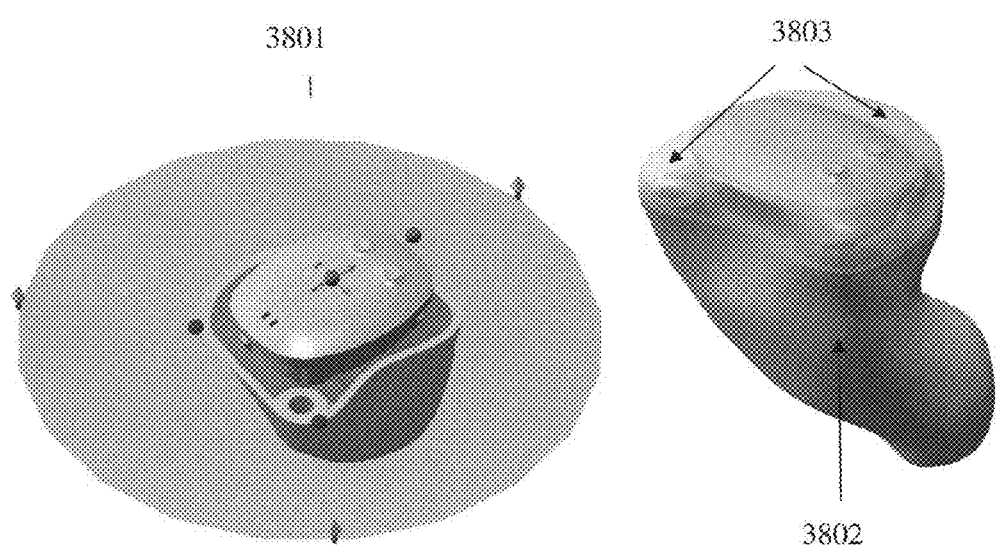
FIG. 38 illustrates the creation of room for the faceplate with a planar backside by performing a cut with the surface corresponding to the backside of the faceplate.
Figure 39:
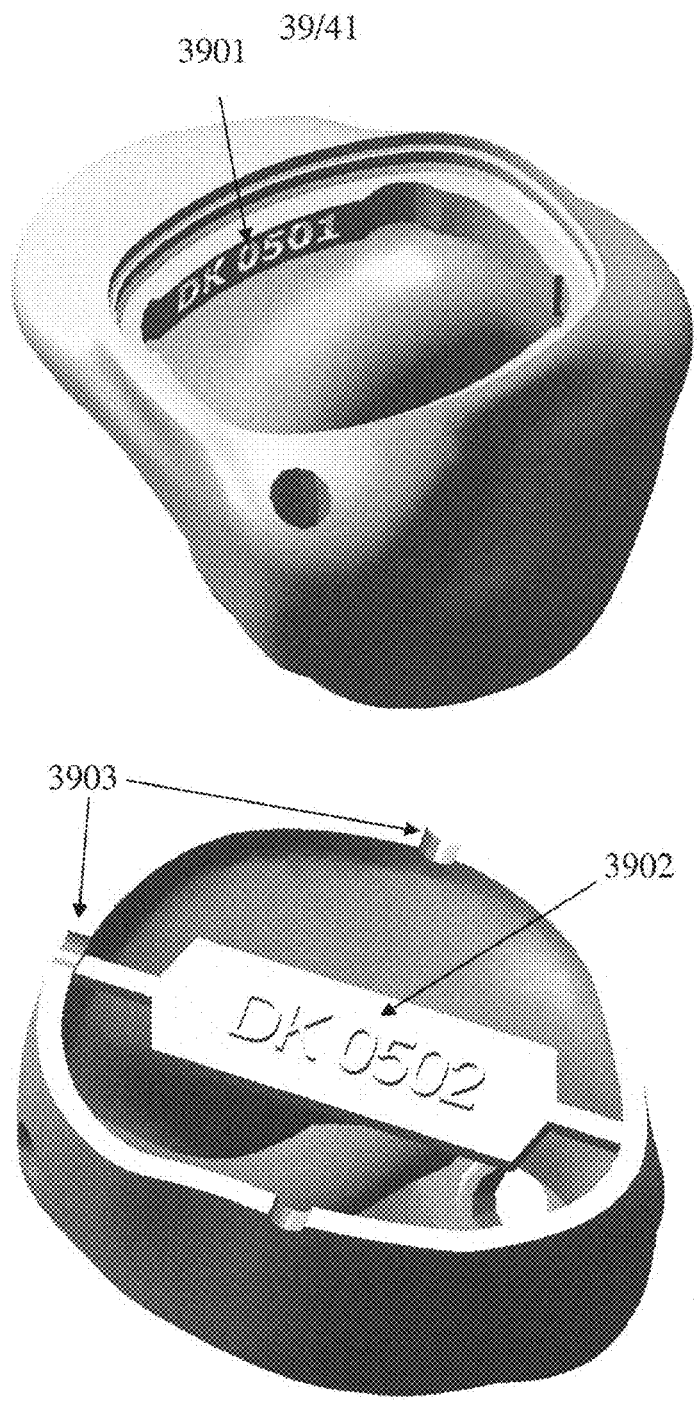
FIG. 39 shows an example of identification placed on the inside of the shell or as a detachable tag.

For different reasons many producers still apply a face or cover plate in the assembling, see FIG. 1. The position of the faceplate is directly determined by the position of the components on the visible part of the surface. To make the assembling with a faceplate possible room needs to be created for this faceplate, i.e. the part of the model, which should correspond to the faceplate needs to be cut away. FIG. 38 illustrates the final model 3802 after the removal of the faceplate part 3803 of the present model. The removal is performed by cutting the model with the surface 3801 corresponding to the backside of the faceplate model aligned with respect the position of the components. Preferably the backside of the faceplate presents structures to uniquely position and lock the shell and faceplate. Examples of such structures are lines, grids or other locks. FIG. 39 illustrates the use of a line structure 3903 for locking faceplate and shell.

When a faceplate is applied modifications of the faceplate need to be computer controlled if the final earpiece should obtain the same shape as the model before room was made for the faceplate. The modification of the faceplate may be controlled by supplying the milling paths for a milling device, which can be applied to modify the faceplate. The milling paths are generated by offsetting the surface outward with a distance corresponding to the milling head radius following section 1.4.9. The part of the offsetted surface, which corresponds to the faceplate is then sliced using planar surface cuts. For each slice the outer contour is extracted. These contours become the milling paths.

An alternative to apply a full faceplate is to use a small interface module e.g. a small ring containing a lock for the components. This interface module can then be glued to the shell and the components can be inserted and removed easily. In the full frame work the interface module is just interpreted as a component, which may be placed together with the other components.

Multipart Shell

Another option is to create a multipart shell, i.e. the shell is separated into two or more parts, which can be locked together. The separation of the shell into two or more pieces allows for easy insertion and replacement of components and reduces the need for large holes in the shell through which the components can be inserted. The separation of the shell into two parts is performed by cutting the present model with a single surface, which corresponds to the desired separation surface including locks etc. This cutting creates the first part. The second part is then created by cutting the present model with the same surface with swapped orientation. In a similar way more cuts are performed for shells with more than two parts. The separation could also be performed using Boolean subtraction.

1.4.15 Placement of Unique Identification

A large number of earpieces may be produced together In order to distinguish the individual earpieces a unique feature for identification, such as serial number barcode or colour code, need to be placed on the earpiece. An example of placing identification is shown in FIG. 39. Preferably the identification should either be placed inside the shell 3901 or on an extra piece of material 3902, which can easily be removed. In general the identification should be placed such that it easily can be read automatically, e.g. by a barcode reader or computer vision system. If the rapid prototyping device is single-colour, a serial number can be created with 3D characters, which are added or subtracted to the surface preferably by a Boolean operation, see section 1-4.16. For some single-colour rapid prototyping devices it is also possible to create identification by double exposure. In the case where other components are unique for the earpiece, these components can also be assigned a unique identification.

1.4.16 Boolean Operation

Figure 40:
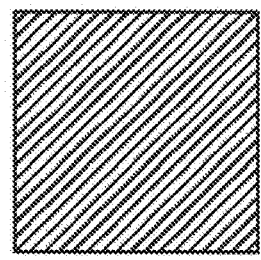
FIG. 40 illustrates Boolean functions on two 3D models, A and B.
Figure 40:
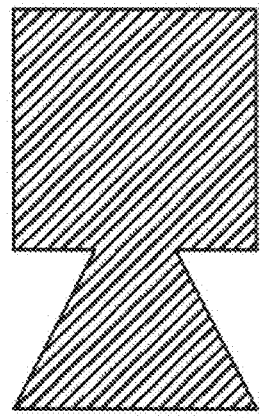
Figure 40:
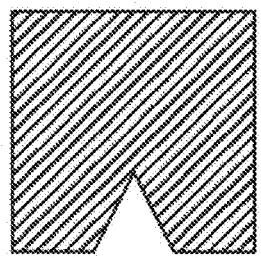
Figure 40:
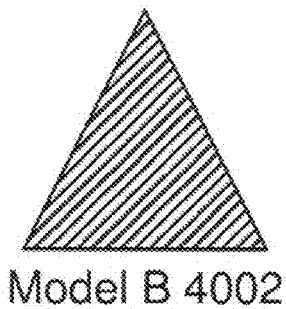

FIG. 40 shows how a Boolean function can be used to add, A+B, 4003 or subtract, A−B, 4004 two models, A 4001 and B 4002. The power of the Boolean function is also illustrated in FIG. 31, where the outlet 3103 is created using the Boolean addition of cylinder model followed by a Boolean subtraction of cylinder model with a smaller radius.

The Boolean algorithm has strong similarities with the surface cutting and closing function in section 1.4.4. For each intersecting triangle in model A and B the loop to be triangulated can be determined. Recall that the loop consists of the intersections of the triangle edges and one or two vertices from the triangle, see FIG. 14. Compared to the cutting and closing function the difference is which vertices in the triangle to insert in the loop.

In the case of the addition, A+B, the vertices in the loop should be selected as the vertices above the other model surface for both A and B. In the same way as in the cutting operations the triangles below/behind the other surface are removed and the two surfaces are merged.

For subtraction, A−B, the model A is treated in the same way as in addition. The vertices in the loop for triangles in model B are selected as the vertices below the surface A. Finally, the triangles in B above/in front of the surface of model A are removed and the two surfaces are merged.

1.4.17 Add/Remove Material

Extra material can locally be added or removed. This may be performed by locally offsetting the surface outwardly or inwardly, respectively. The addition/removal can be based on a single point on the surface or selection of an area. In the case of a single point the vertices within a specified distance from the points are offsetted as a function of their distance to the point The relationship between the amount of offset and the distance is controlled by a proper transfer function, e.g. a Gaussian. The actual offsetting of the individual vertices is performed as described in section 1.4.9.

If the input is a selected area all the vertices within the selection are offsetted. The amount of offset is calculated based on the distance from the vertex to the selection boundary combined with a proper transfer function.

In some cases larger amounts of material need to be added, e.g. if parts of the ear canal is missing, the canal may be extend. In the general case the material to add is preferably extracted from a similar or standard model and added to the model by a Boolean operation. In special cases like the extension of the ear canal it may be advantageous to fit a parametric surface to the neighbourhood of the extension. Additional control of the surface can be obtained by adding a number of surface control points, which make the operator freely able to adjust the shape of the extension.

1.4.18 Extracting the most Similar Model from the Database

The core in the similarity-based approach is to extract the model which is most similar to the present model from the database. Preferably the first step is to insert the coordinate system in the present model following section 1.4.3. A number of features are then extracted from the model The features should preferably be homological points, distances and angles between homological points, lower order moments, local curvature and other differential-based features. The applied features should preferably be invariant of position, orientation and scale Together with each original model in the database the corresponding features are stored. Each model has a corresponding point in feature space. The candidates for the most similar model are then extracted as the "nearest neighbours" to the feature point, which is related to the present model. Preferably the nearest neighbours are determined using the Euclidean or Mahalanobis distance in feature space, neural networks, fuzzy logic or another parametric or non-parametric model.

A registration of the present model and each candidate may then be performed and the closest model may be extracted as the most similar model. The closest model may be defined with respect to the average least square distance between the vertices in the present model and surface of, the candidate models. The registration may be performed using the Iterative Closest Point algorithm (Besi, P. J. and McKay, N. D., "A method for registration of 3D shapes", IEEE Transaction on Pattern Analysis and Machine Intelligence. 17(1), pp. 239-256, 1992).

1.4.19 Visualisation and Simulation

The earpiece and the related components can be visualised fully identical to the final product where not just the major components but also wires, connectors and all other used pieces are included. Simulation may be performed to determine the influence and movement of the transducers, tube, wires etc. when the earpiece is moved such as when user is moving or eating. These simulations are preferably performed using classical physics and also include mutual interaction The required physical parameters such as mass and flexibility are assigned to all the individual components. One advantage of the physical simulation is the possibility to optimise the size of different component, e.g. the length of the wire connecting electronic and phone.

Insertion and removal of the earpiece in the virtual ear may also be simulated. This simulation ensures that the earpiece is actually able to enter the ear. The simulation also includes the amount of deformation and pressure applied to the ear and earpiece, which is required for the insertion and removal. The amount and position of the ear deformation and pressure makes is possible to estimate the nuisance caused by the insertion and removal of the earpiece. Likewise the nuisance can also be estimated when the earpiece is placed in the correct position Again realistic physical parameters are assigned to the ear and earpiece. The parameters assigned to the ear may be obtained by a registration of the ear to an anatomical atlas.

Simulations of the acoustic properties of the modelled earpiece can also be performed.

The full visualisation and physical simulations facilitate the most realistic evaluation of the modelling result and can be used to optimise the modelling to obtain the overall most satisfying result.

1.5 Output of the System

Figure 41:
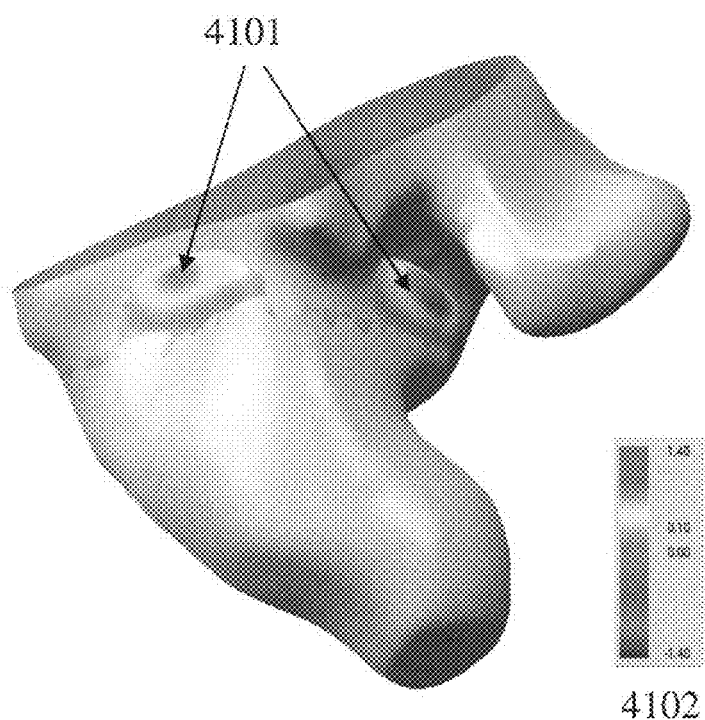
FIG. 41 illustrates a difference map showing the penetration of the reference ear by a final earpiece.

The final optimal 3D model is then added to the database. The database has a number of applications, e.g. it can be applied to produce new earpieces using the similarity-based approach, derive shape statistics used for purposes such as optimal component design and improved acoustic simulation, perform growth and age modelling of the auditory canal and the rest of the ear, reproduce lost or damaged earpieces and/or create quality reports. A part of the quality report can be the amount of penetration of the virtual ear, see FIG. 41.

The physical version of the final 3D model may be produced using a rapid prototyping set-up such as Milling, stereo lithography/SLA, solid ground curing, selective laser sintering, direct shell production casting, 3D-printing, topographic shell fabrication, fused deposition modelling, inkjet modelling, laminated object manufacturing, nano-printing or any other system that produces real models from 3D computer models. The final 3D model will be directly saved in a format compatible with the manufacturing set-up. Using a packing algorithm a large-number of 3D models may be optimally positioned in 3D space and manufactured simultaneously to increase production speed.

The system is also able to generate post processing instructions and other derived data e.g. programs or settings for the corresponding hearing aid electronic. When faceplates are used generation of instructions for the milling of the faceplate is essential if the correct shape should be obtained. These instructions are also stored in the database and can be downloaded to the milling machine manually or automatically.

Instructions for manual or automated assembling are also generated. Preferably these instructions include assembling instructions, component specifications and optimal dimensions, e.g. of tubes and wires. One use of these instructions is to automatically, prepare and adjust the components for assembling. Due to the precise knowledge of the shape the system is also able to create instructions for automated assembling of shell, faceplate, electronics and other components. Without this shape knowledge it is basically impossible to perform automated assembling e.g. by a robot, due to the small dimensions and high requirements for precision. The knowledge of the precise position of components can also be used to mount components before or during the production of the shell. The system is also able to optimise the position and orientation of the shell in the production to facilitate this placement of components. This makes it possible to build component into the shell and to mount components that cannot be inserted into the final shell. Simple components can also be created directly, e.g. printed.

Most of the handling and processing of earpiece require that the identity of the present earpiece is known. The earpiece is preferably identified automatically, e.g. by a barcode reader or computer vision system.

The invention claimed is:

1. A method for computer-assisted modeling of customized earpieces comprising at least one part being individually matched to one or both of an auditory canal and a meatus, said method comprising:
  obtaining a three-dimensional computer model (3D-model) of at least part of the auditory canal, said 3D-model comprising an outer surface;
  a) initially arranging at least one component comprising a component surface in relation to the 3D-model;
  b) initially arranging a cutting curve or cutting surface in relation to the outer surface of the 3D-model, said cutting curve or cutting surface defining a cut through said 3D-model, thereby dividing the 3D-model into an inner portion and an outer portion, said inner portion and said outer portion being separated by said cut;
  c) after arranging said at least one component, forming a new, connecting surface, wherein the connecting surface is a new surface additional to the component surface and the inner portion of the 3D-model, said connecting surface connecting the component surface of the at least one component and the inner portion of the 3D-model, said connecting surface thereby being part of the 3D-model;
  d) performing an evaluation of the arrangement of the at least one component, said evaluation comprising a collision detection of the at least one component in relation to one or more parts of the 3D-model, other components, or a combination of one or more parts of the 3D-model and other components; and
  e) if results of said evaluation are not satisfactory then adjusting one or more of the arrangement of the at least one component, the arrangement of the cutting curve or cutting surface, and the formation of the connecting surface based on the results of said evaluation;
  f) if the results of said evaluation are satisfactory, then completing the three-dimensional computer model.

2. The method according to claim 1, wherein steps (d) and (e) are repeated until the collision detection fulfils a given minimum criterion.

3. The method according to claim 1, further comprising the adjustment of one or more of the arrangement of the at least one component, the arrangement of the cutting curve or cutting surface, and the formation of the connecting surface until no collision is detected.

4. The method according to claim 1, further comprising:
  (g) shelling at least part of the inner portion of the 3D-model to form a shelled part having a shell.

5. The method according to claim 1, wherein an object function, $f(v)$, is defined for expressing a quality or correctness of one or more of the arrangement of the at least one component, the arrangement of the cutting curve or cutting surface, and the formation of the connecting surface, said object function being an increasing function of the number of detected collisions and being calculated for each new arrangement of at least one of the at least one component and each new arrangement of the cutting curve or cutting surface, and wherein at least one of the arrangement of the at least one component, the arrangement of the cutting curve or cutting surface, and the formation of the connecting surface is/are adjusted until the object function fulfils a given minimum criterion.

6. The method according to claim 5, wherein said minimum criterion is that the object function obtains a minimum value, or that the difference in the values of two successively determined object functions is below a defined value.

7. The method according to claim 5, wherein said object function consists of a weighted sum of terms related to constraints and a number of other terms, which express the quality of the earpiece.

8. The method according to claim 7, wherein the other terms are selected from the group consisting of the volume of the shell, the outer shell surface, the visible shell surface area, the length of intersection between the reference ear and the cutting surface, the area of the cutting surface after the cut, the maximal penetration of the reference ear by a component, the average of the penetration and the acoustic properties.

9. The method according to claim 1, wherein a general purpose optimization algorithm, pseudo physics or a combination are used to optimize component placement.

10. The method according to claim 1, wherein the steps are performed in the order a), b), c), d) e), f).

11. The method according to claim 1, wherein the steps are performed in the order a), c), b), d), e), f).

12. The method according to claim 1, wherein the step of obtaining a 3D model includes scanning an impression of one or more of the auditory canal, concha and meatus and part of the outer ear.

13. The method according to claim 1, wherein the step of obtaining a 3D model includes ultrasound scanning of one or more of the auditory canal, concha and meatus.

14. The method according to claim 1, wherein the step of obtaining a 3D model includes scanning one or more of the auditory canal, concha and meatus with a 3D structured light scanner.

15. The method according to claim 1, wherein the step of obtaining a 3D model includes one or more of CT, MRI, and MR scanning of one or more of the auditory canal, concha and meatus.

16. The method according to claim 1, comprising a further step during which holes in the 3D model are closed.

17. The method according to claim 1, comprising a further step during which defects are removed from the 3D model.

18. The method according to claim 17, wherein defects are selected from the group consisting of the thread used for removing the impression, artefacts, scars, earwax, tissue, and hair.

19. The method according to claim 1, further comprising removing unwanted parts of the 3D model surface.

20. The method according to claim 19, whereby unwanted parts are removed using a cutting curve/surface.

21. The method according to claim 19, whereby unwanted parts are removed by marking the parts on the 3D-model.

22. The method according to claim 1, comprising a further step during which a second cutting surface/curve is arranged in relation to the outer surface of the 3D model.

23. The method according to claim 1, wherein the arrangement of the at least one component in relation to the 3D-model comprises arranging a component surface of the at least one component in relation to the 3D-model.

24. The method according to claim 23, wherein a connecting surface is connecting said component surface and said inner portion of the 3D-model.

25. The method according to claim 1, wherein said initial arrangement of the at least one component in relation to the 3D-model comprises arranging at least part of the at least one component at the interior of the 3D-model.

26. The method according to claim 1, wherein said evaluation includes an evaluation of at least one of the arrangement of the cutting curve or cutting surface, and the connecting surface.

27. The method according to claim 26, wherein the evaluation includes at least one of a visual evaluation of the arrangement, an acoustic evaluation, and an evaluation of the fit in relation to a virtual ear.

28. The method according to claim 1, wherein the formation of the connecting surface is computer controlled or computer assisted.

29. The method according to claim 1, wherein the formation of the connecting surface comprises a lofting process.

30. The method according to claim 29, wherein the lofting process comprises fitting a parametric surface to the boundary of the inner portion of the 3D-model and to the boundary of a surface defining an outer boundary of said at least one component in relation to the 3D-model.

31. The method according to claim 1, wherein the formation of the connecting surface comprises a filleting process of the edge or boundary of the inner portion of the 3D-model.

32. The method according to claim 31, wherein the outer surface of the 3D-model is given in a vertex representation with the vertices being connected by triangles, and the filleting process comprises removing at least part of the triangles in a neighborhood around at least part of said edge and fitting a parametric surface to the neighborhood of the hole created by the removed triangles.

33. The method according to claim 30, wherein the parametric surface comprises a cubic B-spline surface.

34. The method according to claim 31, wherein filleting comprises smoothing on the edge and its neighborhood.

35. The method according to claim 1, wherein at least part of the inner portion of the 3D-model is shelled, said shelled inner portion having an inner and an outer shell surface.

36. The method according to claim 35, wherein the shell of the 3D-model is generated by a shelling process being computer controlled or computer assisted.

37. The method according to claim 35, wherein the shell of the 3D-model has a predetermined minimum shell thickness.

38. The method according to claim 35, wherein the at least partly shelled 3D-model is obtained from a three-dimensional computer model of at least part of the auditory canal, said 3D-model having an outer shell surface being parameterized by a number of vertices, which vertices are connected by triangles, said shelling process comprising:
   offsetting inwardly a copy of each vertex in the outer shell surface;
   removing the number of copied vertices being closer to the outer shell surface than a given minimum shell thickness; and
   creating an inner shell by triangulation of the remaining copied vertices.

39. The method according to claim 38, wherein the size of the offset varies over the surface.

40. The method according to claim 1, wherein the inner shell surface or geometry of the 3D-model is modified in order to improve the strength of the shell of the shelled part of the inner portion, said modification comprising adding extra material to at least part of the inner surface of the shell, while at the same time avoiding collision between the modified inner shell surface and the arranged components.

41. The method according to claim 40, wherein adding or removal of material to the inner shell surface of the 3D-model is performed using a Boolean operation.

42. The method according to claim 40, wherein adding or removal of material in an area comprises selection of a point and the amount of offset is a function of the distance from the point.

43. The method according to claim 1, further comprising a process comprising an outward offset on at least part of the outer surface of a 3D computer model, said 3D model having an outer surface being parameterized by a number of vertices, which vertices are connected by triangles, said process comprising outwardly offsetting a copy of each vertex in the outer surface, and removing the number of copied vertices being closer to the outer surface than a given minimum distance, and creating a new offset surface by triangulation of the remaining copied vertices.

44. The method according to claim 43, further comprising a lofting process to connect the offset part(s) to the non-offset part(s).

45. The method according to claim 12, wherein an anatomical atlas is used to map soft and hard parts of at least one of the auditory canal, the concha and the meatus to the model.

46. The method according to claim 45, wherein models are grouped to different anatomical atlases by selecting an atlas that most nearly corresponds with the model.

47. The method according to claim 1, wherein the inner portion of the 3D-model at least partly comprises a representation of a model of an earpiece.

48. The method according to claim 1, wherein the outer portion of the 3D-model at least partly comprises a model of a virtual ear.

49. The method according to claim 48, wherein said virtual ear is connected to a 3D head model.

50. The method according to claim 1, wherein the collision detection includes a collision detection of a component surface in relation to at least one part of the 3D-model.

51. The method according to claim 1, wherein the collision detection of the components includes a collision detection of the mutual arrangement of the components themselves.

52. The method according to claim 1, wherein said at least one part of the 3D-model in relation to which the collision detection is performed comprises at least one of at least part of the inner portion and at least part of the outer portion of the 3D-model.

53. The method according to claim 50, wherein said at least one part of the 3D-model in relation to which the collision detection is performed comprises at least part of the inner shell surface.

54. The method according to claim 50, wherein said at least one part of the 3D-model in relation to which the collision detection is performed comprises at least part of an inner surface of the virtual ear.

55. The method according to claim 1, wherein said collision detection is computer-controlled or computer-assisted.

56. The method according to claim 1, wherein at least one of the component and component surface is used to generate the initial cutting curve curve/surface.

57. The method according to claim 1, wherein initial cutting is performed by the component surface.

58. The method according to claim 1, wherein initial cutting is performed by a curve/surface derived from the component surface.

59. The method according to claim 1, wherein the initial cutting curve/surface is generated without the component or component surface.

60. The method according to claim 1, wherein the initial cutting curve/surface is marked on an impression before scanning said impression and said marking is used to generate the initial cutting curve/surface.

61. The method according to claim 1, wherein said initial arrangement of at least one of the at least one component, and the cutting curve or surface, is performed manually.

62. The method according to claim 1, wherein said initial arrangement of the at least one component, said initial arrangement of the cutting curve or surface, or both the initial arrangement of the at least one component and the initial arrangement of the cutting curve or surface is performed using a feature-based approach, in which features extracted from the obtained 3D-model are used for each arrangement.

63. The method according to claim 62, whereby texture marked on the impression used to generate the 3D-model is used for initial arrangement.

64. The method according to claim 62, comprising slicing at least part of the model into slices, selecting a slice fulfilling a number of constraints, and using this slice for initial placement of the at least one component.

65. The method according to claim 1, wherein said initial arrangement of the at least one component, the initial arrangement of the cutting curve or surface, or both the initial arrangement of the at least one component and the initial arrangement of the cutting curve or cutting surface is performed using a similarity-based approach, in which the obtained 3D-model is compared to a number of stored 3D-models of previously generated optimized optimised models to select a stored 3D-model that most nearly corresponds with the obtained 3D-model.

66. The method according to claim 1, wherein said initial arrangement of the at least one component, the initial arrangement of the cutting curve or surface, or both the initial arrangement of the at least one component and the initial arrangement of the cutting curve or cutting surface is performed based on mirroring from the optimized other ear of the same person.

67. The method according to claim 1, wherein said initial arrangement of the at least one component, the initial arrangement of the cutting curve or surface, or both the initial arrangement of the at least one component and the initial arrangement of the cutting curve or cutting surface is performed based on an earlier optimized model from the same person.

68. The method according to claim 65, wherein a stored optimized 3D-model is selected as the stored 3D-model most nearly corresponding to the obtained 3D-model and at least one of the initial arrangement of the at least one component, and the initial arrangement of the cutting curve or cutting surface, is selected substantially equal to the optimized arrangement of at least one of the at least one component, and the cutting curve or cutting surface, of said selected stored 3D-model.

69. The method according to claim 65, wherein said comparison of 3D-models and selection of a stored 3D-model is computer-controlled or computer-assisted.

70. The method according to claim 68, wherein said selection of initial arrangements of at least one of the at least one component, and the cutting curve or cutting surface, is computer-controlled or computer-assisted.

71. The method according to claim 1, wherein said adjustment(s) of the arrangement of at least one of the at least one component, and the cutting curve or surface, is performed manually.

72. The method according to claim 1, wherein said adjustment(s) of the arrangement of at least one of the at least one component, the arrangement of the cutting curve or cutting surface, and the formation of the connecting surface, is computer-controlled or computer-assisted.

73. The method according to claim 1, said method further comprising arrangement of components at the interior or inner surface of the inner portion of the 3D-model.

74. The method according to claim 73, wherein the arrangement of components at the interior or inner surface is optimized using a general purpose optimization optimisation algorithm, by pseudo physics or using a combination of both.

75. The method according to claim 1, wherein at least part of the components are selected from the group of components consisting of: electronic components, outlets to interior components, tubes, ventilation channel, amplifier, microphone, vibration pick-up, microchip, transducer, wireless communication/identification devices, position sensors, loudspeaker, tubes, battery, printed circuits, faceplate, surface patches, inlets, outlets, wires, conductors, volume controls, nail grip, extraction cord, tele coil, locking means, interface modules, identification and logo.

76. The method according to claim 1, said method further comprising arrangement of a ventilation channel at the interior or inner surface of the inner portion of the 3D-model.

77. The method according to claim 76, comprising arranging exit points on the canal part and the outer surface of the 3D model.

78. The method according to claim 76, wherein the channel is created by adding a solid object defined along a path between the exits to the inner shell surface of the model.

79. The method according to claim 78, further comprising subtracting an object having the shape of the ventilation channel.

80. The method according to claim 76, wherein the channel is created by adding a hollow object defined along a path between the exits to the inner shell surface of the model.

81. The method according to claim 76, wherein the ventilation channel is arranged on the outer surface of the model.

82. The method according to claim 1, comprising arrangement of further channels in the 3D model.

83. The method according to claim 76, wherein one or both of ventilation channels and sound bores are applied to improve at least one of the acoustic properties and protection against earwax.

84. The method according to claim 76, wherein the cross section of the ventilation channel is circular or elliptical or square/rectangular or T-shaped, or semi-circular with an edge, or triangular with an edge or circular/elliptical with an edge.

85. The method according to claim 76, wherein said arrangement of channels is performed manually.

86. The method according to claim 76, wherein said arrangement of channels is performed in a computer assisted manner by a person.

87. The method according to claim 76, wherein said arrangement of channels is fully computer controlled.

88. The method according to claim 87, wherein said arrangement is based on a shortest path algorithm.

89. The method according to claim 1, said method further comprising placement of a unique identifier at the inner portion of the 3D-model.

90. The method according to claim 1, wherein the optimized 3D model is divided into two or more parts by arranging one or more further cutting surfaces.

91. The method according to claim 1, further comprising visualization of the optimized model.

92. The method according to claim 1, further comprising production of a difference map illustrating the difference between the original 3D model and the optimized 3D model.

93. The method according to claim 1, further comprising acoustic modeling of the 3D model.

94. The method according to claim 1, further comprising generation of assembly instructions.

95. The method according to claim 1, further comprising prototyping and assembly of the earpiece.

96. The method according to claim 95, wherein the assembly is manual.

97. The method according to claim 95, wherein the assembly is performed by a robot being controlled by instructions generated by the computer.

98. The method according to claim 1, further comprising generation of instructions for milling a faceplate, and computer-controlled milling of the faceplate.

99. The method according to claim 1, wherein said connecting surface is a closing surface, closing the hole partly or completely created in the 3D-model by the cutting curve/cutting surface.

100. The method according to claim 1, wherein said initial arrangement of at least one of the at least one component, and the cutting curve or cutting surface, is performed using a similarity-based approach, in which the presently obtained 3D-model is compared to a number of stored models of previously generated optimized 3D-models, with one of said stored 3D-models being selected as the model most nearly corresponding with the presently obtained 3D-model, and the initial arrangement of the at least one component and the cutting curve or cutting surface being set equal to the optimized arrangements of the at least one component and the cutting curve or cutting surface of said selected stored 3D-model.

101. The method according to claim 100, wherein said comparison of the presently obtained 3D-models and selection of the selected stored 3D-model is computer controlled or computer assisted.

102. The method according to claim 100, wherein said selection of initial arrangement of the at least one component and the cutting curve or cutting surface is computer controlled or computer assisted.

103. The method according to claim 100, said method further comprising the step of initially forming the connecting surface connecting the at least one component and the inner portion of the 3D-model, said connecting surface thereby being part of the 3D-model.

104. The method according to claim 100, wherein the present 3D-model and the stored previously optimized 3D-models have an outer shell surface being parameterized by a number of vertices, which vertices are connected by triangles, and said selection of the most similar 3D-model comprises:
 extracting a number of features from the present 3D-model;
 comparing said number of extracted features with corresponding stored features of a number of stored 3D-models; and
 selecting a number of stored 3D-models as candidates for the most similar 3D-model, said candidates being the stored 3D-models having the compared features being nearest neighbours, in a feature space, to the feature points of the present 3D-model.

105. The method according to claim 104, said method further comprising:
 registration of the present 3D-model and the selected candidate 3D-models; and
 selection of the most similar 3D-model as the model of candidate 3D-models having the smallest distance between the outer shell surface of said candidate 3D-model and the outer shell surface of the present 3D-model.

106. The method according to claim 1, further comprising:
 said initial arrangement of at least one of the at least one component, and the cutting curve or cutting surface, being performed using a feature-based approach, in which features extracted from the obtained 3D-model are used for the arrangement;
 performing an evaluation of the arrangement of the at least one component, said evaluation comprising a collision detection of at least one of the at least one component in relation to at least one part of the 3D-model and the other components; and
 adjusting the arrangement of the at least one component and the arrangement of the cutting curve or cutting surface based on the result of said evaluation to create a new 3D model of an earpiece.

107. A nontransitory computer readable medium storing thereon a computer program, said program for causing computer-assisted modeling of customized earpieces comprising at least one part being individually matched to an auditory canal, said medium comprising:
 program code for causing a computer to obtain a three-dimensional computer model (3D-model) of at least part of the auditory canal, said 3D-model having an outer surface;
 program code for causing a computer to initially arrange at least one component comprising a component surface in relation to the 3D-model;
 program code for causing a computer to initially arrange a cutting curve or cutting surface in relation to the outer surface of the 3D-model, said cutting curve or cutting surface defining a cut through said 3D-model, thereby dividing the 3D-model into an inner portion and an outer portion, said inner portion and said outer portion being separated by said cut;

program code for causing a computer, after initially arranging said at least one component, to form a new, connecting surface, wherein the connecting surface is a new surface additional to the component surface and the inner portion of the 3D-model, said connecting surface connecting the component surface of the at least one component and the inner portion of the 3D-model, said connecting surface thereby being part of the 3D-model;

program code for causing a computer to perform an evaluation of the arrangement of the at least one component, said evaluation comprising a collision detection of the at least one component in relation to one or more parts of the 3D-model;

program code for causing a computer to, if results of said evaluation are not satisfactory, then adjust one or more of the arrangement of the at least one component, the arrangement of the cutting curve or cutting surface, and the formation of the connecting surface based on the result of said evaluation, said computer-adjusted arrangement modeling an optimized earpiece having at least one part individually matched to an auditory canal; and program code for using said computer-adjusted arrangement to model an optimized earpiece and to produce said earpiece.

108. The nontransitory computer readable medium according to claim 107, in the physical form of a hard disc, a floppy disc, a magnetic data carrier, a ZIP, a smart card, a CD ROM, or a DVD.

109. The nontransitory computer readable medium according to claim 107, further comprising program code for shelling at least part of the inner portion of the 3D-model.

110. A system for computer-assisted modeling of customized earpieces, said system including a nontransitory computer readable memory having one or more computer instructions stored thereon, said memory comprising:

instructions operative to cause the computer to obtain a three-dimensional computer model (3D-model) of at least part of the auditory canal, said 3D-model comprising an outer surface;

instructions operative to cause the computer to initially arrange at least one component comprising a component surface in relation to the 3D-model;

instructions operative to cause the computer to initially arrange a cutting curve or cutting surface in relation to the outer surface of the 3D-model, said cutting curve or cutting surface defining a cut through said 3D-model, thereby dividing the 3D-model into an inner portion and an outer portion, said inner portion and said outer portion being separated by said cut;

instructions operative to cause the computer, after arranging said at least one component, to form a new, connecting surface, wherein the connecting surface is a new surface additional to the component surface and the inner portion of the 3D-model, said connecting surface connecting the component surface of the at least one component and the inner portion of the 3D-model, said connecting surface thereby being part of the 3D-model;

instructions operative to cause the computer to perform an evaluation of the arrangement of the at least one component, said evaluation comprising a collision detection of the at least one component in relation to one or more parts of the 3D-model;

instructions operative to cause the computer to, if results of said evaluation are not satisfactory, then adjust one or more of the arrangement of the at least one component, the arrangement of the cutting curve or cutting surface, and the formation of the connecting surface based on the result of said evaluation, said computer-adjusted arrangement modeling an optimized earpiece having at least one part individually matched to an auditory canal; and instructions for using said computer-adjusted arrangement to model an optimized earpiece and to produce said earpiece.

111. The system according to claim 110, comprising a 3D scanner, a computer and a computer controllable rapid prototyping machine.

112. The system according to claim 111, wherein the rapid prototyping machine is capable of performing one or more of 3D milling, stereo lithography/SLA, solid ground curing, selective laser sintering, direct shell production casting, 3D-printing, topographic shell fabrication, fused deposition modeling, inkjet modeling, laminated object manufacturing and nano-printing.

113. The system according to claim 110, further comprising a database, wherein scan data are stored.

114. The system according to claim 113, comprising a further database, wherein 3D data for customized earpieces are stored.

115. The system according to claim 113, wherein the data are stored together with information identifying the users of the customized earpieces.

116. The system according to claim 110, further comprising a database, wherein 3D data for components from different manufacturers are stored.

117. The system according to claim 110, further comprising stereo glasses to assist in manual inspection of 3D computer screen models.

118. The system according to claim 110, further comprising a robot for automatic assembly of the earpiece.

119. The method according to claim 1, comprising arrangement of further channels in the 3D model comprising at least one of the types of a large bore (horn effect), a small bore (reverse horn effect), an open bore, a fishmouth bore (bell bore), an angle vent, an external vent, a parallel vent or a mini vent plug.

120. The system according to claim 110, further comprising instructions for shelling at least part of the inner portion of the 3D-model.

* * * * *